CERTAIN ARYL-ALKANE-2-PYRIDYLOXY-PHENYL DERIVATIVES HAVING INSECTICIDAL AND ACARICIDAL ACTIVITY

Inventors: Kiyoshi Nakatani, Tokyo; Satoshi Numata, Kanagawa; Kenji Kodaka, Kanagawa; Kengo Oda, Kanagawa; Shiro Shiraishi, Kanagawa; Takatoshi Udagawa, Kanagawa, all of Japan

Assignee: Mitsui Toatsu Chemicals, Inc., Tokyo, Japan

Appl. No.: 833,675

Filed: Feb. 26, 1986

Related U.S. Application Data

Continuation of Ser. No. 493,756, May 11, 1983, abandoned.

Foreign Application Priority Data

May 18, 1982 [JP] Japan .................. 57-82473

Int. Cl.$^4$ .................. C07D 213/64; A01N 43/40
U.S. Cl. .................. 514/345; 514/351; 546/300; 546/301; 546/302; 546/283; 546/284; 546/330; 568/631; 568/632; 568/635; 568/636; 568/637
Field of Search .............. 546/300, 330, 290, 283, 546/284, 302, 301; 568/631, 632, 635, 636, 637; 558/388; 514/345, 351

References Cited

U.S. PATENT DOCUMENTS 2,079,279  5/1937  Coleman et al. .................. 568/636

FOREIGN PATENT DOCUMENTS 2085006A  4/1982  United Kingdom .............. 568/636

*Primary Examiner*—Alan L. Rotman
*Attorney, Agent, or Firm*—Browdy and Neimark

ABSTRACT

The present invention relates to novel aromatic alkane derivatives represented by the following general formula (I):

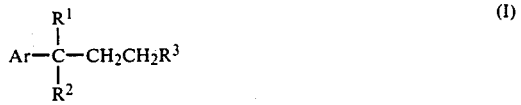

wherein Ar stands for a substituted or unsubstituted phenyl or naphthyl group, $R^1$ stands for a methyl, ethyl or isopropyl group and $R^2$ stands for a hydrogen atom or a methyl group, or $R^1$ and $R^2$ together with the carbon to which they are attached jointly represent a substituted or unsubstituted cycloalkyl group and $R^3$, stands for a fundamental group of an alcohol which is usually used in a form of $R^3OH$ as to natural or synthetic pyrethroids, and also to the uses of these compounds.

These compounds of the present invention have excellent insecticidal and acaricidal activities while the toxicities of these compounds are very low.

3 Claims, No Drawings

CERTAIN ARYL-ALKANE-2-PYRIDYLOXY-PHENYL DERIVATIVES HAVING INSECTICIDAL AND ACARICIDAL ACTIVITY

This application is a continuation of application Ser. No. 493,756, filed 5/11/83 now abandoned.

DETAILED DESCRIPTION OF THE INVENTION

The present invention relates to novel aromatic alkane derivatives, processes for the preparation thereof, and insecticidal and acaricidal agents containing said derivative as an active ingredient.

The present invention relates to novel compounds, namely aromatic alkane derivatives represented by the following general formula (I):

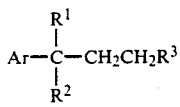   (I)

wherein Ar stands for a substituted or unsubstituted phenyl or naphthyl group, $R^1$ stands for a methyl, ethyl or isopropyl group and $R^2$ stands for a hydrogen atom or a methyl group, or $R^1$ and $R^2$ together with the carbon to which they are attached jointly represent a substituted or unsubstituted cycloalkyl group, and $R^3$ stands for a fundamental group of an alcohol which is usually used in a form of $R^3OH$ as to natural or synthetic pyrethroids.

Incidentally, the general formula (I) stands for also various optical isomers and the mixtures thereof, which are possibly in existence.

Further, the present invention relates to a process for preparation of the compounds represented by the general formula (I) above described, which comprises reacting a ketone represented by the general formula (VII):

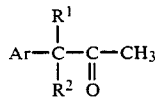   (VII)

wherein Ar, $R^1$ and $R^2$ are as defined above, with an aldehyde represented by the general formula (VIII):

   (VIII)

wherein $R^{12}$ stands for a fundamental group of an alcohol which is usually used in a form of $R^{12}CH_2OH$ as to synthetic pyrethroids, to give an α, β-unsaturated carbonyl compound represented by the general formula (IX):

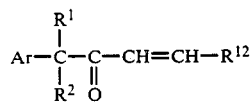   (IX)

wherein Ar, $R^1$, $R^2$ and $R^{12}$ are as defined above, and reducing the α, β-unsaturated carbonyl compound.

Further, the present invention relates to a process for preparation of the compounds represented by the general formula (I) above described, which comprises reacting an aldehyde represented by the general formula (X):

   (X)

wherein Ar, $R^1$ and $R^2$ are as defined above, with a ketone represented by the general formula (XI):

   (XI)

wherein $R^{12}$ stands for the fundamental group of the alcohol which is usually used in a form of $R^{12}CH_2OH$ as to synthetic pyrethroids, to give an α, β-unsaturated carbonyl compound represented by the general formula (XII):

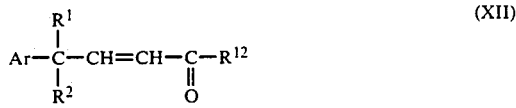   (XII)

wherein Ar, $R^1$, $R^2$ and $R^{12}$ are as defined above, and reducing the α, β-unsaturated carbonyl compound.

Further, the present invention relates to a process for preparation of the compounds represented by the general formula (I) above described, which comprises reacting an aldehyde represented by the general formula (XIII):

   (XIII)

wherein Ar, $R^1$ and $R^2$ are as defined above, with a compound represented by the general formula (XIV) or (XV):

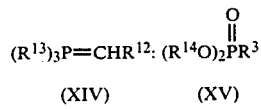

wherein $R^3$ and $R^{12}$ are as defined above, $R^{13}$ stands for an alkyl or phenyl group, and $R^{14}$ stands for an alkyl group, to give an olefin represented by the general formula (XVI) or (XVII):

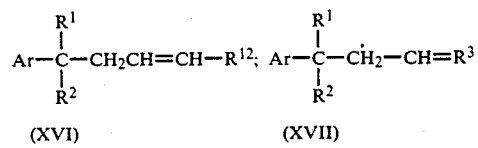

wherein Ar, $R^1$, $R^2$, $R^{12}$ and $R^3$ are as defined above, and reducing the olefin.

Further, the present invention relates to insecticidal and acaricidal agents containing as an active ingredient the aromatic alkane derivative represented by the general formula (I).

As an insecticide for agriculture, gardening or disinfection, various agents have hitherto been developed as follows: organochlorine insecticides, such as DDT, BHC, etc.; organophosphorous insecticides, such as parathion, malathion, etc.; carbamate insecticides, such as carbaryl, methomyl, etc. These insecticides have been used much for prevention of the breeding and extermination of agricultural insect pests or sanitary insect pests, and have taken very important roles in protecting farm product from such insect pests.

However, the uses of such insecticides have been examined lately concerning public problem, such as environmental pollution, etc. or concerning safety in the residue, accumulation, etc., of such insecticides. Some of such insecticides have brought about insect pests having acquired resistance to an insecticide applied, as a result of applying for a long time.

Under such background, pyrethroid compounds have proved to be low toxic compounds themselves and easily decomposed in applied environments, and further have proved that the substances produced by decompositions of pyrethroids compounds are safe, and therefore have been developed as an insecticide and applied actually. However, the actually applied pyrethroid compounds have a defect in that the fish toxicity is high. Though pyrethroids with a low fish toxicity have been researching and reported, it can not be denied that the lower the fish toxicity becomes, the lower the insecticidal activity becomes.

The present inventors made researches with a view to developing insecticidal and acaricidal agents without the above described defects which have a high safety to warm-blooded animals and fish, and the present inventors found that the novel aromatic alkane derivatives represented by the following general formula (I):

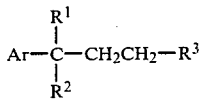
(I)

wherein Ar $R^1$, $R^2$ and $R^3$ are as defined above, are safe to warm-blooded animals and also low toxic to fish, and have a high insecticidal and acaricidal activity. The present inventors have now completed the present invention based on these findings.

Conventional pyrethroid compounds are generally cyclopropanecarboxylic acid esters represented by the general formula (A):

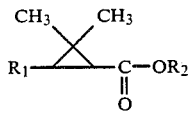
(A)

Changing the segments of cyclopropanecarboxylic acid esters have been researching variously, and it was found that the compounds prepared by changing the cyclopropanecarboxylic acid part to the substituted acetic acid as shown by the general formula (B):

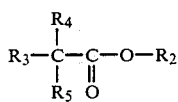
(B)

have a high insecticidal activity (M. Elliott et al, Chem. Soc. Reviews, 1978, 473, Japanese Patent Official Gazette Laying-Open Nos. Sho. 49-26425 and Sho. 49-126826). Changing the ester linkages have also been researching variously, and it was found lately that the compounds having an oxime ether linkage, represented by the general formula (C):

(C)

have a high insecticidal activity (Japanese Patent Official Gazette Laying-Open Nos. Sho. 53-103449, Sho. 54-141740 and Sho. 54-138532). Further, the compounds having such an ether linkage as shown by the general formula (D):

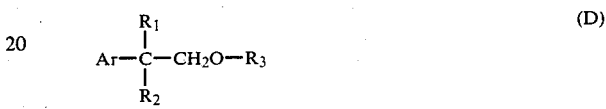
(D)

have a high insecticidal activity (West German Patent Official Gazette Laying-Open No. 3117510).

The compounds of the present invention have a quite novel —$CH_2CH_2$— linkage instead of an ester linkage —COO—, and are represented by the general formula (I):

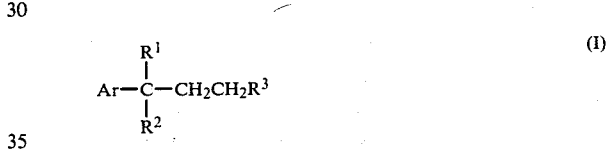
(I)

wherein Ar, $R^1$, $R^2$ and $R^3$ are as defined above, and have an active structure different from those of conventional agricultural chemicals, and are low toxic especially to warm-blooded animals and fish, and further have a high insecticidal and acaricidal activity.

A group

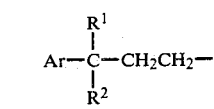

is an important part of an active structure in the compounds represented by the general formula (I). Ar stands for a substituted or unsubstituted phenyl or naphthyl group, and as the substituent thereof there can be exemplified a halogen atom, a nitro or cyano group, or a lower alkyl, alkenyl, alkynyl, cycloalkyl, aryl, lower alkoxy, alkenyloxy, alkynyloxy, alkylthio, cycloalkyloxy, aryloxy, lower acyl, alkoxycarbonyl, alkenyloxycarbonyl, alkynyloxycarbony, methylenedioxy, ethylendioxy group or polymethylene group having 3 to 5 carbons, etc., which are substituted or unsubstituted groups, and more particularly a lower haloalkyl, alkoxyalkyl, haloalkoxyalkyl, alkylthioalkyl, haloalkylthio, haloalkoxy, alkoxyalkoxy, haloalkoxyalkoxy, alkenyloxyalkoxy, haloalkenyloxy, haloalkynyloxy, alkoxyalkylthio, alkylthioalkoxy, alkylthioalkylthio, haloacyl, haloalkoxycarbonyl, haloalkenyloxycarbonyl, haloalkynyloxycarbonyl, 3,4-difluoromethylenedioxy, 3,4-trifluoroethylenedioxy, etc., and from the industrial viewpoint, a mono-or poly-substituted phenyl group of which the substituents are same or different substituents selected from the substituents above described, is preferable.

Specific examples of Ar group are described below though Ar that can be used in the present invention are not limited to those exemplified below. As specific examples of Ar group, there can be described a phenyl group, a 4-methylphenyl group, a 3,4-dimethylphenyl group, a 4-trifluoromethylphenyl group, a 3-methylphenyl group, a 3-trifluoromethylphenyl group, a 4-chlorophenyl group, a 3,4-dichlorophenyl group, a 4-nitrophenyl group, a 4-methylthiophenyl group, a 4-methoxyphenyl group, a 3,4-dimethoxyphenyl group, a 3,4-methylenedioxyphenyl group, a 4-difluoromethylthiophenyl group, a 4-trifluoromethylthiophenyl group, a 3,4-difluoromethylenedioxyphenyl group, a 4-cyanophenyl group, a 4-fluorophenyl group, a 4-bromophenyl group, a 3,4-difluorophenyl group, a 3,4-dibromophenyl group, a 4-chloro-3-fluorophenyl group, a 3-chloro-4-fluorophenyl group, a 3-chloro-4-methylphenyl group, a 3-bromo-4-chlorophenyl group, a 4-difluoromethoxyphenyl group, a 3,4-bis(difluoromethoxy)phenyl group, a 4-trifluoromethoxyphenyl group, a 3,4-bis(trifluoromethoxy)phenyl group, a 4-methoxy-3,5-dimethylphenyl group, a 3,4-trifluoroethylenedioxyphenyl group, a 4-tert-butylphenyl group, a 4-ethylphenyl group, a 4-isopropylphenyl group, a 3,4-difluoroethylenedioxyphenyl group, a 4-isopropenylphenyl group, a 4-vinylphenyl group, a 4-(2,2-dichlorovinyl)phenyl group, a 4-chloro-3-methylphenyl group, a 3-bromo-4-fluorophenyl group, a 2-naphthyl group, a 3-fluoro-4-bromophenyl group, a 4-fluoro-3-methylphenyl group, a 3-fluoro-4-methylphenyl group, a 3-bromo-4-methylphenyl group, a 3,4-diethylphenyl group, a 3,4-diisopropylphenyl group, a 3-ethyl-4-methylphenyl group, a 4-isopropyl-3-methylphenyl group, a 4-methylsulfinylphenyl group, a 4-allylphenyl group, a 4-acetylphenyl group, a 4-ethoxycarboethoxyphenyl group, a 4-ethoxyphenyl group, a 1,2,3,4-tetrahydronaphthalen-7-yl group, a 3,5-dichloro-4-methylphenyl group, a indan-5-yl group, a 4-propargylphenyl group, a 3-methoxy-4-methylphenyl group, a 4-methoxymethylphenyl group, a 4-(1-chloroethylen-1yl)phenyl group, a 4-(2-chloroallyl)phenyl group, a 4-isobutyrylphenyl group, a 4-methoxycarbonylphenyl group, a 3-nitro-4,5-dimethylphenyl group, a 3-ethoxy-4-bromophenyl group, a 3-chloro-4-methoxyphenyl group, a 4-bromo-3-chlorophenyl group, a 3,4-(di-tert-butyl)phenyl group, a 4-ethyl-3-methylphenyl group, a 4-tert-butyl-3-methylphenyl group, a 4-(1,1,2,2-tetrafluoroethoxy)phenyl group, a 4-(2,2-dichlorovinyloxy)phenyl group, a 4-(2,2,2-trifluoroethoxy)phenyl group, a 4-pentafluoroethoxyphenyl group, a 4-(chlorodifluoromethoxy)phenyl group, a 4-(chlorofluoromethoxy)phenyl group, a 4-(dichlorofluoromethoxy)phenyl group, a 4-(1,1-difluoroethoxy)phenyl group, a 4-(1,2,2-trichloro-1,2-difluoroethoxy)phenyl group, a 4-(2-bromo-1,1,2,2-tetrafluoroethoxy)phenyl group, a 4-(2-propynyloxy)phenyl group, a 4-(1-propynyloxy)phenyl group, a 4-allyloxyphenyl group, a 4-ethynyloxyphenyl group, a 4-(2-chloroethynylene)phenyl group, a 4-(n-propoxy)phenyl group, a 4-isopropoxyphenyl group, a 4-cyclopentyloxyphenyl group, a 4-(n-amyloxy)phenyl group, a 4-isobutoxyphenyl group, a 4-iodophenyl group, a 4-vinyloxyphenyl group, a 4-biphenyl group, a 4-(n-butoxy)phenyl group, a 4-(sec-butoxy)phenyl group, a 6-methyl-2-naphtyl group, a 4-phenoxyphenyl group, a 4-(2-iodo-1,1-difluoroethoxy)phenyl group, a 4-cyclohexyloxyphenyl group, a 3-chloro-4-ethoxyphenyl group, a 4-formylphenyl group, a 4-ethoxymethylphenyl group, a 4-trifluoroacetyloxyphenyl group, a 4-(1-ethoxyethyl)phenyl group, a 4-(1-methoxyethyl)phenyl group, a 4-ethoxy-3-methylphenyl group, a 4-(2-methylpropenyl)phenyl group, a 4-(1,2,2-trichlorovinyloxy)phenyl group, a 3,4-diethoxyphenyl group, a 4-ethynylphenyl group, a 4-ethoxy-3,5-dimethylphenyl group, a 4-ethoxy-3-methoxyphenyl group, a 4-ethylthiophenyl group, a 4-(2,2,2-trifluoroethoxycarbonyl)phenyl group, a 4-(2-chloroethoxy)phenyl group, a 4-(1-ethylvinyl)phenyl group, a 4-(1-methyl-1-propenyl)phenyl group, a 4-methoxymethylthiophenyl group, a 4-(1,2-dichlorovinyloxy)phenyl group, a 4-(2,3-dichloroallyloxy)phenyl group, a 4-(2-iodo-1-fluorovinyloxy) phenyl group, a 4-(2-fluoroethoxy)phenyl group, a 4-(2-chloro-1,1-difluoroethoxy)phenyl group, a 4-(2-chloro-1-fluorovinyloxy)phenyl group, a 4-isopropylthiophenyl group, a 4-(2,2-dichloro-1,1-difluoroethoxy)phenyl group, a 4-(2,2-dichloro-1-fluorovinyloxy)phenyl group, a 4-(1,1,2,2-tetrafluoroethoxy)phenyl group, a 3-chloro-4-ethoxyphenyl group, a 4-(tetrahydro-3-furyloxy)phenyl group, a 4-ethylthiophenyl group, 3-ethoxyphenyl group, a 4-allyloxyphenyl group, a 4-methoxymethylthiophenyl group, a 4-(2,2-dichlorovinyloxy)phenyl group, a 4-(1,1,1-trifluoroethoxy)phenyl group.

$R^1$ stands for a methyl, ethyl or isopropyl group, preferably a methyl or ethyl group. $R^2$ stands for a hydrogen atom or a methyl group, preferably a methyl group. $R^1$ and $R^2$ together with the carbon atom to which they are attached jointly may represent a substituted or unsubstituted cycloalkyl group, preferably a substituted or unsubstituted cycloalkyl group of 3 to 6 carbons, and in the case of the substituted cycloalkyl group, a halogen atom or a methyl group is preferably as the substituent.

$R^3$ corresponds to an alcoholic part which is known in a form of $R^3OH$ as to natural or synthetic pyrethroids.

$R^3$ is exemplified as follows:

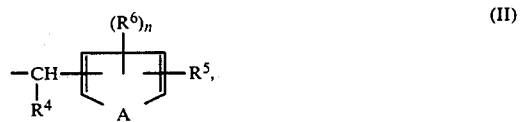

(II)

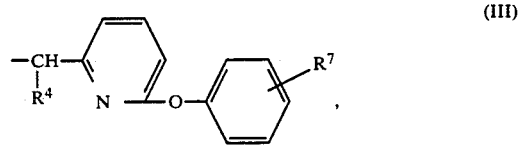

(III)

(IV)

(V)

wherein, $R^4$ stands for a hydrogen atom or an ethynyl or cyano group, $R^5$ stands for an allyl, propargyl, benzyl, thenyl, furylmethyl, phenoxy, phenylmercapto, benzoyl or pyridyloxy group which may be optionally substituted with a halogen atom, or an alkyl, alkoxy, haloalkyl, cyano or nitro group, and $R^6$ stands for a hydrogen or halogen atom, or an alkyl, alkoxy, haloalkyl, cyano or nitro group, and n stands for an integer of 1 to 4 with a proviso that when n is an integer not less than 2, the groups $R^6$ are selected independently each other, and A stands for an oxygen or sulfur atom, or —CH=CH—, and $R^7$ stands for a hydrogen or halogen atom, or methyl group or alkoxy group, and $R^8$ stands for a phthalimide, thiophthalimide, dihydrophthalimide, tetrahydrophthalimide or dialkylmaleimide group which may be optionally substituted, and $R^9$ stands for an alkyl, alkenyl, alkynyl or aralkyl group, and $R^{10}$ stands for a hydrogen atom or a methyl group.

As desirable examples of the $R^3$ group, there can be described a 5-benzyl-3-furylmethyl group, a 3-phenoxybenzyl group, 3-(4-fluorophenoxy)benzyl group, a 3-(4-bromophenoxy)benzyl group, a 3-(4-chlorophenoxy)benzyl group, a 3-(3-fluorophenoxy)benzyl group, a 3-(2-bromophenoxy)benzyl group, a 3-(3-chlorophenoxy)benzyl group, a 3-(4-methylphenoxy)benzyl group, a 3-(2-fluorophenoxy)benzyl group, a 3-(2-chlorophenoxy)benzyl group, a 3-(3-bromophenoxy)benzyl group, a 3-(3-methoxyphenoxy)benzyl group, a 3-(2-methylphenoxy)benzyl group, a 3-(4-ethoxyphenoxy)benzyl group, a 3-(4-methoxyphenoxy)benzyl group, a 3-(3-methylphenoxy)benzyl group, a 3-(2-methoxyphenoxy)benzyl group, a 3-phenylthiobenzyl group, a 3-benzoylbenzyl group, a 3-benzylbenzyl group, a 3-(4-chlorobenzyl)benzyl group, a 3-(4-fluorobenzyl)benzyl group, a 3-(3,5-dichlorophenoxy)benzyl group, a 3-(3,4-dichlorophenoxy)benzyl group, a 3-(4-chloro-2-methylphenoxy)benzyl group, a 3-(2-chloro-5-methylphenoxy)benzyl group, a 3-(4-chloro-3-methylphenoxy)benzyl group, a 3-(4-ethylphenoxy)benzyl group, a 3-(3-chloro-5-methoxyphenoxy)benzyl group, a 3-(4-fluorophenylthio)benzyl group, a 3-(3-fluorophenylthio)benzyl group, a 3-(3,5-dichlorobenzoyl)benzyl group, a 3-(3,4-dichlorobenzoyl)benzyl group, a 3-(2,5-dichlorobenzoyl)benzyl group, a 3-(4-methylbenzyl)benzyl group, a 3-(4-isopropoxyphenoxy)benzyl group, a 3-phenoxy-4-fluorobenzyl group, a 3-phenoxy-4-chlorobenzyl group, a 3-phenoxy-4-bromobenzyl group, a 3-(4-fluorophenoxy)-4-fluorobenzyl group, a 3-(4-bromophenoxy)-4-fluorobenzyl group, a 3-(4-chlorophenoxy)-4-fluorobenzyl group, a 3-(3-bromophenoxy)-4-fluorobenzyl group, a 3-(3-chlorophenoxy)-4-fluorobenzyl group, a 3-(4-methylphenoxy)-4-fluorobenzyl group, a 3-(4-methoxyphenoxy)-4-fluorobenzyl group, a 3-(2-fluorophenoxy)-4-fluorobenzyl group, a 3-phenoxy-5-methoxybenzyl group, a 3-(3-methoxyphenoxy)-4-fluorobenzyl group, a 3-phenoxy-2-fluorobenzyl group, a 3-(4-fluorophenoxy)-2-fluorobenzyl group, a 3-(3-fluorophenoxy)-2-fluorobenzyl group, a 3-(2-fluorophenoxy)-2-fluorobenzyl group, a 3-(4-fluorophenoxy)-5-fluorobenzyl group, a 3-(3-fluorophenoxy)-4-fluorobenzyl group, a 3-(3-fluorophenoxy)-5-fluorobenzyl group, a 3-(2-fluorophenoxy)-5-fluorobenzyl group, a 3-phenoxy-4-methylbenzyl group, a 3-(4-methylphenoxy)-5-fluorobenzyl group, a 3-(3-methoxyphenoxy)-5-fluorobenzyl group, a 3-(2-fluorophenoxy)-6-fluorobenzyl group, a 3-(3-fluorophenoxy)-6-fluorobenzyl group, a 3-(4-fluorophenoxy)-6-fluorobenzyl group, a 3-phenoxy-2-fluorobenzyl group, a 3-phenoxy-5-fluorobenzyl group, a 3-phenoxy-6-fluorobenzyl group, a 3-phenoxy-6-chlorobenzyl group, a 3-phenoxy-5-fluorobenzyl group, a 3-phenoxy-2-chlorobenzyl group, a 3-(3-methylphenoxy)-4-chlorobenzyl group, a 3-(4-fluorophenoxy)-4-chlorobenzyl group, a 3-phenoxy-5-chlorobenzyl group, a 3-phenoxy-6-bromobenzyl group, a 3-phenoxy-4-bromobenzyl group, a 3-phenoxy-5-bromobenzyl group, a 3-(4-ethoxyphenoxy)-4-fluorobenzyl group, a phthalimidomethyl group, a 3,4,5,6-tetrahydrophthalimidomethyl group, a 6-phenoxy-2-pyridylmethyl group, a 6-(4-fluorophenoxy)-2-pyridylmethyl group, a 6-(4-chlorophenoxy)-2-pyridylmethyl group, a 6-(4-bromophenoxy)-2-pyridylmethyl group, a 6-(4-methylphenoxy)-2-pyridylmethyl group, a 6-(3-fluorophenoxy)-2-pyridylmethyl group, a 6-(2-fluorophenoxy)-2-pyridylmethyl group, a 6-(2-chlorophenoxy)-2-pyridylmethyl group, a 6-(2-bromophenoxy)-2-pyridylmethyl group, a 6-(3-chlorophenoxy)-2-pyridylmethyl group, a 6-(3-bromophenoxy)-2-pyridylmethyl group, a 6-(4-ethoxyphenoxy)-2-pyridylmethyl group, a 6-(4-methoxyphenoxy)-2-pyridylmethyl group, a 6-(3-methoxyphenoxy)-2-pyridylmethyl group, a 3-(2-pyridyloxy)benzyl group, a 3-(3-pyridyloxy)benzyl group, a 3-(2-pyridyloxy)-4-fluorobenzyl group, a 3-(3-pyridyloxy)-4-fluorobenzyl group, a 3-(2-pyridyloxy)-4-chlorobenzyl group, a 3-(2-pyridyloxy)-4-methylbenzyl group, a 3-(2-pyridyloxy)-4-bromobenzyl group, a 3-(3-pyridyloxy)-4-chlorobenzyl group, a 3-(3-pyridyloxy)-4-bromobenzyl group, a 3-(3-pyridyloxy)-4-methylbenzyl group, a 3-phenoxy-4-trifluoromethylbenzyl group, a 3-phenoxy-α-cyano-benzyl group, a 3-phenoxy-α-ethynyl-benzyl group, a 3-(4-fluorophenoxy)-α-cyano-benzyl group, a 3-(4-fluorophenoxy)-α-ethynyl-benzyl group, a 3-(4-bromophenoxy)-α-cyano-benzyl group, a 3-(4-bromophenoxy)-α-ethynyl-benzyl group, a 3-(4-chlorophenoxy)-α-cyano-benzyl group, a 3-(4-chlorophenoxy)-α-ethynyl-benzyl group, a 3-(3-fluorophenoxy)-α-cyano-benzyl group, a 3-(3-fluorophenoxy)-α-ethynyl-benzyl group, a 3-(2-bromophenoxy)-α-cyano-benzyl group, a 3-(2-bromophenoxy)-α-ethynyl-benzyl group, a 3-(3-chlorophenoxy)-α-cyano-benzyl group, a 3-(3-chlorophenoxy)-α-ethynyl-benzyl group, a 3-(4-methylphenoxy)-α-cyano-benzyl group, a 3-(4-methylphenoxy)-α-ethynyl-benzyl group, a 3-(4-ethoxyphenoxy)-α-cyano-benzyl group, a 3-(4-ethoxyphenoxy)-α-ethynyl-benzyl group, a 3-(4-methoxyphenoxy)-α-cyano-benzyl group, a 3-(4-methoxyphenoxy)-α-ethynyl-benzyl group, a 3-phenylthio-α-cyano-benzyl group, a 3-phenylthio-α-ethynylbenzyl group, a 3-benzoyl-α-cyano-benzyl group, a 3-benzoyl-α-ethynyl-benzyl group, a 3-benzyl-α-cyano-benzyl group, a 3-benzyl-α-ethynyl-benzyl group, a 3-(4-chlorobenzyl)-α-cyanobenzyl group, a 3-(4-chlorobenzyl)-α-ethynyl-benzyl group, a 3-(4-fluorobenzyl)-α-cyano-benzyl group, a 3-(3,4-dichlorophenoxy)-α-cyano-benzyl group, a 3-(4-fluorophenylthio)-α-cyano-benzyl group, a 3-(4-fluorophenylthio)-α-ethynyl-benzyl group, a 3-phenoxy-4-fluoro-α-cyano-benzyl group, a 3-phenoxy-4-fluoro-α-ethynyl-benzyl group, a 3-phenoxy-4-chloro-α-cyanobenzyl group, a 3-phenoxy-4-chloro-α-ethynyl-benzyl group, a 3-phenoxy-4-bromo-α-cyano-benzyl group, a 3-phenoxy-4-bromo-α-ethynyl-benzyl group, a 3-(4-fluorophenoxy)-4-fluoro-α-cyanobenzyl group, a 3-(4-fluorophenoxy)-4-fluoro-α-ethynyl-benzyl group, a 3-(4-bromophenoxy)-4-fluoro-α-cyano-benzyl group, a 3-(4-bromophenoxy)-4-fluoro-α-ethynyl-benzyl group, a 3-(4-chlorophenoxy)-4-fluoro-α-cyano-benzyl group, a 3-(4-chlorophenoxy)-4-fluoro-α-ethynyl-benzyl group, a 3-(3-bromophenoxy)-4-fluoro-α-cyano-benzyl group, a 3-(3-bromophenoxy)-4-fluoro-α-ethynyl-benzyl group, a 3-(3-chlorophenoxy)-4- fluoro-α-cyano-benzyl group, a 3-(3-chlorophenoxy)-4-fluoro-α-ethynylbenzyl group, a 3-(4-methylphenoxy)-4-fluoro-α-cyano-benzyl group, a 3-(4-methylphenoxy)-4-fluoro-α-ethynyl-benzyl group, a 3-(4-methoxyphenoxy)-4-fluoro-α-cyano-benzyl group, a 3-(4-methoxyphenoxy)-4-fluoro-α-ethynyl-benzyl group, a 3-(2-fluorophenoxy)-4-fluoro-α-cyano-benzyl group, a 3-(2-fluorophenoxy)-4-fluoro-α-ethynyl-benzyl group, a 3-phenoxy-5-methoxy-α-cyano-benzyl group, a 3-phenoxy-5-methoxy-α-ethynylbenzyl group, a 3-(3-methoxyphenoxy)-4-fluoro-α-cyano-benzyl group, a 3-(3-methoxyphenoxy)-4-fluoro-α-ethynyl-benzyl group, a 3-(3-fluorophenoxy)-4-fluoro-α-cyano-benzyl group, a 3-(3-fluorophenoxy)-4-fluoro-α-ethynyl-benzyl group, a 3-phenoxy-4-methyl-α-cyano-benzyl group, a 3-phenoxy-4-methyl-α-ethynylbenzyl group, a 3-(3-methylphenoxy)-4-chloro-α-cyano-benzyl group, a 3-(3-methylphenoxy)-4-chloro-α-ethynyl-benzyl group, a 3-(4-fluorophenoxy)-4-chloro-α-cyano-benzyl group, a 3-(4-fluorophenoxy)-4-chloro-α-ethynyl-benzyl group, a 3-phenoxy-4-bromo-α-cyano-benzyl group, a 3-phenoxy-4-bromo-α-ethynylbenzyl group, a 3-(4-ethoxyphenoxy)-4-fluoro-α-cyano-benzyl group, a 3-(4-ethoxyphenoxy)-4-fluoro-α-ethynyl-benzyl group, a 6-phenoxy-α-cyano-2-pyridylmethyl group, a 6-phenoxy-α-ethynyl-2-pyridylmethyl group, a 6-(4-fluorophenoxy)-α-cyano-4-pyridylmethyl group, a 6-(4-fluorophenoxy)-α-ethynyl-4-pyridiylmethyl group, a 6-(4-chlorophenoxy)-α-cyano-2-pyridylmethyl group, a 6-(4-chlorophenoxy)-α-ethynyl-2-pyridylmethyl group, a 6-(4-bromophenoxy)-α-cyano-2-pyridylmethyl group, a 6-(4-bromophenoxy)-α-ethynyl-2-pyridylmethyl group, a 6-(4-methylphenoxy)-α-cyano-2-pyridylmethyl group, a 6-(4-methylphenoxy)-α-ethynyl-2-pyridylmethyl group, a 6-(3-fluorophenoxy)-α-cyano-2-pyridylmethyl group, a 6-(3-fluorophenoxy)-α-ethynyl-2-pyridylmethyl group, a 6-(2-fluorophenoxy)-α-cyano-2-pyridylmethyl group, a 6-(2-fluorophenoxy)-α-ethynyl-2-pyridylmethyl group, a 6-(2-chlorophenoxy)-α-cyano-2-pyridylmethyl group, a 6-(2-chlorophenoxy)-α-ethynyl-2-pyridylmethyl group, a 6-(3-chlorophenoxy)-α-cyano-2-pyridylmethyl group, a 6-(3-chlorophenoxy)-α-ethynyl-2-pyridylmethyl group, a 6-(3-bromophenoxy)-α-cyano-2-pyridylmethyl group, a 6-(3-bromophenoxy)-α-ethynyl-2-pyridylmethyl group, a 6-(4-ethoxyphenoxy)-α-cyano-2-pyridylmethyl group, a 6-(4-ethoxyphenoxy)-α-ethynyl-2-pyridylmethyl group, a 6-(4-methoxyphenoxy)-α-cyano-2-pyridylmethyl group, a 6-(4-methoxyphenoxy)-α-ethynyl-2-pyridylmethyl group, a 6-(3-methoxyphenoxy)-α-cyano-2-pyridylmethyl group, a 6-(3-methoxyphenoxy)-α-ethynyl-2-pyridylmethyl group, a 3-(2-pyridyloxy)-α-cyano-benzyl group, a 3-(2-pyridyloxy)-α-ethynyl-benzyl group, a 3-(3-pyridyloxy)-α-cyano-benzyl group, a 3-(3-pyridyloxy)-α-ethynyl-benzyl group, a 3-(2-pyridyloxy)-4-fluoro-α-cyano-benzyl group, a 3-(2-pyridyloxy)-4-fluoro-α-ethynylbenzyl group, a 3-(3-pyridyloxy)-4-fluoro-α-cyano-benzyl group, a 3-(3-pyridyloxy)-4-fluoro-α-ethynyl-benzyl group, a 3-(2-pyridyloxy)-4-chloro-α-cyano-benzyl group, a 3-(2-pyridyloxy)-4-methyl-α-cyano-benzyl group, a 3-(2-pyridyloxy)-4-methyl-α-ethynyl-benzyl group, a 3-(2-pyridyloxy)-4-bromo-α-cyanobenzyl group, a 3-(2-pyridyloxy)-4-bromo-α-ethynyl-benzyl group, a 3-(3-pyridyloxy)-4-chloro-α-cyano-benzyl group, a 3-(3-pyridyloxy)-4-chloro-α-ethynyl-benzyl group, a 3-(3-pyridyloxy)-4-bromo-α-cyano-benzyl group, a 3-(3-pyridyloxy)-4-bromo-α-ethynylbenzyl group, a 3-(3-pyridyloxy)-4-methyl-α-cyano-benzyl group, a 3-(3-pyridyloxy)-4-methyl-α-ethynyl-benzyl group, a 3-phenoxy-4-trifluoromethyl-α-cyano-benzyl group, a 3-phenoxy-4-trifluoromethyl-α-ethynyl-benzyl group, a 3-phenylthio-4-fluorobenzyl group, a 3-phenylthio-4-fluoro-α-cyano-benzyl group, a 3-phenylthio-4-fluoro-α-ethynyl-benzyl group, a 3-benzyl-4-fluorobenzyl group, a 3-benzyl-4-fluoro-α-cyano-benzyl group, a 3-benzyl-4-fluoro-α-ethynyl-benzyl group, a (2-allyl-3-methylcyclopentenon)-4-yl group, a 5-propargyl-2-methyl-3-furyl group, and so on.

Typical examples of the compounds according to the present invention will now be described. Of course, the compounds included in the scope of the present invention are not limited to those examplified below. The typical examples are as follows:

1-(3-Phenoxyphenyl)-4-(4-methoxyphenyl)-4-methylpentane

1-[3-(4-Fluorophenoxy)phenyl]-4-(4-fluorophenyl)-4-methylhexane 1-(3-Phenoxyphenyl)-4-(4-methoxyphenyl)-4-methylhexane 1-[3-(4-Fluorophenoxy)phenyl]-4-(4-fluorophenyl)-4-methylpentane 1-[3-(4-Fluorophenoxy)phenyl]-4-(4-methylphenyl)-4-methylpentane 1-[3-(4-Bromophenoxy)phenyl]-4-(4-chlorophenyl)-4-methylpentane 1-[3-(4-Bromophenoxy)phenyl]-4-(4-chlorophenyl)-4-methylhexane 1-(3-Phenoxyphenyl)-4-phenyl-4-methylpentane 1-(3-Phenoxyphenyl)-4-phenyl-4-methylhexane 1-(3-Phenoxyphenyl)-4-(4-chlorophenyl)-4-methylhexane 1-[3-(4-Fluorophenoxy)phenyl]-4-(4-chlorophenyl)-4-methylpentane 1-[3-(4-Fluorophenoxy)phenyl]-4-(4-ethoxyphenyl)-4-methylpentane 1-[3-(4-Fluorophenoxy)phenyl]-4-(4-chlorophenyl)-4-methylhexane 1-[3-(4-Fluorophenoxy)phenyl]-4-(3,4-dimethylphenyl)-4-methylpentane 1-(3-Phenoxyphenyl)-4-(3,4-dimethylphenyl)-4-methylpentane 1-(3-Phenoxyphenyl)-4-(3,4-methylenedioxyphenyl)-4-methylpentane 1-[3-(4-Methoxyphenoxy)phenyl]-4-(4-methylthiophenyl)-4-methylpentane 1-[3-(3-Chlorophenoxy)phenyl]-4-(4-chlorophenyl)-4-methylpentane 1-[3-(3-Chlorophenoxy)phenyl]-4-(4-Chlorophenyl)-4-methylhexane 1-[3-(3-Fluorophenoxy)phenyl]-4-(4-chlorophenyl)-4-methylpentane 1-[3-(3-Fluorophenoxy)phenyl]-4-(4-chlorophenyl)-4-methylhexane 1-[3-(4-Fluorophenoxy)phenyl]-4-(4-difluoromethoxyphenyl)-4-methylpentane 1-[3-(4-Fluorophenoxy)phenyl]-4-(4-difluoromethoxyphenyl)-4-methylhexane 1-(5-Benzyl-3-furyl)-4-(4-chlorophenyl)-4-methylpentane 1-(5-Benzyl-3-furyl)-4-(4-chlorophenyl)-4-methylhexane 1-[3-(4-Methoxyphenoxy)phenyl]-4-phenyl-4-methylpentane 1-[3-(4-Methoxyphenoxy)phenyl]-4-phenyl-4-methylhexane 1-[3-(2-Fluorophenoxy)phenyl]-4-(4-chlorophenyl)-4-methylpentane
1-[3-(4-Fluorophenoxy)phenyl]-4-(3-chloro-4-methylphenyl)-4-methylpentane
1-(3-Phenylthiophenyl)-4-(4-chlorophenyl)-4-methylpentane
1-(3-Phenoxyphenyl)-4-(4-trifluoromethylthiophenyl)-4-methylpentane
1-[3-(4-Bromophenoxy)phenyl]-4-(4-fluorophenyl)-4-methylhexane
1-[3-(4-Bromophenoxy)phenyl]-4-(4-fluorophenyl)-4-methylpentane
1-(3-Phenoxyphenyl)-4-(4-trifluoromethylphenyl)-4-methylpentane
1-(3-Phenoxyphenyl)-4-(4-trifluoromethylphenyl)-4-methylhexane
1-(3-Phenoxyphenyl)-4-(4-trifluoromethylthiophenyl)-4-methylpentane
1-[3-(4-Fluorophenoxy)phenyl]-4-(3,4-dichlorophenyl)-4-methylpentane
1-[3-(4-Fluorophenoxy)phenyl]-4-(3,4-dichlorophenyl)-4-methylhexane
1-(3-Phenoxyphenyl)-4-(4-difluoromethoxyphenyl)-4-methylpentane
1-[3-(4-Fluorophenoxy)phenyl]-4-(4-difluoromethylthiophenyl)-4-methylpentane
1-(3-Phenoxyphenyl)-4-(4-difluoromethoxyphenyl)-4-methylhexane
1-(3-Phenoxyphenyl)-4-(3,4-dimethoxyphenyl)-4-methylpentane
1-[3-(4-Chlorophenoxy)phenyl]-4-(4-cyanophenyl)-4-methylpentane
1-[3-(4-Fluorophenoxy)phenyl]-4-(3,4-difluorophenyl)-4-methylhexane
1-[3-(4-Methylphenoxy)phenyl]-4-(4-chlorophenyl)-4-methylpentane
1-[3-(4-Methylphenoxy)phenyl]-4-(4-chlorophenyl)-4-methylhexane
1-(3-Phenoxyphenyl)-4-(4-chlorophenyl)-4-methylpentane
1-[3-(2-Bromophenoxy)phenyl]-4-(3,4-dibromophenyl)-4-methylpentane
1-[3-(2-Chlorophenoxy)phenyl]-4-(4-trifluoromethoxyphenyl)-4-methylpentane
1-[3-(3-Methoxyphenoxy)phenyl]-4-(4-ethylphenyl)-4-methylpentane
1-[3-(2-Methylphenoxy)phenyl]-4-(4-isopropylphenyl)-4-methylpentane
1-[3-(4-Bromophenoxy)phenyl]-4-(3,4-dichlorophenyl)-4-methylpentane
1-[3-(4-Fluorophenoxy)phenyl]-4-(4-trifluoromethylthiophenyl)-4-methylpentane
1-[3-(4-Bromophenoxy)phenyl]-4-(3,4-dichlorophenyl)-4-methylhexane
1-[3-(3-Bromophenoxy)phenyl]-4-(1,2,3,4-tetrahydronaphthalene-7-yl)-4-methylpentane
1-[3-(4-Chlorobenzyl)phenyl]-4-(4-ethoxyphenyl)-4-methylpentane
1-[3-(3,5-Dichlorophenoxy)phenyl]-4-(indan-5-yl)-4-methylpentane
1-(3-Phenoxyphenyl)-4-(4-difluoromethylthiophenyl)-4-methylpentane
1-(3-Phenoxyphenyl)-4-(4-ethoxyphenyl)-4-methylpentane
1-(3-Phenoxyphenyl)-4-(4-ethoxyphenyl)-4-methylhexane
1-[3-(4-Fluorophenoxy)phenyl]-4-(4-ethoxyphenyl)-4-methylpentane
1-(3-Phenoxyphenyl)-4-(4-ethoxyphenyl)-4,5-dimethylhexane
1-(3-Phenoxyphenyl)-4-(4-ethoxyphenyl)-hexane
1-(3-Phenoxyphenyl)-4-(4-ethoxyphenyl)-5-methylhexane
1-[3-(4-Fluorophenoxy)phenyl]-4-(4-ethoxyphenyl)-4-methylhexane
1-[3-(4-Chlorophenoxy)phenyl]-4-(4-ethoxyphenyl)-4-methylpentane
1-[3-(4-Bromophenoxy)phenyl]-4-(4-ethoxyphenyl)-4-methylpentane
1-[3-(3-Fluorophenoxy)phenyl]-4-(4-ethoxyphenyl)-4-methylpentane
1-[3-(2-Fluorophenoxy)phenyl]-4-(4-ethoxyphenyl)-4-methylpentane
1-(3-Benzoylphenyl)-4-(4-chlorophenyl)-4-methylpentane
1-(3-Benzoylphenyl)-4-(4-ethoxyphenyl)-4-methylpentane
1-(3-Benzoylphenyl)-4-(4-chlorophenyl)-4-methylhexane
1-[3-(4-Fluorophenoxy)phenyl]-4-(3-trifluoromethylphenyl)-4-methylpentane
1-[3-(3-Fluorophenylthio)phenyl]-4-(3-methylphenyl)-4-methylpentane
1-(3-Phenoxyphenyl)-4-(4-methylthiophenyl)-4-methylpentane
1-(3-Phenoxyphenyl)-4-(4-methylthiophenyl)-4-methylhexane
1-(3-Phenoxyphenyl)-4-(4-pentafluoroethoxyphenyl)-4-methylpentane
1-(3-Phenoxyphenyl)-4-(3,4-difluoromethylenedioxyphenyl)-4-methylpentane
1-[3-(4-Fluorophenoxy)phenyl]-4-(4-pentafluoroethoxyphenyl)-4-methylpentane
1-[3-(3-Chlorophenoxy)phenyl]-4-(4-difluoromethoxyphenyl)-4-methylpentane
1-[3-(3-Chlorophenoxy)phenyl]-4-(4-difluoromethoxyphenyl)-4-methylhexane
1-[3-(3-Methyl-4-chlorophenoxy)phenyl]-4-(4-allylphenyl)-4-methylpentane
1-[3-(3,5-Dichlorophenoxy)phenyl]-4-(4-tertbutylphenyl)-4-methylpentane
1-[3-(4-Chlorophenoxy)phenyl]-4-(3-chloro-4-fluorophenyl)-4-methylpentane
1-[3-(3-Methylphenoxy)phenyl]-4-(4-chlorophenyl)-4-methylpentane
1-[3-(4-Methoxyphenoxy)phenyl]-4-(4-methoxyphenyl)-4-methylpentane
1-[3-(4-Fluorobenzyl)phenyl]-4-(4-chlorophenyl)-4-methylpentane
1-[3-(3,4-Dichlorophenoxy)phenyl]-4-(4-isobutyrylphenyl)-4-methylpentane
1-[3-(4-Fluorophenoxy)phenyl]-4-phenyl-4-methylpentane
1-[3-(4-Fluorophenoxy)phenyl]-4-phenyl-4-methylpentane
1-[3-(3-Chlorophenoxy)phenyl]-4-(3-methylphenyl)-4-methylpentane
1-[3-(4-Bromophenoxy)phenyl]-4-(4-difluoromethoxyphenyl)-4-methylpentane
1-[3-(4-Bromophenoxy)phenyl]-4-(4-difluoromethoxyphenyl)-4-methylhexane
1-[3-(4-Fluorophenoxy)phenyl]-4-(4-tert-butylphenyl)-4-methylpentane
1-(3-Phenoxyphenyl)-4-(2-naphthyl)-4-methylpentane
1-[3-(4-Fluorophenoxy)phenyl]-4-(4-isopropenylphenyl)-4-methylpentane 1-(3-Phenoxyphenyl)-4-(2-naphthyl)-4-methylhexane
1-[3-(4-Fluorophenoxy)phenyl]-4-(4-methoxyphenyl)-4-methylpentane
1-[3-(4-Fluorophenoxy)phenyl]-4-(4-chloro-3-methylphenyl)-4-methylpentane
1-(3-Phenoxyphenyl)-4-[3,4-di(trifluoromethoxy)phenyl]-4-methylpentane
1-(3-Phenoxyphenyl)-4-(3,5-dimethyl-4-methyoxyphenyl)-4-methylpentane
1-[3-(4-Bromophenoxy)phenyl]-4-(4-methylphenyl)-4-methylpentane
1-(3-Phenoxyphenyl)-4-[4-(2,2-dichlorovinyloxy)phenyl]-4-methylpentane
1-[3-(4-Methoxyphenoxy)phenyl]-4-(4-chlorophenyl)-4-methylpentane
1-[3-(4-Fluorophenylthio)phenyl]-4-(4-chlorophenyl)-4-methylpentane
1-(3-Phenoxyphenyl)-4-[4-(1,1,2,2-tetrafluoroethoxy)phenyl]-4-methylpentane
1-[3-(4-Fluorophenoxy)phenyl]-4-(3-methylphenyl)-4-methylpentane
1-(3-Phenoxyphenyl)-4-(4-chlorophenyl)-4-methylhexane
1-(3-Phenoxyphenyl)-4-(3,4-dichlorophenyl)-4-methylpentane
1-(3-Phenoxyphenyl)-4-(3,4-dichlorophenyl)-4-methylhexane
1-(3-Phenoxyphenyl)-4-(3-bromo-4-chlorophenyl)-4-methylhexane
1-(3-Phenoxyphenyl)-4-[4-(2,2,2-trifluoroethoxy)phenyl]-4-methylpentane
1-(3-Phenoxyphenyl)-4-[4-(2,2,2-trifluoroethoxy)phenyl]-4-methylhexane
1-(3-Phenoxyphenyl)-4-[4-(2,2-dichloro-1,1-difluoroethoxy)phenyl]-4-methylpentane
1-(3-Phenylthiophenyl)-4-(4-ethoxyphenyl)-4-methylpentane
1-(3-Phenoxyphenyl)-4-(3-trifluoromethylphenyl)-4-methylpentane
1-(3-Phenoxyphenyl)-4-(3-chloro-4-methoxyphenyl)-4-methylpentane
1-[3-(4-Methoxyphenoxy)phenyl]-4-(4-bromophenyl)-4-methylpentane
1-[3-(4-Methoxyphenoxy)phenyl]-4-(3,4-dichlorophenyl)-4-methylpentane
1-(3-Phenoxyphenyl)-4-(6-methyl-2-naphthyl)-4-methylpentane
1-[3-(4-Fluorophenoxy)phenyl]-4-(3-bromo-4-chlorophenyl)-4-methylpentane
1-(3-Phenoxyphenyl)-4-[4-(2,2-dichlorovinyl)phenyl]-4-methylpentane
1-[3-(4-Bromophenoxy)phenyl]-4-(3-trifluoromethylphenyl)-4-methylpentane
1-(3-Phenoxyphenyl)-4-(4-nitrophenyl)-4-methylpentane
1-(3-Phenoxyphenyl)-4-(4-nitrophenyl)-4-methylhexane
1-[3-(4-Fluorophenoxy)phenyl]-4-(3-fluoro-4-methylphenyl)-4-methylpentane
1-[3-(4-Methoxyphenoxy)phenyl]-4-(4-methylphenyl)-4-methylpentane
1-[3-(4-Fluorophenoxy)phenyl]-4-(3,4-diethylphenyl)-4-methylpentane
1-(3-Phenoxyphenyl)-4-(4-dichlorofluoromethoxyphenyl)-4-methylpentane
1-(3-Phenoxyphenyl)-4-(4-methylphenyl)-4-methylpentane
1-(3-Phenoxyphenyl)-4-(4-bromophenyl)-4-methylpentane
1-(3-Phenoxyphenyl)-4-(3-chloro-4-methylphenyl)-4-methylpentane
1-(3-Phenoxyphenyl)-4-(3,4-dibromophenyl)-4-methylpentane
1-(3-Phenoxyphenyl)-4-(4-tert-butylphenyl)-4-methylpentane
1-(3-Phenoxyphenyl)-4-(4-fluorophenyl)-4-methylpentane
1-(3-Phenoxyphenyl)-4-(4-ethylphenyl)-4-methylpentane
1-(3-Phenoxyphenyl)-4-(4-chloro-3-methylphenyl)-4-methylpentane
1-(3-Phenoxyphenyl)-4-(4-tert-butylphenyl)-4-methylhexane
1-(3-Phenoxyphenyl)-4-(3,4-dimethylphenyl)-4-methylpentane
1-(3-Phenoxyphenyl)-4-(3-chloro-4-methylphenyl)-4-methylhexane
1-(3-Phenoxyphenyl)-4-(4-methylphenyl)-4-methylhexane
1-(3-Phenoxyphenyl)-4-(3-chloro-4-fluorophenyl)-4-methylpentane
1-(3-Phenoxyphenyl)-4-(3,4-difluorophenyl)-4-methylpentane
1-(3-Phenoxyphenyl)-4-(3-bromo-4-fluorophenyl)-4-methylpentane
1-(3-Phenoxyphenyl)-4-(4-bromo-3-chlorophenyl)-4-methylpentane
1-(3-Phenoxyphenyl)-4-(3-fluoro-4-methylphenyl)-4-methylpentane
1-(3-Phenoxyphenyl)-4-(3-bromo-4-methylphenyl)-4-methylpentane
1-(3-Phenoxyphenyl)-4-(3,4-diethylphenyl)-4-methylpentane
1-(3-Phenoxyphenyl)-4-(4-isopropylphenyl)-4-methylpentane
1-(3-Phenoxyphenyl)-4-(4-isopropylphenyl)-4-methylhexane
1-(3-Phenoxyphenyl)-4-(3,4-diisopropylphenyl)-4-methylpentane
1-(3-Phenoxyphenyl)-4-(3,4-di-tert-butylphenyl)-4-methylpentane
1-(3-Phenoxyphenyl)-4-(3-ethyl-4-methylphenyl)-4-methylpentane
1-(3-Phenoxyphenyl)-4-(3-methyl-4-tert-butylphenyl)-4-methylpentane
1-(3-Phenoxyphenyl)-4-(4-cyanophenyl)-4-methylpentane
1-(3-Phenoxyphenyl)-4-(3,5-dichlorophenyl)-4-methylpentane
1-(3-Phenoxyphenyl)-4-(4-n-propoxyphenyl)-4-methylpentane
1-(3-Phenoxyphenyl)-4-(4-n-propoxyphenyl)-4-methylhexane
1-[3-(4-Fluorophenoxy)phenyl]-4-(3-chloro-4-fluorophenyl)-4-methylpentane
1-(3-Phenoxyphenyl)-4-(4-isopropoxyphenyl)-4-methylpentane
1-(3-Phenoxyphenyl)-4-(4-isopropoxyphenyl-4-methylhexane
1-(3-Phenoxyphenyl)-4-(4-acetylphenyl)-4-methylpentane
1-(3-Phenoxyphenyl)-4-(4-cyclopentyloxyphenyl)-4-methylpentane
1-(3-Phenoxyphenyl)-4-(4-cyclopentyloxyphenyl)-4-methylhexane
1-(3-Phenoxyphenyl)-4-(4-n-pentyloxyphenyl)-4-methylpentane 1-(3-Phenoxyphenyl)-4-(4-n-pentyloxyphenyl)-4-methylhexane
1-(3-Phenoxyphenyl)-4-(4-isobutyloxyphenyl)-4-methylpentane
1-(3-Phenoxyphenyl)-4-(4-iodophenyl)-4-methylpentane
1-(3-Phenoxyphenyl)-4-(4-iodophenyl)-4-methylhexane
1-(3-Phenoxyphenyl)-4-(4-vinyloxyphenyl)-4-methylpentane
1-(3-Phenoxyphenyl)-4-(4-biphenyl)-4-methylpentane
1-(3-Phenoxyphenyl)-4-(4-n-butoxyphenyl)-4-methylpentane
1-(3-Phenoxyphenyl)-4-[4-(1-methylpropoxy)phenyl]-4-methylpentane
1-(3-Phenoxyphenyl)-4-(4-phenoxyphenyl)-4-methylpentane
1-(3-Phenoxyphenyl)-4-(4-phenoxyphenyl)-4-methylhexane
1-(3-Phenoxyphenyl)-4-(4-cyclohexyloxy)-4-methylpentane
1-(3-Phenoxyphenyl)-4-[4-(1,1-difluoro-2-iodoethoxy)phenyl]-4-methylpentane
1-[3-(4-Fluorophenoxy)phenyl]-4-(4-isopropylphenyl)-4-methylpentane
1-(3-Phenoxyphenyl)-4-(3-chloro-4-ethoxyphenyl)-4-methylpentane
1-(3-Phenoxyphenyl)-4-(3-chloro-4-ethoxyphenyl)-4-methylhexane
1-(3-Phenoxyphenyl)-4-[4-(1,1-difluoroethoxy)phenyl]-4-methylpentane
1-(3-Phenoxyphenyl)-4-(4-methoxymethylphenyl)-4-methylpentane
1-(3-Phenoxyphenyl)-4-(4-ethoxymethoxyphenyl)-4-methylpentane
1-(3-Phenoxyphenyl)-4-(4-ethoxymethylphenyl)-4-methylpentane
1-(3-Phenoxyphenyl)-4-(4-methoxymethoxyphenyl)-4-methylpentane
1-(3-Phenoxyphenyl)-4-[4-(1-ethoxyethyl)phenyl]-4-methylpentane
1-(3-Phenoxyphenyl)-4-(4-ethoxycarbonylphenyl)-4-methylpentane
1-(3-Phenoxyphenyl)-4-[4-(1-methoxyethyl)phenyl]-4-methylpentane
1-(3-Phenoxyphenyl)-4-(4-isopropenylphenyl)-4-methylpentane
1-(3-Phenoxyphenyl)-4-[4-(2-ethoxyethoxy)phenyl]-4-methylpentane
1-(3-Phenoxyphenyl)-4-(4-ethoxy-3-methylphenyl)-4-methylpentane
1-(3-Phenoxyphenyl)-4-(4-ethoxy-3-methylphenyl)-4-methylhexane
1-(3-Phenoxyphenyl)-4-[4-(2-methyl-1-propenyl)phenyl]-4-methylpentane
1-(3-Phenoxyphenyl)-4-[4-(1,2,2-trichlorovinyloxy)phenyl]-4-methylpentane
1-(3-Phenoxyphenyl)-4-[4-(2-chloro-1-fluorovinyloxy)phenyl]-4-methylpentane
1-(3-Phenoxyphenyl)-4-(3,4-diethoxyphenyl)-4-methylpentane
1-(3-Phenoxyphenyl)-4-(3,4-diethoxyphenyl)-4-methylhexane
1-[3-(4-Ethoxyphenoxy)phenyl]-4-(4-chlorophenyl)-4-methylpentane
1-[3-(4-Ethoxyphenoxy)phenyl]-4-(4l -chlorophenyl)-4-methylhexane
1-(3-Phenoxyphenyl)-4-(4-ethynylphenyl)-4-methylpentane
1-(3-Phenoxyphenyl)-4-(4-ethoxy-3,5-dimethylphenyl)-4-methylpentane
1-(3-Phenoxyphenyl)-4-(4-propargyloxyphenyl)-4-methylpentane
1-(3-Phenoxyphenyl)-4-(4-ethoxy-3-methoxyphenyl)-4-methylpentane
1-(3-Phenoxyphenyl)-4-(4-ethylthiophenyl)-4-methylpentane
1-(3-Phenoxyphenyl)-4-(4-ethylthiophenyl)-4-methylhexane
1-[3-(4-Ethoxyphenoxy)phenyl]-4-(4-ethoxyphenyl)-4-methylpentane
1-[3-(4-Ethoxyphenoxy)phenyl]-4-(4-ethoxyphenyl)-4-methylhexane
1-(3-Phenoxyphenyl)-4-[4-(1-chlorovinyl)phenyl]-4-methylpentane
-(3-Phenoxyphenyl)-4-(4-vinylphenyl)-4-methylpentane
1-(3-Phenoxyphenyl)-4-[4-(2,2,2-trifluoroethoxycarbonyl)phenyl]-4-methylpentane
1-(3-Phenoxyphenyl)-4-(2-chloroethoxyphenyl)-4-methylpentane
1-(3-Phenoxyphenyl)-4-[4-(1-ethylvinyl)phenyl]-4-methylpentane
1-(3-Phenoxyphenyl)-4-[4-(1-methyl-1-propenyl)phenyl]-4-methylpentane
-(3-Phenoxyphenyl)-4-(3-ethoxyphenyl)-4-methylpentane
1-[4-(4-Chlorophenoxy)phenyl]-4-(3-ethoxyphenyl)-4-methylpentane
1-[3-(4-Bromophenoxy)phenyl]-4-(3-ethoxyphenyl)-4-methylpentane
1-(3-Phenoxyphenyl)-4-(4-isopropylthiophenyl)-4-methylpentane
1-(3-Phenoxyphenyl)-4-[4-(1-methoxyiminoethyl)phenyl]-4-methylpentane
1-[3-(4-Isopropoxyphenoxy)phenyl]-4-(4-chlorophenyl)-4-methylpentane
1-(3-Phenoxyphenyl)-4-(4-allyloxyphenyl)-4-methylpentane
1-(3-Phenoxyphenyl)-4-[4-(2-methylallyloxy)phenyl]-4-methylpentane
1-(3-Phenoxyphenyl)-4-[4-(3-methyl-2-buten-1-yl)phenyl]-4-methylpentane
1-(3-Phenoxyphenyl)-4-[4-(2,3-dichloroallyloxy)phenyl]-4-methylpentane
1-(3-Phenoxyphenyl)-4-[4-(2,2-dichlorovinyloxy)phenyl]-4-methylpentane
1-(3-Phenoxyphenyl)-4-[4-(1-fluoro-2-iodoethyl)phenyl]-4-methylpentane
1-(3-Phenoxyphenyl)-4-[4-(2,2-dicyanovinyl)phenyl]-4-methylpentane
1-(3-Phenoxyphenyl)-4-(4-cyanomethoxyphenyl)-4-methylpentane
1-(3-Phenoxyphenyl)-4-(4-trimethylsilyloxyphenyl)-4-methylpentane
1-(3-Phenoxyphenyl)-4-(4-methoxymethylthiophenyl)-4-methylpentane
1-(3-Phenoxyphenyl)-4-[4-(2-fluoroethoxy)phenyl]-4-methylpentane
1-(3-Phenoxyphenyl)-4-[4-(3-tetrahydrofuryloxy)phenyl]-4-methylpentane
1-(3-Phenoxyphenyl)-4-(4-ethoxyphenyl)-pentane
1-(3-Phenoxyphenyl)-4-(4-chlorophenyl)-pentane
1-(3-Phenoxyphenyl)-4-[4-(1,1,2,2-tetrafluoroethoxy)phenyl]-4-methylhexane
1-[3-(4-Nitrophenoxy)phenyl]-4-(4-chlorophenyl)-4-methylpentane 1-(3-Phenoxyphenyl)-4-[4-(2-chloro-1,1-difluoroethoxy)phenyl]-4-methylpentane
1-(3-Phenoxyphenyl)-4-[4-(2,2-dichloro-1,1-difluoroethoxy)phenyl]-4-methylpentane
1-(3-Phenoxyphenyl)-4-[4-(2,2,-dichloro-1-fluoroethoxy)phenyl]-4-methylpentane
1-(3,4,5,6-Tetrahydrophthalimido)-4-(4-ethoxyphenyl)-4-methylpentane
1-(3-Benzoylphenyl)-4-(3-bromo-4-ethoxyphenyl)-4-methylpentane
1-(3-Benzylphenyl)-4-(4-chlorophenyl)-4-methylpentane
1-(3-Benzylphenyl)-4-(4-ethoxyphenyl)-4-methylpentane
1-(3-Phenoxyphenyl)-4-(4-chlorophenyl)-5-methylhexane
1-(3-Phenoxyphenyl)-4-(4-ethoxyphenyl)-5-methylhexane
1-(3-Phenoxyphenyl)-4-(4-difluoromethoxyphenyl)-5-methylhexane
1-(6-Phenoxy-2-pyridyl)-4-(4-ethoxyphenyl)-4-methylpentane
1-(6-Phenoxy-2-pyridyl)-4-(4-chlorophenyl)-4-methylpentane
1-(6-Phenoxy-2-pyridyl)-4-(4-difluoromethoxyphenyl)-4-methylpentane
1-(3-Phenoxyphenyl)-4-(3-chlorophenyl)-4-methylpentane
1-(3-Phenoxyphenyl)-3-[1-(4-ethoxyphenyl)cyclobutyl]propane
1-(3-Phenoxyphenyl)-4-[4-(2-chloro-1,1-difluoroethoxy)phenyl]-4-methylpentane
1-[6-(4-Fluorophenyl)-2-pyridyl]-4-(4-ethoxyphenyl)-4-methylpentane
1-(3-Phenoxyphenyl)-4-(4-chlorophenyl)-4,5-dimethylhexane
1-(3-Phenoxyphenyl)-3-[1-(4-chlorophenyl)-2,2-dichlorocyclopropyl]-propane
1-(3-Phenoxyphenyl)-3-[1-(4-chlorophenyl)cyclopropyl]-propane
1-(3-Phenoxyphenyl)-3-[1-(4-ethoxyphenyl)cyclopropyl]-propane
1-(3-Phenoxyphenyl)-3-[1-(4-ethoxyphenyl)cyclopentyl]-propane
1-(3-Phenoxyphenyl)-3-[1-(4-ethoxyphenyl)cyclohexyl]-propane
1-[4-(2-Allyl-3-methylcyclopenten-1-on)-yl]-3-(4-ethoxyphenyl)-3-methylbutane
1-(5-Propargyl-2-methyl-3-furyl)-4-(4-ethoxyphenyl)-4-methylpentane
1-[4-(2-Allyl-3-methylcyclopenten-1-on)-yl]-3-(4-chlorophenyl)-3-methylbutane
1-(5-Propargyl-2-methyl-3-furyl)-4-(4-chlorophenyl)-4-methylpentane
1-[3-(4-Fluorophenoxy)-4-fluorophenyl]-4-(4-chlorophenyl)-4-methylpentane
1-[3-(4-Fluorophenoxy)-4-fluorophenyl]-4-(4-chlorophenyl)-4-methylhexane
1-(3-Phenoxy-4-fluorophenyl)-4-phenyl-4-methylpentane
1-(3-Phenoxy-4-chlorophenyl)-4-(4-chlorophenyl)-4-methylpentane
1-(3-Phenoxy-4-fluorophenyl)-4-(4-methoxyphenyl)-4-methylpentane
1-(3-Phenoxy-4-fluorophenyl)-4-(4-chlorophenyl)-pentane
1-(3-Phenoxy-4-fluorophenyl)-4-(4-chlorophenyl)-4,5-dimethylhexane
1-(3-Phenoxy-4-fluorophenyl)-4-(3,4-dimethoxyphenyl)-4-methylpentane
1-(3-Phenoxy-4-fluorophenyl)-4-(4-ethoxymethylphenyl)-4-methylpentane
1-(3-Phenoxy-4-fluorophenyl)-4-(4-methoxymethoxyphenyl)-4-methylpentane
1-(3-Phenoxy-4-fluorophenyl)-4-[4-(1-ethoxyethyl)phenyl]-4-methylpentane
1-(3-Phenoxy-4-fluorophenyl)-4-(4-ethoxycarbonylphenyl)-4-methylpentane
1-(3-Phenoxy-4-fluorophenyl)-4-[4-(1-methoxyethyl)phenyl]-4-methylpentane
1-(3-Phenoxy-4-fluorophenyl)-4-[4-(2-ethoxyethoxy)phenyl]-4-methylpentane
1-(3-Phenoxy-4-fluorophenyl)-4-(4-ethoxy-3-methylphenyl)-4-methylpentane
1-(3-Phenoxy-4-fluorophenyl)-4-[4-(2-methyl-1-propenyl)phenyl]-4-methylepentane
1-(3-Phenoxy-4-fluorophenyl)-4-[4-(1,2,2-trichlorovinyloxy)phenyl]-4-methylpentane
1-(3-Phenoxy-4-fluorophenyl)-4-(3,4-diethoxyphenyl)-4-methylpentane
1-(3-Phenoxy-4-fluorophenyl)-4-(4-ethynylphenyl)-4-methylpentane
1-(3-Phenoxy-4-fluorophenyl)-4-(4-ethoxy-3,5-dimethylphenyl)-4-methylpentane
1-(3-Phenoxy-4-fluorophenyl)-4-(3,4-dimethylphenyl)-4-methylpentane
1-[3-(4-Fluorophenoxy)-4-fluorophenyl]-4-(4-methoxyphenyl)-4-methylpentane
1-(3-Phenoxy-4-fluorophenyl)-4-(4-chlorophenyl)hexane
1-(3-Phenoxy-6-chlorophenyl)-4-(4-chlorophenyl)-4-methylpentane
1-(3-Phenoxy-4-fluorophenyl)-4-(4-chlorophenyl)-5-methylhexane
1-[3-(4-Fluorophenoxy)-4-fluorophenyl]-4-(3,4-dichlorophenyl)-4-methylhexane
1-(3-Phenoxy-5-methoxyphenyl)-4-(4-chlorophenyl)-4-methylpentane
1-[3-(3-Chlorophenoxy)-4-fluorophenyl]-4-(4-chlorophenyl)-4-methylpentane
1-[3-(3-Chlorophenoxy)-4-fluorophenyl]-4-(3,4-dimethylphenyl)-4-methylhexane
1-(3-Phenoxy-4-fluorophenyl)-4-(4-chlorophenyl)-4-methylpentane
1-[3-(2-Fluorophenoxy)-4-fluorophenyl]-4-(3-chloro-4-fluorophenyl)-4-methylpentane
1-[3-(2-Fluorophenoxy)-4-fluorophenyl]-4-(4-chlorophenyl)-4-methylpentane
1-[3-(2-Fluorophenoxy)-4-fluorophenyl]-4-(4-ethoxyphenyl)-4-methylpentane
1-(3-Phenoxy-4-fluorophenyl)-4-(2-naphthyl)-4-methylpentane
1-(3-Phenoxy-4-fluorophenyl)-4-(4-methoxy-3,5-dimethylphenyl)-4-methylpentane
1-(3-Phenoxy-4-fluorophenyl)-4-(4-tert-butylphenyl)-4-methylpentane
1-[3-(4-Methoxyphenoxy)-4-fluorophenyl]-4-(4-chlorophenyl)-4-methylpentane
1-(3-Phenoxy-4-fluorophenyl)-4-(3,4-dimethylphenyl)-4-methylpentane
1-[3-(4-Bromophenoxy)-4-fluorophenyl]-4-(4-ethoxyphenyl)-4-methylpentane
1-(3-Phenoxy-4-fluorophenyl)-4-(4-isopropenylphenyl)-hexane
1-(3-Phenoxy-4-fluorophenoxy)-4-(3-trifluoromethylphenyl)-4-methylpentane 1-(3-Phenoxy-4-fluorophenyl)-4-(4-bromophenyl)-4-methylpentane
1-(3-Phenoxy-4-methylphenyl)-4-(4-chlorophenyl)-4-methylpentane
1-(3-Phenoxy-4-fluorophenyl)-4-(3-methylphenyl)-4-methylpentane
1-(3-Phenoxy-5-fluorophenyl)-4-(3,4-diethylphenyl)-4-methylpentane
1-(3-Phenoxy-4-fluorophenyl)-4-[(1,2,3,4-tetrahydronaphthalen)-7-yl]-4-methylpentane
1-(3-Phenoxy-4-fluorophenyl)-4-(indan-5-yl)-4-methylpentane
1-[3-(3-Fluorophenoxy)-4-fluorophenyl]-4-(4-methoxy-3-methylphenyl)-4-methylpentane
1-(3-Phenoxy-4-fluorophenyl)-4-(3-bromo-4-ethoxyphenyl)-4-methylpentane
1-(3-Phenoxy-4-fluorophenyl)-4-(4-chlorophenyl)-4-methylhexane
1-(3-Phenoxy-4-fluorophenyl)-4-(3,4-methylendioxphenyl)-4-methylpentane
1-(3-Phenoxy-4-fluorophenyl)-4-(4-difluoromethoxyphenyl)-4-methylpentane
1-(3-Phenoxy-4-fluorophenyl)-4-(4-difluoromethoxyphenyl)-4-methylhexane
1-[3-(3-Methylphenoxy)-4-fluorophenyl]-4-(4-chlorophenyl)-4-methylpentane
1-[3-(3-Chlorophenoxy)-5-fluorophenyl]-4-(3,4-dimethyl-5-nitrophenyl)-4-methylpentane
1-[3-(2-Fluorophenoxy)-4-fluorophenyl]-4-(4-methylthiophenyl)-4-methylpentane
1-[3-(3-Fluorophenoxy)-5-fluorophenyl]-4-(3-chloro-4-methoxyphenyl)-4-methylpentane
1-(3-Phenoxy-6-bromophenyl)-4-(4-methylphenyl)-4-methylpentane
1-[3-(4-Fluorophenoxy)-4-fluorophenyl]-4-(3,4-dichlorophenyl)-4-methylpentane
1-[3-(4-Methylphenoxy)-5-fluorophenyl]-4-(4-methylsulfinylphenyl)-4-methylpentane
1-(3-Phenoxy-2-fluorophenyl)-4-phenyl-4-methylpentane
1-(3-Phenoxy-4-fluorophenyl)-4-(4-chlorophenyl)-4,5-dimethylhexane
1-(3-Phenoxy-6-bromophenyl)-4-(4-chlorophenyl)-4-methylpentane
1-[3-(4-Fluorophenoxy)-2-fluorophenyl]-4-phenyl-4-methylpentane
1-(3-Phenoxy-4-fluorophenyl)-4-(4-methylthiophenyl)-4-methylpentane
1-(3-Phenoxy-4-fluorophenyl)-4-(4-methylphenyl)-4-methylpentane
1-[3-(4-Fluorophenoxy)-5-fluorophenyl]-4-(4-chlorophenyl)-4-methylpentane
1-(3-Phenoxy-4-fluorophenyl)-4-(4-fluorophenyl)-4-methylpentane
1-(3-Phenoxy-5-fluorophenyl)-4-(4-chlorophenyl)-4-methylpentane
1-(3-Phenoxy-2-fluorophenyl)-4-(4-trifluoromethylphenyl)-4-methylpentane
1-(3-Phenoxy-4-fluorophenyl)-4-(4-nitrophenyl)-4-methylpentane
1-(3-Phenoxy-5-fluorophenyl)-4-(4-chlorophenyl)-4-methylpentane
1-(3-Phenoxy-6-chlorophenyl)-4-(4-methylphenyl)-4-methylpentane
1-(3-Phenoxy-4-fluorophenyl)-4-(3,4-methylenedioxyphenyl)-4-methylhexane
1-[3-(3-Chlorophenoxy)-4-fluorophenyl]-4-(4-chlorophenyl)-hexane
1-(3-Phenoxy-6-fluorophenyl)-4-(4-chlorophenyl)-4-methylpentane
1-(3-Phenoxy-4-fluorophenyl)-4-(3-chloro-4-methylphenyl)-4-methylpentane
1-(3-Phenoxy-4-fluorophenyl)-4-(4-trifluoromethylthiophenyl)-4-methylpentane
1-(3-Phenoxy-4-fluorophenyl)-4-(4-difluoromethoxyphenyl)-hexane
1-(3-Phenoxy-4-fluorophenyl)-4-(4-cyanophenyl)-4-methylpentane
1-(3-Phenoxy-4-fluorophenyl)-4-(3,4-difluorophenyl)-4-methylpentane
1-(3-Phenoxy-4-fluorophenyl)-4-(4-ethoxyphenyl)-4-methylpentane
1-(3-Phenoxy-4-fluorophenyl)-4-(3,4-dibromophenyl)-4-methylpentane
1-(3-Phenoxy-4-fluorophenyl)-4-(4-trifluoromethoxyphenyl)-4-methylpentane
1-(3-Phenoxy-4-fluorophenyl)-4-(4-ethylphenyl)-4-methylpentane
1-(3-Phenoxy-4-fluorophenyl)-4-(4-isopropylphenyl)-4-methylpentane
1-(3-Phenoxy-4-fluorophenyl)-4-(4-ethoxyphenyl)-hexane
1-(3-Phenoxy-4-fluorophenyl)-4-(4-pentafluoroethoxyphenyl)-4-methylpentane
1-(3-Phenoxy-4-fluorophenyl)-4-(4-difluoromethoxyphenyl)-4,5-dimethylhexane
1-(3-Phenoxy-4-fluorophenyl)-4-(4-ethoxyphenyl)-4-methylhexane
1-(3-Phenoxy-4-fluorophenyl)-4-(4-allylphenyl)-4-methylpentane
1-(3-Phenoxy-4-fluorophenyl)-4-(4-methoxymethylphenyl)-4-methylpentane
1-(3-Phenoxy-5-chlorophenyl)-4-(4-methylphenyl)-4-methylpentane
1-(3-Phenoxy-4-fluorophenyl)-4-(4-isobutyrylphenyl)-4-methylpentane
1-(3-Phenoxy-4-fluorophenyl)-4-(3,5-dichlorophenyl)-4-methylpentane
1-(3-Phenoxy-4-fluorophenyl)-4-(3,4-di-tertbutylphenyl)-4-methylpentane
1-(3-Phenoxy-4-fluorophenyl)-4-(4-difluoromethoxyphenyl)-4-methylhexane
1-(3-Phenoxy-4-fluorophenyl)-4-[3,4-bis(trifluoromethoxy)phenyl]-4-methylpentane
1-(3-Phenoxy-4-fluorophenyl)-4-(4-methoxy-3,5-dimethylphenyl)-4-methylpentane
1-(3-Phenoxy-4-fluorophenyl)-4-[4-(2,2-dichlorovinyloxy)phenyl]-4-methylpentane
1-(3-Phenoxy-4-fluorophenyl)-4-(4-ethoxyphenyl)-4,5-dimethylhexane
1-(3-Phenoxy-4-fluorophenyl)-4-[4-(1,1,2,2-tetrafluoroethoxy)phenyl]-4-methylpentane
1-(3-Phenoxy-4-fluorophenyl)-4-(3-bromo-4-chlorophenyl)-4-methylpentane
1-(3-Phenoxy-4-fluorophenyl)-4-[4-(2,2,2-trifluoroethoxy)phenyl]-4-methylpentane
1-(3-Phenoxy-4-fluorophenyl)-4-(6-methylnaphthalen-2-yl)-4-methylpentane
1-(3-Phenoxy-4-fluorophenyl)-4-[4-(2,2-dichlorovinyl)phenyl]-4-methylpentane
1-(3-Phenoxy-4-fluorophenyl)-4-(3-fluoro-4-methylphenyl)-4-methylpentane
1-(3-Phenoxy-4-fluorophenyl)-4-(4-dichlorofluoromethoxyphenyl)-4-methylpentane
1-(3-Phenoxy-4-fluorophenyl)-4-(4-difluoromethoxyphenyl)-5-methylhexane 1-(3-Phenoxy-4-fluorophenyl)-4-(3-chloro-4-methylphenyl)-4-methylpentane
1-(3-Phenoxy-4-fluorophenyl)-4-(3-bromo-4-fluorophenyl)-4-methylpentane
1-(3-Phenoxy-4-fluorophenyl)-4-(3-fluoro-4-methylphenyl)-4-methylpentane
1-(3-Phenoxy-4-fluorophenyl)-4-(4-ethoxyphenyl)-5-methylhexane
1-(3-Phenoxy-4-fluorophenyl)-4-(3-bromo-4-methylphenyl)-4-methylpentane
1-(3-Phenoxy-4-fluorophenyl)-4-(4-isopropylphenyl)-4-methylpentane
1-(3-Phenoxy-4-fluorophenyl)-4-(3,4-diisopropylphenyl)-4-methylpentane
1-(3-Phenoxy-4-fluorophenyl)-4-(3-ethyl-4-methylphenyl)-4-methylpentane
1-(3-Phenoxy-4-fluorophenyl)-4-(4-tert-butyl-3-methylphenyl)-4-methylpentane
1-(3-Phenoxy-4-fluorophenyl)-4-(4-n-porpoxyphenyl)-4-methylpentane
1-(3-Phenoxy-4-fluorophenyl)-4-(4-n-propoxyphenyl)-4-methylhexane
1-(3-Phenoxy-4-fluorophenyl)-4-(4-isopropoxyphenyl)-4-methylpentane
1-(3-Phenoxy-4-fluorophenyl)-4-(4-isopropoxyphenyl)-4-methylhexane
1-[3-(4-Fluorophenoxy)-4-fluorophenyl]-4-(4-ethoxyphenyl)-4-methylpentane
1-(3-Phenoxy-4-fluorophenyl)-4-(4-acetylphenyl)-4-methylpentane
1-(3-Phenoxy-4-fluorophenyl)-4-(4-cyclopentyloxyphenyl)-4-methylpentane
1-(3-Phenoxy-4-fluorophenyl)-4-(4-n-pentyloxyphenyl)-4-methylpentane
1-(3-Phenoxy-4-fluorophenyl)-4-(4-isobutoxyphenyl)-4-methylpentane
1-(3-Phenoxy-4-fluorophenyl)-4-(4-iodophenyl)-4-methylpentane
1-(3-Phenoxy-4-fluorophenyl)-4-(4-iodophenyl)-4-methylhexane
1-[3-(4-Bromophenoxy)-4-fluorophenyl]-4-(4-ethoxyphenyl)-4-methylpentane
1-(3-Phenoxy-4-fluorophenyl)-4-(4-vinyloxyphenyl)-4-methylpentane
1-(3-Phenoxy-4-fluorophenyl)-4-(4-biphenyl)-4-methylpentane
1-(3-Phenoxy-4-fluorophenyl)-4-(4-n-butoxyphenyl)-4-methylpentane
1-(3-Phenoxy-4-fluorophenyl)-4-[4-(2-butoxy)phenyl]-4-methylpentane
1-(3-Phenoxy-4-fluorophenyl)-4-(4-phenoxyphenyl)-4-methylpentane
1-(3-Phenoxy-4-fluorophenyl)-4-(3-chloro-4-fluorophenyl)-4-methylpentane
1-(3-Phenoxy-4-fluorophenyl)-4-(4-cyclohexyloxyphenyl)-4-methylpentane
1-(3-Phenoxy-4-fluorophenyl)-4-[4-(1,1-difluoro-2-iodoethoxy)phenyl]-4-methylpentane
1-[3-(4-Chlorophenoxy)-4-fluorophenyl]-4-(4-ethoxyphenyl)-4-methylpentane
1-(3-Phenoxy-4-fluorophenyl)-4-(3-chloro-4-ethoxyphenyl)-4-methylpentane
1-(3-Phenoxy-4-fluorophenyl)-4-[4-(1,1-difluoroethoxy)phenyl]-4-methylpentane
1-(3-Phenoxy-4-fluorophenyl)-4-(4-methoxymethylphenyl)-4-methylpentane
1-(3-Phenoxy-4-fluorophenyl)-4-(4-ethoxymethoxyphenyl)-4-methylpentane
1-(3-Phenoxy-4-fluorophenyl)-4-(4-propargyloxyphenyl)-4-methylpentane
1-(3-Phenoxy-4-fluorophenyl)-4-(4-ethoxy-3-methoxyphenyl)-4-methylpentane
1-(3-Phenoxy-4-fluorophenyl)-4-(3-ethoxyphenyl)-4-methylpentane
1-(3-Phenoxy-4-fluorophenyl)-4-[3,4-bis(difluoroethoxy)phenyl]-4-methylpentane
1-(3-Phenoxy-4-fluorophenyl)-4-(4-ethylthiophenyl)-4-methylpentane
1-[3-(4-Ethoxyphenoxy)-4-fluorophenyl]-4-(4-ethoxyphenyl)-4-methylpentane
1-(3-Phenoxy-4-fluorophenyl)-4-[4-(2-chlorovinyl)phenyl]-4-methylpentane
1-(3-Phenoxy-4-fluorophenyl)-4-(4-vinylphenyl)-4-methylpentane
1-(3-Phenoxy-4-fluorophenyl)-4-[4-(2,2,2-trifluoroethoxycarbonyl)phenyl]-4-methylpentane
1-(3-Phenoxy-4-fluorophenyl)-4-[4-(2-chloroethoxy)phenyl]-4-methylpentane
1-(3-Phenoxy-4-fluorophenyl)-4-[4-(1-methyl-1-propenyl)phenyl]-4-methylpentane
1-(3-Phenoxy-4-fluorophenyl)-4-[4-(1-ethylvinyl)phenyl]-4-methylpentane
1-(3-Phenoxy-4-fluorophenyl)-4-(4-isopropylthiophenyl)-4-methylpentane
1-(3-Phenoxy-4-fluorophenyl)-4-(4-methoxymethylthiophenyl)-4-methylpentane
1-(3-Phenoxy-4-fluorophenyl)-4-[4-(2-fluoroethoxy)phenyl]-4-methylpentane
1-(3-Phenoxyphenyl)-1-cyano-4-(4-chlorophenyl)-4-methylpentane
1-(3-Phenoxyphenyl)-1-ethynyl-4-(4-chlorophenyl)-4-methylpentane
1-(3-Phenoxyphenyl)-1-cyano-4-(4-ethoxyphenyl)-4-methylpentane
1-(3-Phenoxyphenyl)-1-ethynyl-4-(4-ethoxyphenyl)-4-methylpentane
1-(3-Phenoxyphenyl)-1-cyano-4-(4-ethoxyphenyl)-4-methylhexane
1-(3-Phenoxyphenyl)-1-cyano-4-(4-difluoromethoxyphenyl)-4-methylpentane
1-(3-Phenoxyphenyl)-1-ethynyl-4-(4-difluoromethoxyphenyl)-4-methylpentane
1-(3-Phenoxy-4-fluorophenyl)-1-cyano-4-(4-chlorophenyl)-4-methylpentane
1-(3-Phenoxy-4-fluorophenyl)-1-ethynyl-4-(4-chlorophenyl)-4-methylpentane
1-(3-Phenoxy-4-fluorophenyl)-1-cyano-4-(4-ethoxyphenyl)-4-methylpentane
1-(3-Phenoxy-4-fluorophenyl)-1-ethynyl-4-(4-ethoxyphenyl)-4-methylpentane
1-(3-Phenylthio-4-fluorophenyl)-4-(4-ethoxyphenyl)-4-methylpentane
1-(3-Phenoxy-4-fluorophenyl)-3-[1-(4-ethoxyphenyl)cyclobutyl]propane
1-(3-Phenoxy-4-fluorophenyl)-3-[1-(4-ethoxyphenyl)cyclopropyl]propane
1-(3-Phenoxy-4-fluorophenyl)-3-[1-(4-ethoxyphenyl)cyclopentyl]propane
1-(3-Phenoxy-4-fluorophenyl)-3-[1-(4-ethoxyphenyl)cyclohexyl]propane
1-(3-Phenoxy-4-fluorophenyl)-3-[1-(4-chlorophenyl)cyclobutyl]propane
1-(3-Phenoxy-4-fluorophenyl)-3-[1-(4-chlorophenyl)cyclopropyl]propane
1-(3-Phenoxy-4-fluorophenyl)-3-[1-(4-chlorophenyl)cyclopentyl]propane 1-(3-Phenoxy-4-fluorophenyl)-3-[1-(4-chlorophenyl)cyclohexyl]propane 1-[3-(2-Pyridyloxy)phenyl]-4-(4-chlorophenyl)-4-methylpentane 1-[3-(2-Pyridyloxy)phenyl]-4-(4-ethoxyphenyl)-4-methylpentane 1-[3-(2-pyridyloxy)-4-fluorophenyl]-4-(4-ethoxyphenyl)-4-methylpentane 1-(3-Phenoxy-4-fluorophenyl)-1-cyano-3-[1-(4-ethoxyphenyl)cyclobutyl]propane The processes of the present invention are described more particularly below. Namely, when a ketone represented by the general formula (VII):

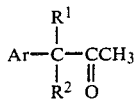

(VII)

wherein Ar, $R^1$ and $R^2$ are as defined above, and an aldehyde represented by the general formula (VIII):

$$R^{12}CHO \qquad (VIII)$$

wherein $R^{12}$ is as defined above, are allowed to condensation together, or an aldehyde represented by the general formula (X):

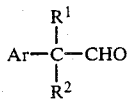

(X)

wherein Ar, $R^1$ and $R^2$ are as defined above, and a ketone represented by the general formula (XI):

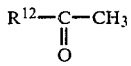

(XI)

wherein $R^{12}$ is as defined above, are allowed to condensation together, these condensation reactions are carried out in an inactive solvent or without any solvent, in the presence of an alkaline or acidic catalyzer as a condensing agent. As the condensing agent, there can be exemplified alkaline hydroxides, alkaline carbonates, alkaline alcoholates, potassium cyanide, alkaline acetates, zinc chloride and acetyl chloride together, sulfuric acid, hydrohalogenic acids, aluminum halogenides, phosphorus oxychlorides, triphenylaluminium, alumina, sodium orthophosphate, barium oxide, organoamines, salts of organoamines, amino acids, ion exchange resins, etc., and preferably basic catalyzers. As the inactive solvent, there can be exemplified water, alcohols, ethers benzene, acetic acid, etc.

Though a β-oxyketone or a β-haloketone may be obtained in certain cases in the condensation reactions of the ketone and the aldehyde above described, such a compound is subjected to dehydration or elimination of hydrogen halide to give easily an α,β-unsaturated carbonyl compound represented by the general formulas (IX) or (XII):

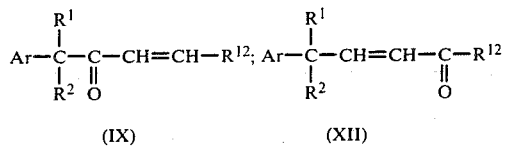

wherein Ar, $R^1$, $R^2$ and $R^{12}$ are as defined above, Though an aromatic alkane derivative represented by the general formula (I):

wherein Ar, $R^1$, $R^2$ and $R^3$ are as defined above, can be obtained directly by reducing the α,β-unsaturated carbonyl compound represented by the general formulas (IX) or (XII), the reduction under milder conditions can be carried out by employing the following route.

The α,β-unsaturated carbonyl compound represented by the general formulas (IX) or (XII) is reduced, for example, by the method described in "J. H. Brewster et al, J. Org. Chem., 29, 116 (1964)" to give the mixture of the compounds represented by the general formulas (XVIII) and (XVI):

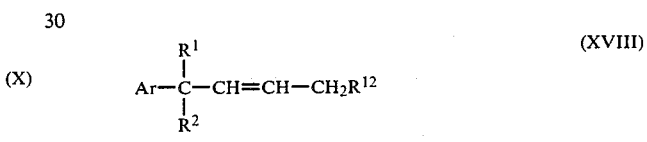

and

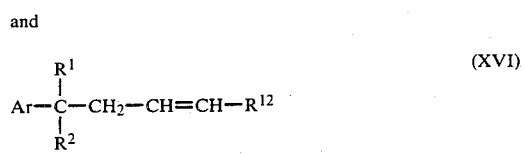

wherein Ar, $R^1$, $R^2$ and $R^{12}$ are as defined above, and further the mixture is reduced to give the aromatic alkane derivative (I) in an excellent yield.

The ketone represented by the general formulas (VII) or (XI) which is used as a starting material, can be obtained by reacting a methylmagnesium halide with the corresponding nitrile (C. R. Hauser et al, J. Org. Chem., 15, 359 (1950)), or by reacting methyllitium with the corresponding carboxylic acid.

The aldehyde represented by the general formula (X) which is used as a starting material, can be obtained by reducing the corresponding nitrile (J. Am., Chem. Soc., 86, 1085 (1964)) or acid chloride (Org. Reactions, 4, 362 (1948)) or by oxidizing the corresponding alcohol (Helvetica Chimica Acta, 54, 868 (1971)).

When the aldehyde represented by the general formula (XIII):

wherein Ar, $R^1$ and $R^2$ are as defined above, is reacted with the compound represented by the general formulas (XIV) or (XV):

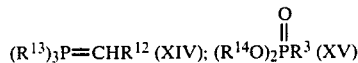

wherein $R^{12}$, $R^{13}$, $R^{14}$ and $R^3$ are as defined above, the reaction is carried out at −70° C. to 100° C. in the presence of an inactive solvent. As the inactive solvent, there can be exemplified ethers, dichloromethane, THF, DMF, DMSO, HMPA, benzene, alcohols, dimethylcellosolve, etc.

The compound represented by the general formulas (XIV) or (XV) can be obtained easily by reacting $R^{12}CHX$ or $R^3X$ ($R^{12}$ and $R^3$ are as defined above, and X stands for a halogen atom) with $(R^{13})_3P$ or $(R^{14}O)_3P$ ($R^{13}$ and $R^{14}$ are as defined below), wherein $R^{13}$ and $R^{14}$ are as defined above.

When the olefin represented by the general formula (XVI) is introduced with a cyano or ethynyl group, the olefin is added with a hydrogen halide in the usual way, and then, the resulting compound is reacted with a cyano-compound or an acetylide.

When a cyano group is introduced into the above olefin, the desired compound can be also obtained by making a cyano-compound to react directly with the olefin represented by the general formula (XVI).

When $R^4$ in the general formula (I) is a cyano group, the compound represented by the general formula (I) can be also obtained by reacting a halide represented by the general formula (XX) with a nitrile represented by the general formula (XXIII):

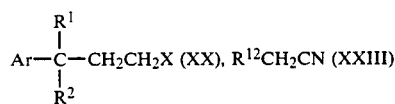

wherein Ar, $R^1$, $R^2$ and $R^{12}$ are as defined above and X stands for a halogen atom.

In the cases of the compounds represented by the general formula (I) of which the substituent of Ar is an alkoxy, haloalkoxy or haloalkenyloxy group, etc., the desired compound can also be obtained by hydrolyzing an other easily available alkoxy derivative to give the hydroxy derivative and reacting it with the corresponding halogenized compound.

The preparation routes are exemplified by using reaction formulas as follows:

(1)

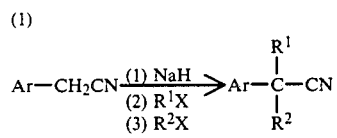

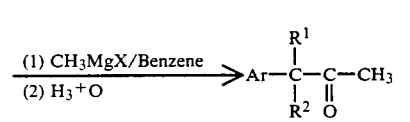

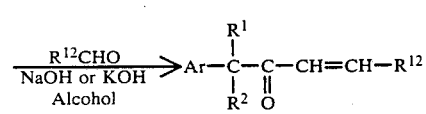

-continued

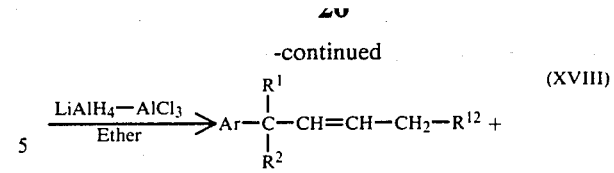

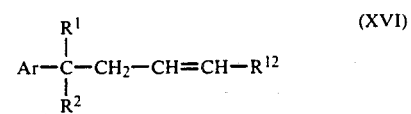

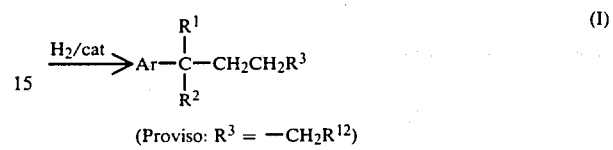

(2)

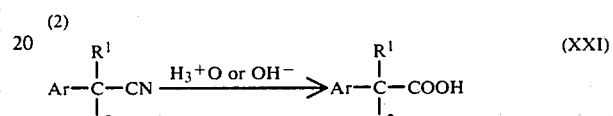

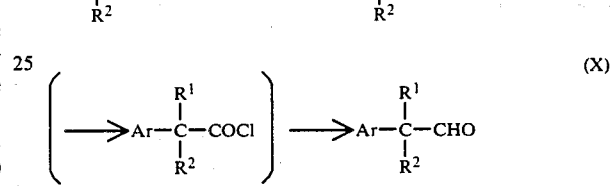

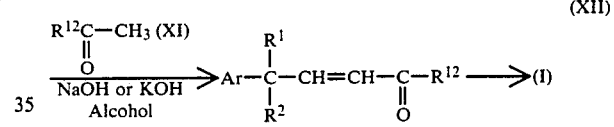

(3)

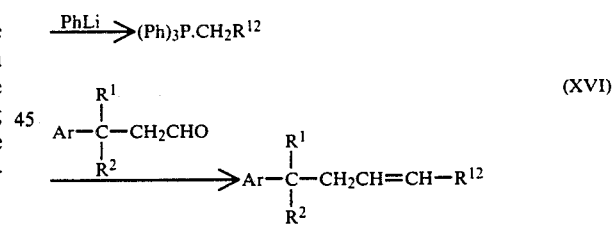

(4)

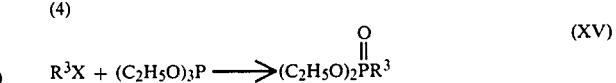

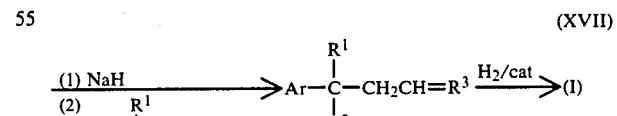

(5)

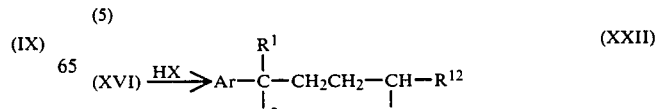

-continued

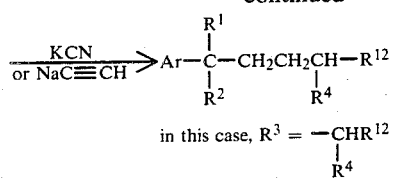

in this case, $R^3 = -CHR^{12}$
                        $|$
                        $R^4$ or

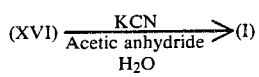 →(I)

or

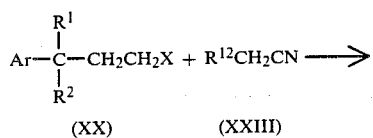

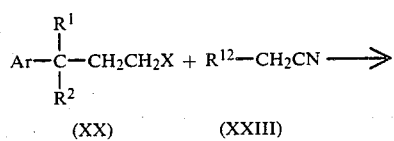

cf. Reference: Roczniki Chem., 39, 1223 (1965).
(Chemical Abstract, 64, 12595h (1966).)

(6)

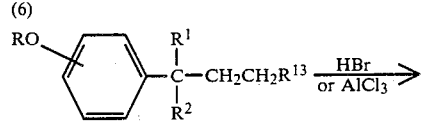

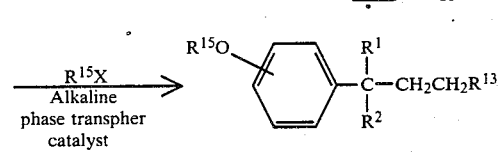

wherein $R^{15}$ stands for a substituted alkyl, alkenyl or alkynyl group, etc.

Starting materials was synthesized according to the following references.

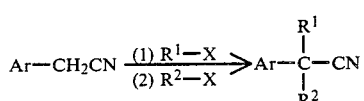  (a)

-continued

Reference: Roczniki Chem., 39, 1223 (1965).
(Chemical Abstract, 64, 12595h (1966).)
Reference: U.S. Pat. No. 4,397,864 (1983).

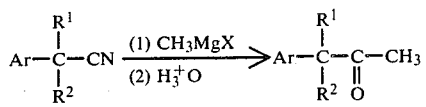 (b)

(VII)

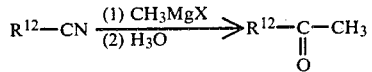

(XI)

cf. Reference: J. Org. Chem., 15, 359 (1950).

Synthesis of Compound (X)

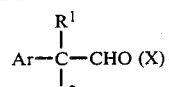 (c)

Reference: Helvetica Chimica Acta. 54, 868 (1971).

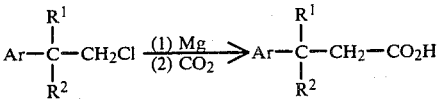 (d)

Reference: Chem. Ber., 94, 2609 (1961).

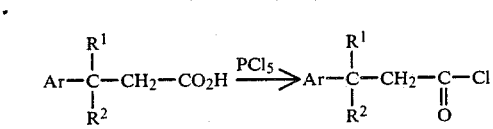

cf. Reference: Org, Syn., Coll. Vol. 1, 394 (1941).

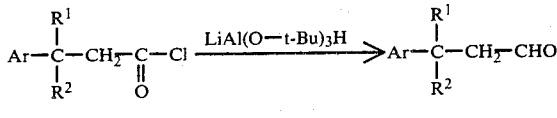

(XIII)

cf. Reference: J. Am. Chem. Soc., 80, 5372 (1958).

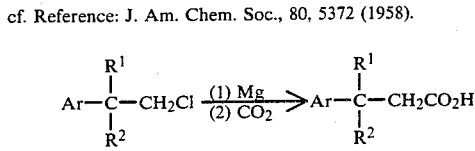 (e)

Reference: Chem. Ber., 94, 2609 (1961).

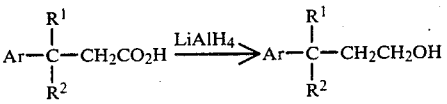

cf. Reference: J. Am. Chem. Soc., 69, 2548 (1947).

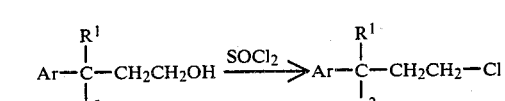

(XX)

cf. Reference: Compt. rend., 152, 1601 (1911).

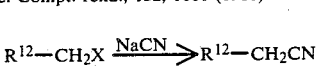 (f)

(XXIII)

cf. Reference: J. Org. Chem., 25, 877 (1960).

The processes for the preparations of the aromatic alkane derivatives of the present invention will now be described in detail with reference to the following Synthesis Examples.

SYNTHESIS EXAMPLE 1

Synthesis of 1-(3-phenoxyphenyl)-4-(4-methylphenyl)-4-methylpentane

The synthesis was carried out according to the following procedure.

(1) 1-(3-Phenoxyphenyl)-4-(4-methylphenyl)-4-methyl-2-pentene and 1-(3-phenoxyphenyl)-4-(4-methylphenyl)-4-methyl-1-pentene (a) To 50 ml of ethanol were added 5.3 g of 2-(4-methylphenyl)-2-methyl-3-butanone, 6.0 g of 3-phenoxybenzaldehyde and 6.0 g of KOH, and the mixture was stirred at room temperature for one hour and 20 minutes. Then, the reaction mixture was poured into 300 ml of water and extracted with benzene. The benzene extract was washed with water and dried, and the solvent was evaporated under reduced pressure to give 10.4 g of crude 1-(3-phenoxyphenyl)-4-(4-methylphenyl)-4-methyl-1-penten-3-one. Then, the crude product was purified by column chromatography on 250 g of silica gel (eluent:benzene) to give 6.8 g of pure 1-(3-phenoxyphenyl)-4-(4-methylphenyl)-4-methyl-1-penten-3-one.

$n_D^{20.3} 1.6121$.

$\nu_{max}^{Neat}(cm^{-1})$: 1680, 1605, 1570, 1485, 1240, 1055.

$\delta_{TMS}^{CCl_4}(ppm)$: 1.47(s, 6H), 2.32(s, 3H), 6.3~7.6 (m, 15H).

(b) To 10 ml of dry ether was added 1.4 g of lithium aluminum hydride and thereinto a solution of 9.7 g of aluminum chloride in 20 ml of ether was added dropwise with care. Then, a solution prepared by adding 7.4 g of 1-(3-phenoxyphenyl)-4-(4-methylphenyl)-4-methyl-1-penten-3-one obtained according to the above (a) to 10 ml of ether was added dropwise into the mixture, and refluxed with heating for 30 minutes. Ethyl acetate and then water were added dropwise into the reaction mixture with cooling, and the obtained mixture was extracted with benzene. The benzene extract was washed with water and dried, and the solvent was evaporated under reduced pressure. The residue was purified by column chromatography on 150 g of silica gel (1:2 mixed solvent of benzene and hexane was used as eluent) to give 3.6 g of a mixture of 50% 1-(3-phenoxyphenyl)-4-(4-methylphenyl)-4-methyl-2-pentene and 50% 1-(3-phenoxyphenyl)-4-(4-methylphenyl)-4-methyl-1-pentene.

$n_D^{20.2} 1.5882$.

$\nu_{max}^{Neat}(cm^{-1})$: 1590, 1500, 1495, 1455, 1255, 1225, 980, 825, 700.

$\delta_{TMS}^{CCl_4}(ppm)$: 1.32(s, 6H×½), 1.36(s, 6H×½), 2.28 (s, 3H×½), 2.31(s, 3H×½), 2.43 (d, J=7.1 Hz, 2H×½: corresponding to the methylene protons of 1-pentene), 3.32(d, J=5.7 Hz, 2H×½: corresponding to the methylene protons of 2-pentene), 5.5~6.4(m, 2H), 6.6~7.4(m, 13H).

(2) 1-(3-Phenoxyphenyl)-4-(4-methylphenyl)-4-methylpentane

To 30 ml of ethyle acetate, 1.9 g of a mixture of 50% 1-(3-phenoxyphenyl)-4-(4-methylphenyl)-4-methyl-2-pentene and 50% 1-(3-phenoxyphenyl)-4-(4-methylphenyl)-4-methyl-1-pentene was added and dissolved, and thereto 0.4 g of 5% Pd-C was added, and the mixture was stirred under a pressure of 20 kg/cm² G with hydrogen gas at room temperature. After three hours, Pd-C was removed by filtration, and ethyl acetate was evaporated under reduced pressure.

The residue was purified by column chromatography on 50 g of silica gel (1:2 mixed solvent of benzene and hexane was used as eluent) to give 1.8 g of the desired 1-(3-phenoxyphenyl)-4-(4-methylphenyl)-4-methylpentane.

$n_D^{20.0} 1.5710$.

$\nu_{max}^{Neat}(cm^{-1})$: 1595, 1495, 1260, 1225, 820, 700.

$\delta_{TMS}^{CCl_4}(ppm)$: 1.24(s, 6H), 1.0~1.7(m, 4H), 2.25(s, 3H), 2,42(t, J=7.5 Hz, 2H), 6.55~7.25(m, 13H).

SYNTHESIS EXAMPLE 2

Synthesis of 1-(3-phenoxyphenyl)-4-(3-trifluoromethylphenyl)-4-methylpentane

The synthesis was carried out according to the following procedure.

(1) 1-(3-Phenoxyphenyl)-4-(3-trifluoromethylphenyl)-4-methyl-2-pentene and 1-(3-phenoxyphenyl)-4-(3-trifluoromethylphenyl)-4-methyl-1-pentene (a) To 30 ml of ethanol were added 4.3 g of 2-(3-trifluoromethylphenyl)-2-methyl-3-butanone, 3.7 g of 3-phenoxybenzaldehyde and 1.0 g of KOH, and the mixture was stirred at room temperature around the clock. The reaction mixture was poured into 300 ml of water and extracted with benzene. The benzene extract was washed with water and dried, and the solvent was evaporated under reduced pressure to give 7.5 g of the residue. The residue was purified by column chromatography on 210 g of silica gel (eluent: benzene) to give 5.9 of pure 1-(3-phenoxyphenyl)-4-(3-trifluoromethylphenyl)-4-methyl-1-penten-3-one.

$n_D^{19.8} 1.5820$.

$\nu_{max}^{Neat}(cm^{-1})$: 1690, 1610, 1590, 1580, 1490, 1460, 1330, 1240, 1165, 1125, 1075, 1060, 1000, 980, 805, 705, 695.

(b) To 10 ml of dry ether was added 0.71 g of lithium aluminum hydride, and thereinto a solution of 5.0 g of anhydrous aluminum chloride in 20 ml of dry ether was added dropwise. Then, a solution prepared by adding 4.4 g of 1-(3-phenoxyphenyl)-4-(3-trifluoromethylphenyl)-4-methyl-1-penten-3-one obtained according to the above (a) to 20 ml of dry ether was added dropwise into the mixture, and refluxed with heating for 30 minutes. Ethyl acetate and then water were added dropwise into the reaction mixture with cooling by ice water. The reaction mixture was extracted with benzene, and the benzene extract was washed with water and dried, and the solvent was evaporated under reduced pressure to give 4.4 g of the residue.

The residue was purified by column chromatography on 100 g of silica gel (1:2 mixed solvent of benzene and hexane was used as eluent) to give 2.2 g of a mixture of 70% 1-(3-phenoxyphenyl)-4-(3-trifluoromethylphenyl)-4-methyl-2-pentene and 30% 1-(3-phenoxyphenyl)-4-(3-trifluoromethylphenyl)-4-methyl-1-pentene.

$n_D^{19.8} 1.5517$.

$\nu_{max}^{Neat}(cm^{-1})$: 1590, 1500, 1305, 1260, 1220, 1175, 1140, 1080, 705, 695.

$\delta_{TMS}^{CCl_4}(ppm)$: 1.40(s, 6H), 2.45(d, J=6.9 Hz, 2H×(30/100): corresponding to the methylene protons of 1-pentene), 3.31(d, J=4.8 Hz, 2H×(70/100): corresponding to the methylene protons of 2-pentene), 3.5~6.4(m, 2H), 6.45~7.6(m, 13H)

(2) 1-(3-Phenoxyphenyl)-4-(3-trifluoromethylphenyl)-4-methylpentane

To 25 ml of ethyl acetate were added 1.2 g of a mixture of 70% 1-(3-phenoxyphenyl)-4-(3-trifluoromethylphenyl)-4-methyl-2-pentene and 30% 1-(3-phenoxyphenyl)-4-(3-trifluoromethylphenyl)-4-methyl-1-pentene, and 0.40 g of 5% Pd-C, and the mixture was stirred under a pressure of 20 kg/cm$^2$ G was hydrogen gas at 65° C. After three hours, Pd-C was removed by filtration and the solvent was evaporated under reduced pressure to give 1.2 g of the residue.

The residue was purified by column chromatography on 25 g of silica gel (1:2 mixed solvent of benzene and hexane was used as eluent) to give 0.8 g of 1-(3-phenoxyphenyl)-4-(3-trifluoromethylphenyl)-4-methylpentane.

$n_D^{19.5}$1.5373.

$\nu_{max}^{Neat}$(cm$^{-1}$): 1580, 1480, 1330, 1245, 1210, 1160, 1120, 1170, 695, 680.

$\delta_{TMS}^{CCl4}$(ppm): 1.31(s, 6H), 1.1~1.8(m, 4H), 2.47(t, J=6.6 Hz, 2H), 6.6~7.6(m, 13H).

SYNTHESIS EXAMPLE 3

Synthesis of 1-(3-phenoxy-4-fluorophenyl)-4-(4-ethoxyphenyl)-4-methylpentane

The synthesis was carried out according to the following procedure.

(1) 1-(3-Phenoxy-4-fluorophenyl)-4-(4-ethoxyphenyl)-4-methyl-2-pentene and 1-(3-phenoxy-4-fluorophenyl)-4-(4-ethoxyphenyl)-4-methyl-1-pentene (a) In the same manner as described in (a) of (1) of Synthesis Example 2, 12.0 g of the residue was obtained by using 6.2 g of 2-(4-ethoxyphenyl)-2-methyl-3-butanone and 6.5 g of 3-phenoxy-4-fluorobenzaldehyde. The residue was purified by column chromatography on 200 g of silica gel (eluent: benzene) to give 5.8 g of 1-(3-phenoxy-4-fluorophenyl)-4-(4-ethoxyphenyl)-4-methyl-1-penten-3-one.

$n_D^{19.7}$1.5900.

$\nu_{max}^{Neat}$(cm$^{-1}$): 1690, 1610, 1590, 1510, 1490, 1290, 1270, 1250, 1210, 1185, 1120, 1060, 820, 750, 690.

(b) In the same manner as described in (b) of (1) of Synthesis Example 2, 3.9 of the residue was obtained by using 4.1 g of 1-(3-phenoxy-4-fluorophenyl)-4-(4-ethoxyphenyl)-4-methyl-1-penten-3-one prepared according to the above (a). The residue was purified by column chromatography on 80 g of silica gel (2:3 mixed solvent of benzene and hexane was used as eluent) to give 1.44 g of a mixture of 45% 1-(3-phenoxy-4-fluorophenyl)-4-(4-ethoxyphenyl)-4-methyl-2-pentene and 55% 1-(3-phenoxy-4fluorophenyl)-4-(4-ethoxyphenyl)-4-methyl-1-pentene.

$n_D^{20.1}$1.5745.

$\nu_{max}^{Neat}$(cm$^{-1}$): 1610, 1585, 1510, 1490, 1290, 1270, 1245, 1210, 1180, 1115, 1045, 965, 825, 690.

$\delta_{TMS}^{CCl4}$(ppm): 1.2~1.5(m, 3H×3), 2.39(d, J=7.1 Hz, 2H×(55/100): corresponding to the methylene protons of 1-pentene), 3.27(d, J=5.0 Hz, 2H×(45/100): corresponding to the methylene protons of 2-pentene), 3.8~4.1(m, 2H), 5.4~6.3(m, 2H), 6.5~7.4(m, 12H).

(2) 1-(3-Phenoxy-4-fluorophenyl)-4-(4-ethoxyphenyl)-4-methylpentane

In the same manner as described in (2) of Synthesis Example 2, 0.9 g of a mixture of 45% 1-(3-phenoxy-4-fluorophenyl)-4-(4-ethoxyphenyl)-4-methyl-2-pentene and 55% 1-(3-phenoxy-4-fluorophenyl)-4-(4-ethoxyphenyl)-4-methyl-1-pentene was reduced to give 1.0 g of the residue. The residue was purified by column chromatography on 20 g of silica gel (2:3 mixed solvent of benzene and hexane was used as eluent) to give 0.80 g of 1-(3-phenoxy-4-fluorophenyl)-4-(4-ethoxyphenyl)-4-methylpentane.

$n_D^{20.0}$1.5578.

$\nu_{max}^{Neat}$(cm$^{-1}$): 1585, 1510, 1490, 1290, 1270, 1240, 1210, 1180, 1115, 1045, 820, 750, 685.

$\delta_{TMS}^{CCl4}$(ppm): 1.22(s, 6H), 1.36(t, J=6.9 Hz, 3H) 2.39(t, J=7.7 Hz, 2H), 3.91(q, J=6.9 Hz, 2H), 1.0~1.7(m, 4H), 6.5~7.4(m, 12H).

SYNTHESIS EXAMPLE 4

Synthesis of 1-(3-phenoxyphenyl)-4-(3,4-methylenedioxyphenyl)-4-methylpentane

The synthesis was carried out according to the following procedure.

(1) 1-(3-Phenoxyphenyl)-4-(3,4-methylenedioxyphenyl)-4-methyl-1-pentene and 1-(3-phenoxyphenyl)-4-(3,4-methylenedioxyphenyl)-4-methyl-2-pentene (a) A mixture of 10 g of 2-(3,4-methylenedioxyphenyl)-2-methyl-3-butanone, 9.6 g of 3-phenoxybenzaldehyde, 50 ml of ethanol and 2 g of KOH was stirred at 60° C. for 30 minutes. Then, the reaction mixture was poured into 300 ml of water and extracted with benzene. The benzene extract was washed with water and dried, and the solvent was evaporated under reduced pressure to give 23 g of the residue. The residue was purified by column chromatography on silica gel (eluent: benzene) to give 15.3 g of pure 1-(3-phenoxyphenyl)-4-(3,4-methylenedioxyphenyl)-4-methyl-1-penten-3-one.

$n_D^{19.9}$1.6208

$\nu_{max}^{Neat}$(cm$^{-1}$): 1705, 1620, 1600, 1590, 1515, 1495, 1460, 1250, 1080, 1070, 1050, 940, 825, 690.

$\delta_{TMS}^{CCl4}$(ppm): 1.43(s, 6H), 5.85(s, 2H), 6.36~7.70(m, 14H).

(b) In the same manner as described in (b) of (1) of Synthesis Example 1, 12 g of 1-(3-phenoxyphenyl)-4-(3,4-methylenedioxyphenyl)-4-methyl-1-penten-3-one obtained according to the above (a) was treated to give 2.0 g of a mixture of 40% 1-(3-phenoxyphenyl)-4-(3,4-methylenedioxyphenyl)-4-methyl-2-pentene and 60% 1-(3-phenoxyphenyl)-4-(3,4-methylenedioxyphenyl)-4-methyl-1-pentene.

$n_D^{20.0}$1.5966.

$\nu_{max}^{Neat}$(cm$^{-1}$): 1600, 1590, 1510, 1495, 1455, 1250, 1220, 1050, 945, 820, 700.

$\delta_{TMS}^{CCl4}$(ppm): 1.2~1.3(m, 6H), 2.39(d, J=5.9 Hz, 2H×(60/100): corresponding to the methylene protons of 1-pentene), 3.29(d, J=5.4 Hz, 2H×(40/100): corresponding to the methylene protons of 2-pentene), 5.4~6.4(m, 4H), 6.5~7.4(m, 12H).

(2) 1-(3-Phenoxyphenyl)-4-(3,4-methylenedioxyphenyl)-4-methylpentane

In the same manner as described in (2) of Synthesis Example 1, the mixture of 1-(3-phenoxyphenyl)-4-(3,4-methylenedioxyphenyl)-4-methyl-1-pentene and 1-(3-phenoxyphenyl)-4-(3,4-methylenedioxyphenyl)-4-methyl-2-pentene, obtained according to the above (b) of (1), was treated to give quantitatively 1-(3-phenoxyphenyl)-4-(3,4-methylenedioxyphenyl)-4-methylpentane.

$n_D^{20.0}$1.5824.

$\nu_{max}^{Neat}$(cm$^{-1}$): 1570, 1490, 1475, 1430, 1235, 1200, 1150, 1095, 1025, 925, 800, 740, 680.

$\delta_{TMS}^{CCl4}$(ppm): 1.07~1.70(m, 4H), 1.23(s, 6H), 2.46(t, 2H), 5.82(s, 2H), 6.5~7.4(m, 12H).

SYNTHESIS EXAMPLE 5

Synthesis of 1-(3-phenoxyphenyl)-4-(4-methoxyphenyl)-4-methylpentane

The synthesis was carried out according to the following procedure.

(1) 1-(3-Phenoxyphenyl)-4-(4-methoxyphenyl)-4-methyl-1-pentene and 1-(3-phenoxyphenyl)-4-(4-methoxyphenyl)-4-methyl-2-pentene (a) A mixture of 10 g of 2-(4-methoxyphenyl)-2-methyl-3-butanone, 33.7 g of 3-phenoxybenzaldehyde, 80 ml of methanol and 4.0 g of KOH was stirred at 40° C. for two hours, and then treated in the same manner as described in (a) of (1) of Synthesis Example 1 to give 25 g of 1-(3-phenoxyphenyl)-4-(methoxyphenyl)-4-methyl-1-penten-3-one.

$n_D^{20.2} 1.6094$.

$\nu_{max}^{Neat}(cm^{-1})$: 1680, 1600, 1575, 1480, 1230, 1050, 880, 825, 750, 685.

$\delta_{TMS}^{CCl_4}$(ppm): 1.44(s, 6H), 3.69(s, 3H), 6.34~7.61(m, 15H).

(b) In the same manner as described in (b) of (1) of Synthesis Example 1, 23.7 g of 1-(3-phenoxyphenyl)-4-(4-methoxyphenyl)-4-methyl-1-pente-3-one obtained according to the above (a) was treated to give 9.0 g of a mixture of 40% 1-(3-phenoxyphenyl)-4-(4-methoxyphenyl)-4-methyl-2-pentene and 60% 1-(3-phenoxyphenyl)-4-(4-methoxyphenyl)-4-methyl-1-pentene.

$n_D^{19.7} 1.5948$.

$\nu_{max}^{Neat}(cm^{-1})$: 1620, 1590, 1520, 1500, 1450, 1255, 1220, 1190, 1040, 835, 700.

$\delta_{TMS}^{CCl_4}$(ppm): 1.20~1.40 (m, 6H), 2.40 (d, J=6.5 Hz, 2H×(60/100): corresponding to the methylene protons of 1-pentene), 3.28 (d, J=5.6 Hz, 2H×(40/100): corresponding to the methylene protons of 2-pentene), 3.6~3.8 (m, 3H), 5.2~6.4 (m, 2H), 6.6~7.4 (m, 13H).

(2) 1-(3-Phenoxyphenyl)-4-(4-methoxyphenyl)-4-methylpentane

In the same manner as described in (2) of Synthesis Example 1, the mixture of 1-(3-phenoxyphenyl)-4-(4-methoxyphenyl)-4-methyl-2-pentene and 1-(3-phenoxyphenyl)-4-(4-methoxyphenyl)-4-methyl-1-pentene, obtained according to the above (1), was treated to give quantitatively 1-(3-phenoxyphenyl)-4-(4-methoxyphenyl)-4-methylpentane.

$n_D^{19.8} 1.5774$.

$\nu_{max}^{Neat}(cm^{-1})$: 1610, 1580, 1515, 1485, 1250, 1215, 1180, 1035, 825, 755, 690.

$\delta_{TMS}^{CCl_4}$(ppm): 0.88~1.73 (m, 4H), 1.26 (s, 6H), 2.46 (t, 2H), 3.73 (s, 3H), 6.6~7.4 (m, 13H).

SYNTHESIS EXAMPLE 6

Synthesis of 1-(3-phenoxy-4-fluorophenyl)-4-(4-methoxyphenyl)-4-methylpentane (1) A mixture of 7.6 g of 2-(4-methoxhyphenyl)-2-methyl-3-butanone, 8.5 g of 3-phenoxy-4-fluorobenzaldehyde, 30 ml of methanol and 2 g of KOH was stirred at 60° C. for two hours. In the same manner as described in (a) of (1) of Synthesis Example 1, the reaction mixture was treated to give 5 g of 1-(3-phenoxy-4-fluorophenyl)-4-(4-methoxyphenyl)-4-methyl-1-penten-3-one.

$n_D^{19.7} 1.6058$.

$\nu_{max}^{Neat}(cm^{-1})$: 1680, 1605, 1580, 1420, 1290, 1270, 1250, 1205, 1180, 1105, 1060, 1030, 980, 825, 745, 680.

$\delta_{TMS}^{CCl_4}$(ppm): 1.45 (s, 6H), 3.74 (s, 3H), 6.26~7.61 (m, 14H).

In the same manner as described in (b) of (1) of Synthesis Example 1, 4.2 g of 1-(3-phenoxy-4-fluorophenyl)-4-(4-methoxyphenyl)-4-methyl-1-penten-3-one obtained according to the above (1) was treated to give 2.8 g of a mixture of 50% 1-(3-phenoxy-4-fluorophenyl)-4-(4-methoxyphenyl)-4-methyl-2-pentene and 50% 1-(3-phenoxy-4-fluorophenyl)-4-(4-methoxyphenyl)-4-methyl-1-pentene.

$n_D^{19.9} 1.5764$.

$\nu_{max}^{Neat}(cm^{-1})$: 1605, 1585, 1510, 1490, 1290, 1270, 1245, 1210, 1180, 1110, 1035, 825, 680. $\delta_{TMS}^{CCl_4}$(ppm): 1.2~1.4 (m, 6H), 2.38 (d, J=6.8 Hz, 2H×(50/100): corresponding to the methylene protons of 1-pentene), 3.40 (d, J=5.6 Hz, 2H×(50/100): corresponding to the methylene protons of 2-pentene), 3.6~3.8 (m, 3H), 5.2~6.3 (m, 2H), 6.5~7.4 (m, 12H).

(2) In the same manner as described in (2) of Synthesis Example 1, the mixture of 1-(3-phenoxy-4-fluorophenyl)-4-(4-methoxyphenyl)-4-methyl-2-pentene and 1-(3-phenoxy-4-fluorophenyl)-4-(4-methoxyphenyl)-4-methyl-1-pentene obtained according to the above (1) was treated to give quantitatively 1-(3-phenoxy-4-fluorophenyl)-4-(4-methoxyphenyl)-4-methylpentane.

$n_D^{20.0} 1.5642$.

$\nu_{max}^{Neat}(cm^{-1})$: 1620, 1600, 1520, 1500, 1430, 1285, 1260, 1220, 1195, 1175, 1125, 1040, 835, 755, 695.

$\delta_{TMS}^{CCl_4}$(ppm): 0.92~1.67 (m, 4H), 1.22 (s, 6H), 2.39 (t, 2H), 3.68 (s, 3H), 6.5~7.4 (m, 12H).

SYNTHESIS EXAMPLE 7

Synthesis of 1-(3-phenoxyphenyl)-4-(4-chlorophenyl)-4-methylhexane

In the same manner as described in Synthesis Example 2, 3-(4-chlorophenyl)-3-methyl-2-pentanone and 3-phenoxybenzaldehyde were treated to give 1-(3-phenoxyphenyl)-4-(4-chlorophenyl)-4-methyl-hexane.

$n_D^{19.8} 1.5748$.

$\nu max^{Neat}(cm^{-1})$: 1590, 1500, 1455, 1260, 1220, 1020, 825, 700.

$\delta_{TMS}^{CCl_4}$(ppm): 0.63 (t, J=7 Hz, 3H), 1.08~1.9 (m, 6H), 1.21 (s, 3H), 2.44 (t, 2H), 6.6~7.4 (m, 13H).

SYNTHESIS EXAMPLE 8

Synthesis of 1-(3-phenoxyphenyl)-4-(4-chlorophenyl)-4-methylpentane

In the same manner as described in Synthesis Example 2, the equivalent mixture of α,α-dimethyl-(4-chlorophenyl)acetaldehyde and 3-phenoxyacetophenone was treated to give 1-(3-phenoxyphenyl)-4-(4-chlorophenyl)-4-methylpentane.

$n_D^{20.2} 1.5786$.

$\nu_{max}^{Neat}(cm^{-1})$: 1600, 1520, 1500, 1430, 1300, 1285, 1220, 1170, 1125, 1020, 830, 755, 695.

$\delta_{TMS}^{CCl_4}$(ppm): 0.98~1.72 (m, 4H), 1.26 (s, 6H), 2.42 (t, 2H), 6.67~7.40 (m, 12H).

SYNTHESIS EXAMPLE 9

Synthesis of 1-(3-phenoxyphenyl)-4-(4-isopropoxyphenyl)-4-methylpentane (1) A mixture of 5.0 g of 1-(3-phenoxyphenyl)-4-(4-methoxyphenyl)-4-methylpentane, 30 ml of 47% aq HBr and 30 ml of acetic acid was refluxed with heating for eight hours. The reaction mixture was poured into water and extracted with benzene. The benzene extract was washed with water and dried, and the solvent was evaporated under reduced pressure, and the residue was purified by column chromatography on silica gel (eluent: benzene) to give 4.2 g of 1-(3-phenoxyphenyl)-4-(4-hydroxyphenyl)-4-methylpentane.

$n_D^{19.4} 1.5870$.

$\nu_{max}^{Neat}(cm^{-1})$: 3400, 1610, 1580, 1515, 1485, 1440, 1240, 1210, 825, 755, 690, 675.

$\delta_{TMS}^{CCl_4}$(ppm): 1.00~1.68 (m, 4H), 1.20 (s, 6H), 2.43 (t, 2H), 5.52 (broad s, 1H), 6.56~7.38 (m, 13H).

(2) A mixture of 0.5 g of 1-(3-phenoxyphenyl)-4-(4-hydroxyphenyl)-4-methylpentane, 1.5 g of $K_2CO_3$, 3 ml of isopropyl bromide and 20 ml of dimethylformamide was stirred at 130° C. for two hours. The reaction mixture was poured into water and extracted with benzene. The benzene extract was washed with water and dried, and the solvent was evaporated under reduced pressure, and the residue was purified by column chromatography on silica gel (eluent: benzene) to give 0.3 g of 1-(3-phenoxyphenyl)-4-(4-isopropoxyphenyl)-4-methylpentane.

$n_D^{19.6}$ 1.5682.

$\nu_{max}^{Neat}(cm^{-1})$: 1605, 1580, 1510, 1485, 1380, 1245, 1120, 955, 825, 755, 685.

$\delta_{TMS}^{CCl_4}$(ppm): 1.02~1.71 (m, 16H), 2.45 (t, 2H), 4.28~4.56 (m, 1H), 6.57~7.38 (m, 13H).

SYNTHESIS EXAMPLE 10

Synthesis of 1-(3-phenoxy-4-fluorophenyl)-4-(4-difluoromethoxyphenyl)-4-methylpentane (1) In the same manner as described in Synthesis Example 9, 1 g of 1-(3-phenoxy-4-fluorophenyl)-4-(4-methoxphenyl)-4-methylpentane was treated to give 0.6 g of 1-(3-phenoxy-4-fluorophenyl)-4-(4-hydroxyphenyl)-4-methylpentane.

$n_D^{19.9}$ 1.5760.

$\nu_{max}^{Neat}(cm^{-1})$: 3360, 1620, 1600, 1520, 1500, 1435, 1285, 1220, 1130, 840, 760, 700.

$\delta_{TMS}^{CCl_4}$(ppm): 1.02~1.67 (m, 4H), 1.21 (s, 6H), 2.39 (t, 2H), 5.24 (broad s, 1H), 6.52~7.35 (m, 12H).

(2) Chlorodifluoromethane was bubbled into a mixture of 0.5 g of 1-(3-phenoxy-4-fluorophenyl)-4-(4-hydroxyphenyl)-4-methylpentane obtained according to the above (1), 1.0 g of KOH and 20 ml of acetonitrile with stirring at 60° C. for 30 minutes. The reaction mixture was poured into water and extracted with benzene. The benzene extract was washed with water and dried, and the solvent was evaporated under reduced pressure, and the residue was purified by column chromatography on silica gel (eluent: benzene) to give 0.4 g of 1-(3-phenoxy-4-fluorophenyl)-4-(4-difluoromethoxyphenyl)-4-methylpentane.

$n_D^{19.6}$ 1.5414.

$\nu_{max}^{Neat}(cm^{-1})$: 1600, 1520, 1500, 1435, 1395, 1285, 1220, 1140, 1050, 840, 820, 760, 700.

$\delta_{TMS}^{CCl_4}$(ppm): 1.02~1.72 (m, 4H), 1.25 (s, 6H), 2.42 (t, 2H), 6,39 (t, J=35 Hz, 1H), 6.68~7.39 (m, 12H).

SYNTHESIS EXAMPLE 11

Synthesis of 1-(3-phenoxy-4-fluorophenyl)-4-(4-ethoxyphenyl)-4-methylpentane

The synthesis was carried out according to the following procedure.

(1) To 6.4 g of 3-phenoxy-4-fluorobenzyl bromide was added 7 ml of triethylphosphite, and the mixture was stirred at 140° C. for seven hours. After cooling, 13.1 g of the reaction mixture was purified by column chromatography on silica gel (eluent: benzene) to give 6.3 g of diethyl 3-phenoxy-4-fluorobenzylphosphonate.

$\nu_{max}^{Neat}(cm^{-1})$: 1590, 1515, 1490, 1270, 1250, 1025, 960, 795.

$\delta_{TMS}^{CCl_4}$(ppm): 1.04~1.50 (m, 6H), 2.93 (d, J=21 Hz, 2H), 3.70~4.17 (m, 4H), 6.84~7.38 (m, 8H).

(2) 1-(3-Phenoxy-4-fluorophenyl)-4-(4-ethoxyphenyl)-4-methyl-1-pentene

Into a solution of 0.36 g of 60% sodium hydride in 10 ml of dry dimethyl cellosolve was added dropwise a solution of 3.0 g of diethyl 3-phenoxy-4-fluorobenzylphosphoate in 10 ml of dry dimethyl cellosolve, and the mixture was stirred at 50° C. for 30 minutes. Then, a solution of 1.55 g of 3-(4-ethoxyphenyl)-3-methylbutylaldehyde in 5 ml of dry dimethyl cellosolve was added dropwise into the mixture, and stirred at 50° C. for one hour. The reaction mixture was poured into water and extracted with benzene. The benzene extract was washed with water and dried with anhydrous sodium sulfate, and the solvent was evaporated, and the residue was purified by column chromatography on silica gel to give 2.49 g of 1-(3-phenoxy-4-fluorophenyl)-4-(4-ethoxyphenyl)-4-methyl-1-pentene.

$n_D^{19.8}$ 1.5902.

$\nu_{max}^{Neat}(cm^{-1})$: 1610, 1590, 1515, 1425, 1395, 1370, 1295, 1275, 1255, 1215, 1185, 1120, 1050, 970, 825, 750, 690.

$\delta_{TMS}^{CCl_4}$(ppm): 1.28 (s, 6H), 1.38 (t, J=7 Hz, 3H), 2.36 (d, J=8 Hz, 2H), 3.89 (q, J=7 Hz, 2H), 5.54~6.25 (m, 2H), 6.57~7.32 (m, 12H).

(3) 1-(3-Phenoxy-4-fluorophenyl)-4-(4-ethoxyphenyl)-4-methylpentane

A mixture of 2.0 g of 1-(3-phenoxy-4-fluorophenyl)-4-(4-ethoxyphenyl)-4-methyl-1-pentene, 0.2 g of 5% Pd-C and 40 ml of ethyl acetate was put in a 200 ml autoclave and pressed up to 10 kg/cm² G with hydrogen gas, and stirred at 80° C. for three hours. After cooling, the reaction mixture was filtered and the solvent was evaporated, and the residue was purified by column chromatography on silica gel to 1.7 g of 1-(3-phenoxy-4-fluorophenyl)-4-(4-ethoxyphenyl)-4-methylpentane.

$n_D^{20.0}$ 1.5578.

The IR spectrum and NMR spectrum of the above product were identical with those of the product prepared according to Synthesis Example 3.

SYNTHESIS EXAMPLE 12

Triphenylphosphine and a slightly excessive amount of 3-phenoxy-4-fluorobenzyl bromide were mixed into benzene in a flask at −10° C. The tightly stoppered flask was allowed to stand at room temperature overnight to give crystals. The crystals were collected by filtration, washed with benzene and dried. 40 ml mol of the obtained bromide was added to a solution of 40 m mol phenyllithium in 150 ml of dry ether in a stream of nitrogen gas, and the mixture was stirred in a stream of nitrogen gas for three hours. The precipitated lithium bromide was filtered off, and to the filtrate, 40 m mol of 3-(4-ethoxyphenyl)-3-methyl-butylaldehyde was added with cooling, and the mixture was heated to remove ether and stirred at 65° C. for three hours. Then, the reaction mixture was poured into water and extracted with benzene, and the benzene extract was washed with water and dried, and the solvent was evaporated, and the residue was purified by column chromatography on silica gel to give 1-(3-phenoxy-4-fluorophenyl)-4-(4-ethoxyphenyl)-4-methyl-1-pentene.

$n_D^{19.8}$ 1.5902.

The IR spectrum and NMR spectrum of the above product were identical with those of the product obtained according to (2) of Synthesis Example 11.

SYNTHESIS EXAMPLE 13

Synthesis of 1-(3-benzoylphenyl)-4-(3-bromo-4-ethoxyphenyl)-4-methylpentane

The synthesis was carried out according to the following procedure.

(1) 1-(3-Benzoylphenyl)-4-(3-bromo-4-ethoxyphenyl)-4-methyl-1-pentene

To 5 ml of anhydrous dimethyl cellosolve was added 0.1 g of 60% sodium hydride, and thereinto 0.9 g of diethyl 3-benzoylbenzylphosphonate (prepared according to (1) of Synthesic Example 11) was added dropwise, and the mixture was stirred at 50° C. for 30 minutes. Then, a solution of 0.6 g of 3-(3-bromo-4-ethoxyphenyl)-3-methylbutanal in 2 ml of dimethyl cellosolve was added dropwise into the mixture, and stirred at 80° C. for one hour. After cooling, the reaction mixture was poured into water and extracted with benzene, and the benzene extract was washed with water and dried, and evaporated under reduced pressure. The residue was purified by column chromatography on silica gel (eluent: benzene) to give 0.7 g of the desired product.

$n_D^{20.0}$ 1.6129.

$\nu_{max}^{Neat}$(cm$^{-1}$): 1670, 1610, 1590, 1510, 1480, 1460, 1400, 1290, 1270, 1060, 970, 810, 720.

$\delta_{TMS}^{CCl4}$(ppm): 1.32 (s, 6H), 1.46 (t, J=7 Hz, 3H), 2.44 (d, J=7 Hz, 2H), 4.04 (q, J=7 Hz, 2H), 5.95 (d t, J=14 Hz, 7 Hz, 1H), 6.72 (d, J=9 Hz, 1H), 7.0~7.8 (m, 11H).

(2) 1-(3-Benzoylphenyl)-4-(3-bromo-4-ethoxyphenyl)-4-methylpentane

In the same manner as described in (2) of Synthesis Example 2, 1-(3-benzoylphenyl)-4-(3-bromo-4-ethoxyphenyl)-4-methylpentene was treated to give 1-(3-benzoylphenyl)-4-(3-bromo-4-ethoxyphenyl)-4-methylpentane.

$n_D^{20.0}$ 1.5908.

$\nu_{max}^{Neat}$(cm$^{-1}$): 1670, 1610, 1510, 1500, 1480, 1400, 330, 1290, 1260, 1060, 930, 810, 720.

$\nu_{TMS}^{CCl4}$(ppm): 1.23 (s, 6H), 1.42 (t, J=7 Hz, 3H), 1.48 (m, 4H), 2.51 (t, J=7 Hz, 2H), 3.97 (q, J=7 Hz, 2H), 6.66 (d, J=8 Hz, 1H), 6.98 (d d, J=8 Hz, 2 Hz, 1H), 7.20~7.60 (m, 8H), 7.68 (d d, J=7 Hz, 2 Hz, 2H).

SYNTHESIS EXAMPLE 14

Synthesis of 1-(3-benzylphenyl)-4-(4-ethoxyphenyl)-4-methylpentane

The synthesis was carried out according to the following procedure.

(1) 1-(3-benzylphenyl)-4-(4-ethoxyphenyl)-4-methyl-1-pentene

To 5 ml of dry ether was added 0.1 g of lithium aluminum hydride, and thereinto was added a solution of 0.7 g of aluminum chloride in 10 ml of dry ether. A solution of 0.54 g of 1-(3-benzoylphenyl)-4-(4-ethoxyphenyl)-4-methyl-1-pentene (prepared according to (1) of Synthesis Example 12) in 2 ml of dry ether was added dropwise into the mixture, and refluxed for 30 minutes. After cooling to room temperature, ethyl acetate was added dropwise into the mixture. And the mixture was poured into ice water, and extracted with benzene. The benzene extract was washed with water and dried, and evaporated under reduced pressure, and purified by column chromatography on silica gel (1:2 mixed solvent of benzene and hexane) to give 0.45 g of the desired product.

$n_D^{20}$ 1.5892.

$\nu_{max}^{Neat}$(cm$^{-1}$): 1620, 1610, 1590, 1520, 1260, 1190, 1050, 970, 840, 770, 730, 710.

$\delta_{TMS}^{CCl4}$(ppm): 1.30 (s, 6H), 1.38 (t, J=7 Hz, 3H), 2.38 (d, J=7 Hz, 2H), 3.83 (s, 2H), 3.90 (q, J=7 Hz, 2H), 5.82 (d t, J=14 Hz, 7 Hz, 1H), 6.70 (d, J=9 Hz, 2H), 6.80~7.2 (m, 11H).

(2) 1-(3-Benzylphenyl)-4-(4-ethoxyphenyl)-4-methylpentane

In the same manner as described in (2) of Synthesis Example 2, 1-(3-benzylphenyl)-4-(4-ethoxyphenyl)-4-methyl-1-pentene prepared according to the above (1) was reduced to give 1-(3-benzylphenyl)-4-(4-ethoxyphenyl)-4-methylpentane.

$n_D^{20.0}$ 1.5640.

$\nu_{max}^{Neat}$(cm$^{-1}$): 1600, 1510, 1490, 1470, 1240, 1180, 1110, 1040, 920, 820, 690.

$\delta_{TMS}^{CCl4}$(ppm): 1.22 (s, 6H), 1.38 (t, J=7 Hz, 3H), 1.46 (m, 4H), 2.41 (t, J=7 Hz, 2H), 3.84 (s, 2H), 3.90 (q, J=7 Hz, 2H), 6.65 (d, J=8 Hz, 2H), 6.80~7.30 (m, 11H).

The typical synthesis examples of 2-aryl-2-methyl-3-butanone which is a starting material, are shown below.

SYNTHESIS EXAMPLE 15

Preparation of 2-(4-methylphenyl)-2-methyl-3-butanone

To 50 ml of dry ether were added 9.0 g of magnesium turning and 100 mg of $I_2$ as a catalyst, and thereinto 25 ml of methyliodide was dropwise gradually. The reaction mixture was refluxed for 30 minutes. Then, to the reaction mixture was added 200 ml of dry benzene and heated till 80° C. to remove ether from the reaction mixture. And thereinto a solution of 45.6 g of α,α-dimethyl-4methylbenzylnitrile in 50 ml of benzene was added dropwise. After refluxing for three hours, 150 ml of 6N HCl was added dropwise carefully into the reaction mixture with cooling by ice-water. After refluxing for one hour, the mixture was cooled to room temperature and the benzene layer was separated. The benzene solution was washed with water and dried with anhydrous sodium sulfate, and the benzene was evaporated under reduced pressure to give 45.2 g of the residue. The residue was distilled under reduced pressure to give 20.0 g (94°-95° C./5 mm Hg) of pure 2-(4-methylphenyl)-2-methyl-3-butanone.

$\delta_{TMS}^{CCl4}$(ppm): 1.41 (s, 6H), 1.81 (s, 3H), 2.31 (s, 3H), 7.07 (s, 4H).

SYNTHESIS EXAMPLE 16

Preparation of 2-(4-chlorophenyl)-2-methyl-3-butanone

To 100 ml of dry ether were added 13.0 g of magnesium turnings and $I_2$ of an amount suitable as a catalyst, and thereinto 66 g of methyliodide was added dropwise with care, and the reaction mixture was refluxed for one hour. Then, to the reaction mixture was added 150 ml of dry benzene and heated till 80° C. to remove ether from the reaction mixture.

A solution of 45 g of α,α-dimethyl-4-chlorobenzylnitrile in 30 ml of benzene was added dropwise into the reaction mixture, and refluxed for three hours. 270 ml of 6N HCl was carefully added to the reaction mixture with cooling by ice-water. Then, the mixture was refluxed for 48 hours. After cooling to room temperature, the benzene layer was separated. The benzene solution was washed with water and dried, and the solvent was evaporated under reduced pressure to give 52 g of the residue. The residue was distilled to give 43.0 g of (104° C./5 mm Hg) of pure 2-(4-chlorophenyl)-2-methyl-3-butanone.

$n_D^{20.0}$ 1.5254.

$\nu_{max}^{Neat}$(cm$^{-1}$): 1730, 1500, 1380, 1370, 1140, 1115, 1020, 840, 690.

$\delta_{TMS}^{CCl4}$ (ppm): 1.43(s,6H),1.85(s,3H), 7.16(d,$J_{AB}$ = 9.1Hz,2H) } AB type -continued 7.28(d,$J_{AB}$ = 9.1Hz,2H)

SYNTHESIS EXAMPLE 17

Preparation of 2-(4-methoxyphenyl)-2-methyl-3-butanone

In the same manner as described in Synthesis Example 15, 51.4 g (106°–111° C./4 mm Hg) of pure 2-(4-methoxyphenyl)-2-methyl-3-butanone was obtained by using 58 g of α,α-dimethyl-4-methoxybenzylnitrile.

$n_D^{20.1}$ 1.5230.

$\nu_{max}^{Neat}$(cm$^{-1}$): 1705, 1610, 1515, 1465, 1355, 1305, 1250, 1185, 830.

$\delta_{TMS}^{CCl4}$ (ppm): 1.38(s,6H),1.80(s,3H),3.69(s,3H),
6.78(d,$J_{AB}$ = 9.0Hz,2H)
7.10(d,$J_{AB}$ = 9.0Hz,2H)  } AB type

SYNTHESIS EXAMPLE 18

Preparation of 2-(3,4-methylenedioxyphenyl)-2-methyl-3-butanone

In the same manner as described in Synthesis Example 15, 83.2 g (116°–117° C./0.9 mm Hg) of pure 2-(3,4-methylendioxyphenyl)-2-methyl-3-butanone was obtained by using 93 g of α,α-dimethyl-3,4-methylendioxybenzylnitrile.

$n_D^{19.8}$ 1.5306.

$\nu_{max}^{Neat}$(cm$^{-1}$): 1710, 1510, 1500, 1490, 1480, 1430, 1230, 1130, 1110, 1035, 930, 810, 680.

$\delta_{TMS}^{CCl4}$(ppm): 1.39 (s, 6H), 1.85 (s, 3H), 5.88 (s, 2H), 6.6~6.8 (m, 3H).

SYNTHESIS EXAMPLE 19

Preparation of 2-(4-ethoxyphenyl)-2-methyl-3-butanone

In the same manner as described in Synthesis Example 15, 44.0 g (115° C./4 mm Hg) of pure 2-(4-ethoxyphenyl)-2-methyl-3-butanone was obtained.

$n_D^{20.0}$ 1.5122.

$\nu_{max}^{Neat}$(cm$^{-1}$): 1700, 1510, 1250, 1180.

$\delta_{TMS}^{CCl4}$ (ppm): 1.3~1.5(m,9H),1.82(s,3H),
2.97(q,J = 7.2Hz,2H),
6.76(d,$J_{AB}$ = 8.7Hz,2H)
7.08(d,$J_{AB}$ = 8.7Hz,2H)  } . AB type

SYNTHESIS EXAMPLE B 20

Preparation of 2-(3-trifluoromethylphenyl)-2-methyl-3-butanone

In the same manner as described in Synthesis Example 16, 10 g of α,α-dimethyl-3-trifluoromethylbenzylnitrile was treated to give 9.6 g of the residue. The residue was purified by column chromatography on 200 g of silica gel (eluent: benzene) to give 4.3 g of pure 2-(3-trifluoromethylphenyl)-2-methyl-3-butanone.

$\delta_{max}^{Neat}$(cm$^{-1}$): 1700, 1330, 1235, 1160, 1125, 1070, 800, 700.

Typical examples of the compounds of the present invention are shown in Table 1.

TABLE 1

| Compound No. | Ar | R$^1$ | R$^2$ | R$^3$ | Physical Property Values | |
|---|---|---|---|---|---|---|
| 1 | 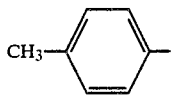 | CH$_3$ | CH$_3$ | 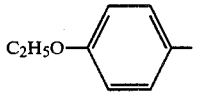 | $n_D^{20.0}$ 1.5710<br>C$_{25}$H$_{28}$O<br>Calculated (%)<br>C: 87.16<br>H: 8.19 | Found (%)<br>87.25<br>7.98 |
| 2 | 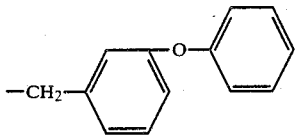 | CH$_3$ | CH$_3$ | 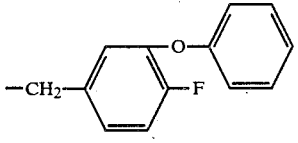 | $n_D^{19.5}$ 1.5373<br>C$_{25}$H$_{25}$F$_3$O<br>Calculated (%)<br>C: 75.36<br>H: 6.32<br>F: 14.31 | Found (%)<br>75.21<br>6.40<br>14.18 |
| 3 | 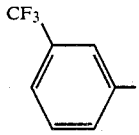 | CH$_3$ | CH$_3$ | 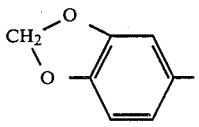 | $n_D^{20.0}$ 1.5578<br>C$_{26}$H$_{29}$FO$_2$<br>Calculated (%)<br>C: 79.56<br>H: 7.45<br>F: 4.84 | Found (%)<br>79.67<br>7.54<br>4.79 |
| 4 | 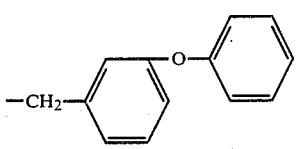 | CH$_3$ | CH$_3$ | 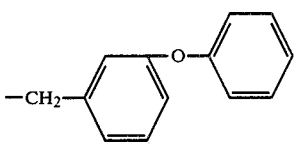 | $n_D^{20.0}$ 1.5824<br>C$_{25}$H$_{26}$O$_3$<br>Calculated (%)<br>C: 80.18<br>H: 7.00 | Found (%)<br>80.01<br>7.14 |

TABLE 1-continued

| Compound No. | Ar | R¹ | R² | R³ | Physical Property Values |
|---|---|---|---|---|---|
| 5 | 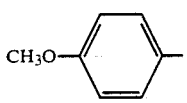 | CH₃ | CH₃ | 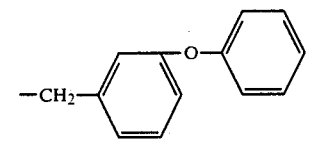 | $n_D^{19.8}$ 1.5774<br>$C_{25}H_{28}O_2$<br>Calculated (%) Found (%)<br>C: 83.29  83.13<br>H: 7.83  7.95 |
| 6 | 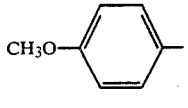 | CH₃ | CH₃ | 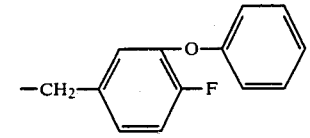 | $n_D^{20.0}$ 1.5642<br>$C_{25}H_{27}FO$<br>Calculated (%) Found (%)<br>C: 82.84  82.98<br>H: 7.51  7.43<br>F: 5.24  5.13 |
| 7 | 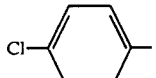 | C₂H₅ | CH₃ | 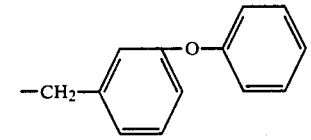 | $n_D^{19.8}$ 1.5748<br>$C_{25}H_{27}ClO$<br>Calculated (%) Found (%)<br>C: 79.24  79.16<br>H: 7.18  7.11<br>Cl: 9.36  9.58 |
| 8 | 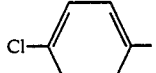 | CH₃ | CH₃ | 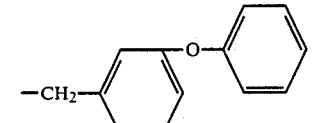 | $n_D^{20.2}$ 1.5786<br>$C_{24}H_{25}ClO$<br>Calculated (%) Found (%)<br>C: 78.99  78.90<br>H: 6.91  6.75<br>Cl: 9.72  9.88 |
| 9 | 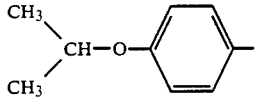 | CH₃ | CH₃ | 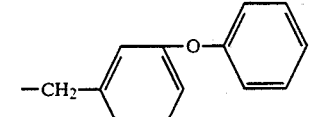 | $n_D^{19.6}$ 1.5682<br>$C_{27}H_{32}O_2$<br>Calculated (%) Found (%)<br>C: 83.46  83.35<br>H: 8.30  8.42 |
| 10 | 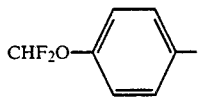 | CH₃ | CH₃ | 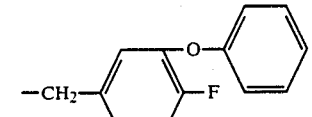 | $n_D^{19.6}$ 1.5414<br>$C_{25}H_{25}F_3O_2$<br>Calculated (%) Found (%)<br>C: 72.45  72.56<br>H: 6.08  6.21<br>F: 13.75  13.69 |
| 11 | 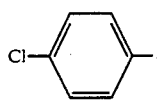 | CH₃ | CH₃ | 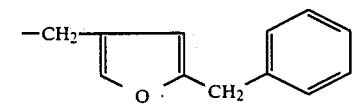 | $C_{25}H_{25}ClO$<br>Calculated (%) Found (%)<br>C: 79.66  79.58<br>H: 6.99  6.63<br>Cl: 9.41  9.62 |
| 12 | 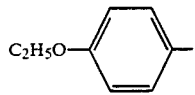 | CH₃ | CH₃ | 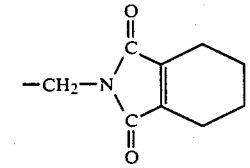 | $C_{22}H_{29}NO_3$<br>Calculated (%) Found (%)<br>C: 74.33  74.26<br>H: 8.22  8.13<br>N: 3.94  4.05 |
| 13 | 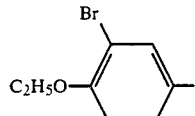 | CH₃ | CH₃ | 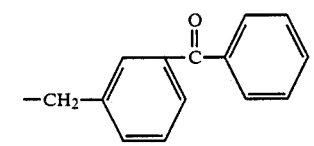 | $n_D^{20.0}$ 1.5908<br>$C_{27}H_{29}BrO_2$<br>Calculated (%) Found (%)<br>C: 69.68  70.03<br>H: 6.28  6.31<br>Br: 17.17  17.51 |
| 14 | 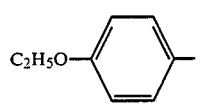 | CH₃ | CH₃ | 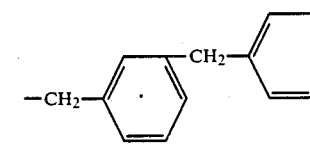 | $n_D^{20.0}$ 1.5640<br>$C_{27}H_{32}O$<br>Calculated (%) Found (%)<br>C: 87.05  87.34<br>H: 8.66  8.69 |

TABLE 1-continued

| Compound No. | Ar | R¹ | R² | R³ | Physical Property Values |
|---|---|---|---|---|---|
| 15 | 4-C₂H₅O-C₆H₄- | CH₃ | CH₃ | -CH(CN)-C₆H₄-O-C₆H₅ | $C_{27}H_{29}NO_2$<br>Calculated (%) / Found (%)<br>C: 81.17 / 81.09<br>H: 7.32 / 7.44<br>N: 3.51 / 3.41 |
| 16 | 4-Cl-C₆H₄- | i-C₃H₇ | H | -CH₂-C₆H₄-O-C₆H₅ | $n_D^{19.8}$ 1.5694<br>$C_{25}H_{27}ClO$<br>Calculated (%) / Found (%)<br>C: 79.24 / 79.15<br>H: 7.18 / 7.08<br>Cl: 9.36 / 9.53 |
| 17 | C₆H₅- | CH₃ | CH₃ | -CH₂-C₆H₄-O-C₆H₅ | $n_D^{19.8}$ 1.5744<br>$C_{24}H_{26}O$<br>Calculated (%) / Found (%)<br>C: 87.23 / 87.13<br>H: 7.93 / 8.01 |
| 18 | 2-naphthyl | CH₃ | CH₃ | -CH₂-C₆H₄-O-C₆H₅ | $n_D^{19.4}$ 1.5803<br>$C_{28}H_{28}O$<br>Calculated (%) / Found (%)<br>C: 88.38 / 88.26<br>H: 7.42 / 7.50 |
| 19 | 4-C₂H₅O-C₆H₄- | CH₃ | CH₃ | -CH₂-(pyridyl)-O-C₆H₅ | $n_D^{20}$ 1.5639<br>$C_{25}H_{29}NO_2$<br>Calculated (%) / Found (%)<br>C: 79.96 / 79.77<br>H: 7.78 / 7.85<br>N: 3.73 / 3.79 |
| 20 | 4-Cl-C₆H₄- | CH₃ | CH₃ | -CH₂-C₆H₃(F)-O-C₆H₅ | $n_D^{20.0}$ 1.5678<br>$C_{24}H_{24}FClO$<br>Calculated (%) / Found (%)<br>C: 75.28 / 75.43<br>H: 6.32 / 6.24<br>Cl: 9.26 / 9.41<br>F: 4.96 / 4.90 |
| 21 | 3-Cl-C₆H₄- | CH₃ | CH₃ | -CH₂-C₆H₄-O-C₆H₅ | $n_D^{19.7}$ 1.5764<br>$C_{24}H_{25}ClO$<br>Calculated (%) / Found (%)<br>C: 78.99 / 78.68<br>H: 6.91 / 6.77<br>Cl: 9.72 / 9.93 |
| 22 | 3,4-(CH₃O)₂-C₆H₃- | CH₃ | CH₃ | -CH₂-C₆H₄-O-C₆H₅ | $n_D^{20.0}$ 1.5754<br>$C_{26}H_{30}O_3$<br>Calculated (%) / Found (%)<br>C: 79.97 / 79.79<br>H: 7.74 / 7.82 |
| 23 | 4-Cl-C₆H₄- | C₂H₅ | H | -CH₂-C₆H₄-O-C₆H₅ | $n_D^{20.0}$ 1.5772<br>$C_{24}H_{25}ClO$<br>Calculated (%) / Found (%)<br>C: 78.99 / 78.80<br>H: 6.91 / 6.95<br>Cl: 9.72 / 9.88 |

TABLE 1-continued

| Compound No. | Ar | R[1] | R[2] | R[3] | Physical Property Values |
|---|---|---|---|---|---|
| 24 | $C_2H_5O$-C6H4- | $CH_3$ | $CH_3$ | -CH2-C6H4-O-C6H5 | $n_D^{19.5}$ 1.5620<br>$C_{26}H_{30}O_2$<br>Calculated (%) / Found (%)<br>C: 83.38 / 83.21<br>H: 8.07 / 8.19 |
| 25 | $CHCl_2CF_2O$-C6H4- | $CH_3$ | $CH_3$ | -CH2-C6H4-O-C6H5 | $n_D^{19.9}$ 1.5518<br>$C_{26}H_{26}Cl_2F_2O_2$<br>Calculated (%) / Found (%)<br>C: 65.14 / 65.05<br>H: 5.47 / 5.56<br>Cl: 14.79 / 14.93<br>F: 7.93 / 7.87 |
| 26 | 3,4-Cl2-C6H3- | $CH_3$ | $CH_3$ | -CH2-C6H4-O-C6H5 | $n_D^{20.1}$ 1.5838<br>$C_{24}H_{24}Cl_2O$<br>Calculated (%) / Found (%)<br>C: 72.18 / 72.06<br>H: 6.06 / 5.91<br>Cl: 17.76 / 17.92 |
| 27 | C6H5- | $CH_3$ | $CH_3$ | -CH2-C6H3(F)-O-C6H5 | $n_D^{20.0}$ 1.5602<br>$C_{24}H_{25}FO$<br>Calculated (%) / Found (%)<br>C: 82.72 / 82.88<br>H: 7.12 / 7.11<br>F: 5.45 / 5.37 |
| 28 | 3,4-($C_2H_5O$)2-C6H3- | $CH_3$ | $CH_3$ | -CH2-C6H4-O-C6H5 | $n_D^{20.0}$ 1.5638<br>$C_{28}H_{34}O_3$<br>Calculated (%) / Found (%)<br>C: 80.34 / 80.21<br>H: 8.19 / 8.34 |
| 29 | $CH_3$-C6H4- | $CH_3$ | $CH_3$ | -CH2-C6H3(F)-O-C6H5 | $n_D^{19.9}$ 1.5618<br>$C_{25}H_{27}FO$<br>Calculated (%) / Found (%)<br>C: 82.84 / 82.75<br>H: 7.51 / 7.63<br>F: 5.24 / 5.16 |
| 30 | $C_2H_5O$-C6H4- | $CH_3$ | $CH_3$ | -CH2-C6H4-S-C6H5 | $n_D^{20}$ 1.5925<br>$C_{26}H_{30}OS$<br>Calculated (%) / Found (%)<br>C: 79.95 / 79.79<br>H: 7.74 / 7.68<br>S: 8.21 / 8.43 |
| 31 | $C_2H_5O$-C6H4- | \multicolumn{2}{\|}{-CH2CH2CH2CH2- (cyclopentyl)} | -CH2-C6H4-O-C6H5 | $n_D^{19.8}$ 1.5726<br>$C_{27}H_{30}O_2$<br>Calculated (%) / Found (%)<br>C: 83.90 / 83.70<br>H: 7.82 / 7.96 |
| 32 | $CHF_2O$-C6H4- | $CH_3$ | $CH_3$ | -CH2-C6H4-O-C6H5 | $n_D^{19.7}$ 1.5528<br>$C_{25}H_{26}F_2O_2$<br>Calculated (%) / Found (%)<br>C: 75.73 / 75.61<br>H: 6.61 / 6.75<br>F: 9.58 / 9.49 |
| 33 | $n\text{-}C_3H_7O$-C6H4- | $CH_3$ | $CH_3$ | -CH2-C6H4-O-C6H5 | $n_D^{19.7}$ 1.5690<br>$C_{27}H_{32}O_2$<br>Calculated (%) / Found (%)<br>C: 83.46 / 83.39<br>H: 8.30 / 8.43 |

TABLE 1-continued

| Compound No. | Substituents in General Formula [I] Ar | $R^1$ | $R^2$ | $R^3$ | Physical Property Values |
|---|---|---|---|---|---|
| 34 | $C_2H_5O$—⟨phenyl⟩— | $CH_3$ | $CH_3$ | —$CH_2$—⟨phenyl⟩—CO—⟨phenyl⟩ | $n_D^{20.0}$ 1.5729<br>$C_{27}H_{30}O_2$<br>Calculated (%) Found (%)<br>C: 83.90  84.15<br>H: 7.82  7.99 |
| 35 | $CH_2ClCF_2O$—⟨phenyl⟩— | $CH_3$ | $CH_3$ | —$CH_2$—⟨phenyl⟩—O—⟨phenyl⟩ | $n_D^{20.1}$ 1.5594<br>$C_{26}H_{27}ClF_2O_2$<br>Calculated (%) Found (%)<br>C: 70.18  70.06<br>H: 6.12  6.19<br>Cl: 7.97  8.11<br>F: 8.54  8.43 |
| 36 | $C_2H_5O$—⟨phenyl⟩— | $CH_3$ | $CH_3$ | —$CH_2$—⟨phenyl(F)⟩—S—⟨phenyl⟩ | $n_D^{20.0}$ 1.5851<br>$C_{26}H_{29}FOS$<br>Calculated (%) Found (%)<br>C: 76.43  76.08<br>H: 7.15  7.35<br>F: 4.65  4.83<br>S: 7.85  8.02 |
| 37 | ClHC=CF—O—⟨phenyl⟩— | $CH_3$ | $CH_3$ | —$CH_2$—⟨phenyl⟩—O—⟨phenyl⟩ | $n_D^{20.0}$ 1.5662<br>$C_{26}H_{26}ClFO_2$<br>Calculated (%) Found (%)<br>C: 73.49  73.37<br>H: 6.17  6.13<br>Cl: 8.34  8.48<br>F: 4.47  4.40 |
| 38 | $C_2H_5O$—⟨phenyl⟩— | \_cyclobutyl_ (CH₂—CH₂—CH₂—CH₂) | | —$CH_2$—⟨phenyl(F)⟩—O—⟨phenyl⟩ | $n_D^{20.0}$ 1.5656<br>$C_{27}H_{29}FO_2$<br>Calculated (%) Found (%)<br>C: 80.17  80.29<br>H: 7.23  7.29<br>F: 4.70  4.63 |
| 39 | $C_2H_5O$—⟨phenyl⟩— | $CH_3$ | $CH_3$ | —$CH_2$—⟨phenyl⟩—O—⟨phenyl⟩—Cl | $n_D^{20.1}$ 1.5736<br>$C_{26}H_{29}ClO_2$<br>Calculated (%) Found (%)<br>C: 76.36  76.26<br>H: 7.15  7.20<br>Cl: 8.67  8.79 |
| 40 | $C_2H_5O$—⟨phenyl⟩— | $CH_3$ | $CH_3$ | —$CH_2$—⟨pyridyl⟩—O—⟨phenyl⟩—F | $C_{25}H_{28}FNO_2$<br>Calculated (%) Found (%)<br>C: 76.31  76.44<br>H: 7.17  7.08<br>F: 4.83  4.77<br>N: 3.56  3.69 |
| 41 | $C_2H_5O$—⟨phenyl⟩— | $CH_3$ | $CH_3$ | —$CH_2$—⟨phenyl⟩—O—⟨phenyl⟩—F | $n_D^{19.8}$ 1.5592<br>$C_{26}H_{29}FO_2$<br>Calculated (%) Found (%)<br>C: 79.56  79.73<br>H: 7.45  7.34<br>F: 4.84  4.78 |
| 42 | $C_2H_5O$—⟨phenyl⟩— | $CH_3$ | $CH_3$ | —$CH_2$—⟨phenyl⟩—O—⟨phenyl(2-F)⟩ | $n_D^{20.0}$ 1.5592<br>$C_{26}H_{29}FO_2$<br>Calculated (%) Found (%)<br>C: 79.56  79.49<br>H: 7.45  7.53<br>F: 4.84  4.75 |

TABLE 1-continued

| Compound No. | Ar | R¹ | R² | R³ | Physical Property Values |
|---|---|---|---|---|---|
| 43 | 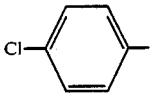 | CH$_3$ | CH$_3$ | 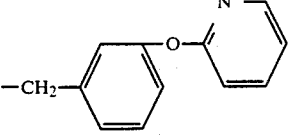 | C$_{23}$H$_{24}$ClNO<br>Calculated (%) Found (%)<br>C: 75.50   75.66<br>H: 6.61   6.71<br>Cl: 9.69   9.82<br>N: 3.83   3.74 |
| 44 | 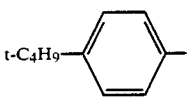 | CH$_3$ | CH$_3$ | 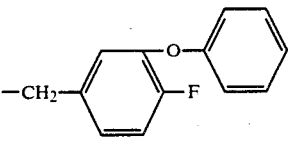 | $n_D^{20.1}$ 1.5330<br>C$_{28}$H$_{33}$FO<br>Calculated (%) Found (%)<br>C: 83.13   83.30<br>H: 8.22   8.15<br>F: 4.70   4.62 |
| 45 | 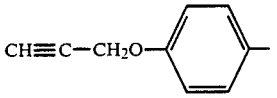 | CH$_3$ | CH$_3$ | 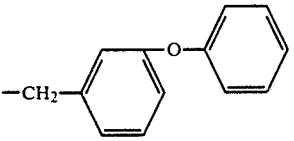 | C$_{27}$H$_{28}$O$_2$<br>Calculated (%) Found (%)<br>C: 84.34   84.39<br>H: 7.34   7.45 |
| 46 | 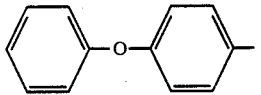 | CH$_3$ | CH$_3$ | 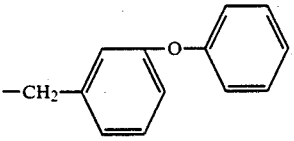 | C$_{30}$H$_{30}$O$_2$<br>Calculated (%) Found (%)<br>C: 85.27   85.19<br>H: 7.16   7.29 |
| 47 | 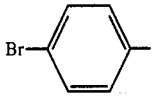 | CH$_3$ | CH$_3$ | 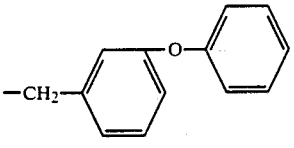 | C$_{24}$H$_{25}$BrO<br>Calculated (%) Found (%)<br>C: 70.41   70.26<br>H: 6.16   6.07<br>Br: 19.52   19.71 |
| 48 | 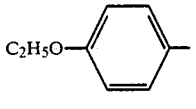 | CH$_3$ | CH$_3$ | 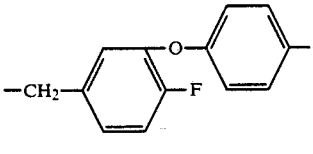 | C$_{30}$H$_{33}$FO$_3$<br>Calculated (%) Found (%)<br>C: 78.23   78.35<br>H: 7.22   7.31<br>F: 4.13   4.04 |
| 49 | 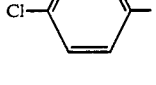 | i-C$_3$H$_7$ | CH$_3$ | 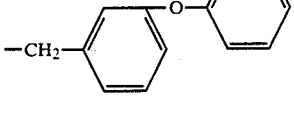 | C$_{26}$H$_{29}$ClO<br>Calculated (%) Found (%)<br>C: 79.47   79.33<br>H: 7.44   7.32<br>Cl: 9.02   9.23 |
| 50 | 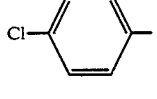 | 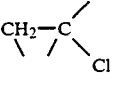 | | 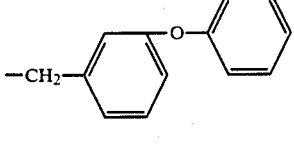 | C$_{24}$H$_{21}$Cl$_3$O<br>Calculated (%) Found (%)<br>C: 66.76   66.61<br>H: 4.90   4.82<br>Cl: 24.63   24.87 |
| 51 | 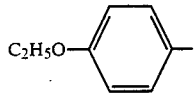 | CH$_3$ | CH$_3$ | 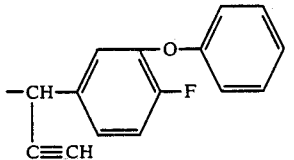 | C$_{28}$H$_{29}$FO$_2$<br>Calculated (%) Found (%)<br>C: 80.74   80.56<br>H: 7.02   7.13<br>F: 4.56   4.51 |

TABLE 1-continued

| Compound No. | Substituents in General Formula [I] Ar | $R^1$ | $R^2$ | $R^3$ | Physical Property Values |
|---|---|---|---|---|---|
| 52 | 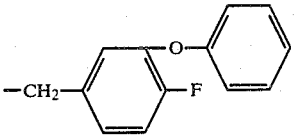 C₂H₅O—⟨phenyl⟩— | CH₃ | CH₃ | —CH₂—⟨phenyl-F⟩—O—⟨phenyl⟩ | $n_D^{20.0}$ 1.5540<br>$C_{26}H_{29}FO$<br>Calculated (%) Found (%)<br>C: 82.94   82.67<br>H: 7.76   7.91<br>F: 5.05   4.93 |
| 53 | Cl—⟨phenyl⟩— | CH₃ | CH₃ | —CH₂—⟨phenyl-F⟩—O—⟨phenyl-F⟩ | $n_D^{20.0}$ 1.5442<br>$C_{24}H_{23}ClF_2O$<br>Calculated (%) Found (%)<br>C: 71.90   71.71<br>H: 5.78   5.63<br>Cl: 8.84   8.98<br>F: 9.48   9.56 |
| 54 | Cl—⟨phenyl⟩— | CH₃ | CH₃ | —CH(CN)—⟨phenyl⟩—O—⟨phenyl⟩ | $n_D^{20.0}$ 1.5772<br>$C_{25}H_{24}ClNO$<br>Calculated (%) Found (%)<br>C: 77.00   77.17<br>H: 6.20   6.35<br>Cl: 9.09   9.22<br>N: 3.59   3.8 |
| 55 | C₂H₅O—⟨phenyl⟩— | CH₃ | CH₃ | —CH₂—⟨phenyl-F⟩—O—⟨phenyl-F⟩ | $n_D^{20.0}$ 1.5520<br>$C_{26}H_{28}F_2O_2$<br>Calculated (%) Found (%)<br>C: 76.07   76.24<br>H: 6.88   6.99<br>F: 9.26   9.12 |
| 56 | (CH₃)₂CH—⟨phenyl⟩— | CH₃ | CH₃ | —CH₂—⟨phenyl-F⟩—O—⟨phenyl⟩ | $n_D^{20.0}$ 1.5500<br>$C_{27}H_{31}FO$<br>Calculated (%) Found (%)<br>C: 83.04   82.88<br>H: 8.00   8.12<br>F: 4.86   4.79 |
| 57 | C₂H₅O—⟨phenyl-Cl⟩— | CH₃ | CH₃ | —CH₂—⟨phenyl-F⟩—O—⟨phenyl⟩ | $n_D^{19.7}$ 1.5640<br>$C_{26}H_{28}ClFO_2$<br>Calculated (%) Found (%)<br>C: 73.14   73.32<br>H: 6.61   6.45<br>Cl: 8.30   8.48<br>F: 4.45   4.57 |
| 58 | NC—⟨phenyl⟩— | CH₃ | CH₃ | —CH₂—⟨phenyl⟩—O—⟨phenyl⟩ | $n_D^{20}$ 1.5818<br>$C_{25}H_{25}NO$<br>Calculated (%) Found (%)<br>C: 84.47   84.64<br>H: 7.09   7.25<br>N: 3.94   4.13 |
| 59 | (CH₃)₂C=CH—⟨phenyl⟩— | CH₃ | CH₃ | —CH₂—⟨phenyl⟩—O—⟨phenyl⟩ | $n_D^{20.0}$ 1.5816<br>$C_{28}H_{32}O$<br>Calculated (%) Found (%)<br>C: 87.45   87.27<br>H: 8.39   8.53 |
| 60 | CH₂FCH₂O—⟨phenyl⟩— | CH₃ | CH₃ | —CH₂—⟨phenyl⟩—O—⟨phenyl⟩ | $n_D^{20.0}$ 1.5643<br>$C_{26}H_{29}FO_2$<br>Calculated (%) Found (%)<br>C: 79.56   79.74<br>H: 7.45   7.27<br>F: 4.84   4.98 |

TABLE 1-continued

| Compound No. | Substituents in General Formula [I] Ar | R¹ | R² | R³ | Physical Property Values |
|---|---|---|---|---|---|
| 61 | CH₃OCH₂—C₆H₄— | CH₃ | CH₃ | —CH₂—C₆H₄—O—C₆H₅ | $n_D^{20}$ 1.5660<br>$C_{26}H_{30}O_2$<br>Calculated (%) / Found (%)<br>C: 83.38 / 83.57<br>H: 8.07 / 8.34 |
| 62 | Cl—C₆H₄— | CH₃ | CH₃ | —CH(CN)—C₆H₃(F)—O—C₆H₅ | $n_D^{20}$ 1.5630<br>$C_{25}H_{23}ClFNO$<br>Calculated (%) / Found (%)<br>C: 73.61 / 73.39<br>H: 5.68 / 5.55<br>Cl: 8.69 / 8.83<br>F: 4.66 / 4.71<br>N: 3.43 / 3.64 |
| 63 | Cl₂C=CH—C₆H₄— | CH₃ | CH₃ | —CH₂—C₆H₄—O—C₆H₅ | $n_D^{20}$ 1.5977<br>$C_{26}H_{26}Cl_2O$<br>Calculated (%) / Found (%)<br>C: 80.08 / 80.23<br>H: 6.72 / 6.58<br>Cl: 9.09 / 9.36 |
| 64 | C₂H₅OC(O)—C₆H₄— | CH₃ | CH₃ | —CH₂—C₆H₄—O—C₆H₅ | $n_D^{20}$ 1.5655<br>$C_{27}H_{30}O_3$<br>Calculated (%) / Found (%)<br>C: 80.56 / 80.38<br>H: 7.51 / 7.65 |
| 65 | CHF₂CF₂O—C₆H₄— | CH₃ | CH₃ | —CH₂—C₆H₄—O—C₆H₅ | $n_D^{20.0}$ 1.5266<br>$C_{26}H_{26}F_4O_2$<br>Calculated (%) / Found (%)<br>C: 69.94 / 70.18<br>H: 5.87 / 5.93<br>F: 17.02 / 17.20 |
| 66 | CHF₂CF₂O—C₆H₄— | CH₃ | CH₃ | —CH₂—C₆H₃(F)—O—C₆H₅ | $n_D^{20.5}$ 1.5194<br>$C_{26}H_{25}F_5O_2$<br>Calculated (%) / Found (%)<br>C: 69.67 / 69.89<br>H: 5.61 / 5.73<br>F: 21.15 / 21.36 |
| 67 | C₂H₅O—C₆H₃(Cl)— | CH₃ | CH₃ | —CH₂—C₆H₃(F)—O—C₆H₄—F | $n_D^{20.0}$ 1.5528<br>$C_{26}H_{27}ClF_2O_2$<br>Calculated (%) / Found (%)<br>C: 70.34 / 70.16<br>H: 5.90 / 5.98<br>Cl: 7.99 / 8.13<br>F: 8.56 / 8.45 |
| 68 | CH₂FCH₂OC(O)—C₆H₄— | CH₃ | CH₃ | —CH₂—C₆H₄—O—C₆H₅ | $n_D^{20}$ 1.5613<br>$C_{27}H_{29}FO_3$<br>Calculated (%) / Found (%)<br>C: 77.12 / 77.31<br>H: 6.95 / 6.74<br>F: 4.52 / 4.71 |
| 69 | CHF₂CF₂OC(O)—C₆H₄— | CH₃ | CH₃ | —CH₂—C₆H₄—O—C₆H₅ | $n_D^{19.5}$ 1.5684<br>$C_{27}H_{26}F_4O_3$<br>Calculated (%) / Found (%)<br>C: 68.34 / 68.57<br>H: 5.52 / 5.34<br>F: 16.02 / 16.17 |

The compounds of the present invention have an active structure quite different from those of the conventional agricultural chemicals. They have an excellent insecticidal activity to sanitary insect pests such as fly, mosquito and cockroach and agricultural insect pests such as planthoppers, leafhoppers, worms, moths, leaf holders, aphids, borers and mites, especially green rice leafhopper, and furthermore, they are effective for controlling stored grain insect pests such as grain mite, Indian meal moth and rice weevil, animal-parasitic mites and lice, and other insect pests. Furthermore, the compounds of the present invention are excellent in the fast-acting property and residual activity and have a flushing effect. Moreover, the compounds of the present invention have not only a knock-down effect to kill insect pests but also a repellent action of insect pests from hosts. Still further, the compounds of the present invention are advantageous in that the phytotoxicity to plants of Solanacede, which is observed in Fenvalerate, one of typical instances of synthetic pyrethroids, is not observed at all. In addition, the compounds of the present invention are very low in the toxicity to mammals. And moreover, some compounds of the present invention have a substantially high safety to fishes and they are suitably applied for controlling insect pests in paddy fields and aquatic insect pests such as larvae of mosquitoes and gnats and also are used for aerial application over broad districts including lakes, marshes, ponds and rivers without a fear of extermination of fishes.

Accordingly, insecticidal and acaricidal compositions comprising the compounds of the present invention can be applied very widely in various fields and have a very high controlling effect to agricultural and horticultural insect pests, stored grain insects, sanitary insect pests, house hold insect pests, forest insect pests and aquatic insect pests. Moreover, they are very safe and can be supplied at low costs in the form of various formulations.

Insect pests to which the insecticidal and acaricidal composition of the present invention can be applied are described below.

[Scientific name—Common name]

1. Hemiptera:
   *Nephtettix cincticeps* Uhler-Green rice leafhopper
   *Sogata furcifera* Horváth-White-backed rice planthopper
   *Nilaparvata lugens* Stal-Brown rice planthopper
   *Laodelphax striatellus* Fallén-Small brown planthopper
   *Eurydema rugosum* Motschulsky-Cabbage bug
   *Eysarcoris parvus* Uhler-Whitespotted spined bug
   *Haryomorpha mista* Uhler-Brown-marmorated stink bug
   *Lagynotomus elongatus* Dallas-Rice stink bug
   *Nezara viridula* Linné-Sourthern green stink bug
   *Cletus trigonus* Thunberg-Slender rice bug
   *Stephanitis nashi* Esaki et Takeya-Japanese pear lace bug
   *Stephanitis pyrioides* Scott-Azalea lace bug
   *Psylla pyrisuga* Förster-Pear sucker
   *Psylla mali* Schmidberger-Apple sucker
   *Aleurolobus taonabae* Kuwana-Grape whitefly
   *Dialeurodes citri* Ashmead-Citrus whitefly
   *Trialeurodes vaporariorum* Westwood-Greenhouse whitefly
   *Aphis gossypii* Glover-Cotton aphid
   *Brevicoryne brassicae* Linné-Cabbage aphid
   *Myzus persicae* Sulzer-Green peach aphid
   *Rhopalosiphum maidis* Fitch-Corn leaf aphid
   *Icerya purchasi* Maskell-Cottonycushion scale
   *Planococcus citri* Risso-Citrus mealybug
   *Unaspis yanonensis* Kuwana-Arrowhead scale
2. Lepidoptera:
   *Canephora asiatica* Staudinger-Mulberry bagworm
   *Spulerina astaurcta* Meyrick-Pear bark miner
   *Phyllonorycter ringoneela* Matsumura-Apple leafminer
   *Plutella xylostella* Linné-Diamond back moth
   *Promalactis inopisema* Butler-Cotton seedworm
   *Adoxophyes orana* Fischer von Röslerstamm-Smaller tea tortrix
   *Bactra furfurana* Haworth-Mat rush worm
   *Leguminivora glycinivorella* Matsumura-Soybean pod borer
   *Cnaphalocrocis medinalis* Guenée-Rice leaf roller
   *Etiella zinckenella* Treitschke-Lima-bean pod borer
   *Ostrinia furnacalis* Guenée-Oriental corn borer
   *Pleuroptya derogata* Fabricius-Cotton leaf roller
   *Hyphantria cunea* Drury-Fall webworm
   *Abraxas miranda* Butler-Magpie moth
   *Lymantria dispar* japonica Motschulsky-Gypsy moth
   *Phalera flavescens* Bremer et Grey-Cherry caterpillar
   *Agrotis segetum* Denis et Schiffermüller-Cutworm
   *Helicoverpa armigera* Hübner-Cotton boll worm
   *Pseudaletia separata* Walker-Armyworm
   *Mamestra brassicae* Linné-Cabbage armyworm
   *Plusia nigrisigna* Walker-Beet semi-looper
   *Spodoptera litura* Fablicius-Common cutworm
   *Parnara guttata* Bremer et Grey-Rice skipper
   *Pieris rapae* crucivora Boisduval-Common cabbageworm
   *Chilo suppressalis* Walker-Rice stem borer
3. Coleoptera:
   *Melanotus fortnumi* Candéze-Sweetpotato wireworm
   *Anthrenus verbasci* Linné-Varied carpet beetle
   *Tenebroides mauritanicus* Linné-Cadelle
   *Lyctus brunneus* Stephens-Powder post beetle
   *Henosepilachna vigintioctopunctata* Fablicius-28-Spotted lady beetle
   *Monochamus alternatus* Hope-Japanese pine sawyer
   *Xylotrechus pyrrhoderus* Bates-Grape borer
   *Aulacophora femoralis* Motschulsky-Cucurbit leaf beetle
   *Oleuma oryzae* Kuwayama-Rice leaf beetle
   *Phyllotreta striolata* Fablicius-Striped flea beetle
   *Callosobruchus chinensis* Linné-Azuki bean weevil
   *Echinocnemis squameus* Billberg-Rice plant weevil
   *Stiophilus oryzae* Linné-Rice weevil
   *Apoderus erythrogaster* Vollenhoven-Small black leaf-cut weevil
   *Rhynchites heros* Roelofs-Peach curculio
   *Anomala cuprea* Hope-Cupreous chafer
   *Popillia japonica* Newman-Japanese beetle
4. Hymenoptera:
   *Athalia rosae japonensis* Rhower-Cabbage sawfly
   *Arge similis* Vollenhoven-Azalea argid sawfly
   *Arge pagata* Panzer-Rose argid sawfly
5. Diptera:
   *Tipula aino* Alexander-Rice crane fly
   *Culex pipiens* fatigans Wiedemann-House mosquito
   *Aedes aegypti* Linné-Yellow-fever mosquito
   *Asophondylia sp.*-Soybean pod gall midge
   *Hylemya antiqua* Meigen-Onion maggot
   *Hylemya platura* Meigen-Seed corn maggot
   *Busca domestica vicina* Macquart-House fly
   *Dacus cucurbitae* Coquillett-Melon fly
   *Chlorops oryzae* Matsumura-Rice stem maggot
   *Agromyza oryzae* Munakata-Rice leafminer
6. Siphonaptera:
   *Pulex irritans* Linné-Human flea
   *Xenopsylla cheopis* Rothschild-Tropical rat flea
   *Ctenocephalides canis* Curtis-Dog flea
7. Thysanoptera:
   *Scirtothrips dorsalis* Hood-Yellow tea thrips

*Thrips tabaci* Lindeman-Onion thrips
*Chloethrips oryzae* Williams-Rice thrips
8. Anoplura:
   *Pediculus humanus corporis* De Geer-Body louse
   *Phthirus pubis* Linné-Crab louse
   *Haematopinus eurysternus* Nitzsh-Short-nosed cattle louce
9. Psocoptera:
   *Trogium pulsatsrium* Linné-Larger pale booklouse
   *Liposcelis bostrychophilus* Badonnel-Flattened booklice
10. Orthoptera:
    *Gryllotalpa africana palisot* de Beauvois-African mole cricket
    *Locusta migratoria danica* Linné-Asiatic locust
    *Oxya yezoensis* Shiraki-Short-Winged rice grass hopper
11. Dictyoptera:
    *Blattella germanica* Linné-German cockroach
    *Periplaneta fuliginosa* Serville-Smokybrown cockroach
12. Acarina:
    *Boophilus microplus* Canestrini-Bull tick
    *Polyphagotarsonemus latus* Banks-Broad mite
    *Panonychus citri* McGregor-Citrus red mite
    *Tetranychus cinnabarinus* Boisduval-Carmine spider mite
    *Tetranychus urticae* Koch-Two-spotted spider mite
    *Rhizoglyphus echinophus* Fumouze et Robin-Bulb mite When the compound of the present invention is actually applied, it may be used singly without incorporation of other components. Ordinarily, however, in order to facilitate the application, the compound of the present invention is mixed with a carrier to prepare an appropriate formulation and this formulation is diluted according to need before the application. No particular condition is necessary for preparing a formulation of the compound of the present invention but according to methods known to those skilled in the art of manufacture of agricultural chemicals, the compound of the present invention may optionally be prepared into any of various formulations such as emulsifiable concentrates, wettable powders, dusts, granules, fine granules, oils, aerosols, heating fumigants (mosquito coil and electric incenses), smoking agents such as fogging agents, non-heating fumigants and poisonous diets. These formulations may be applied to various uses according to intended objects.

Furthermore, it is possible to obtain an enhanced insecticidal and acaricidal effect by using two or more of the compounds of the present invention in combination. Moreover, multi-purpose compositions having excellent activities can be obtained by combining the compounds of the present invention with other physiologically active substances, for example, allethrin, N-(chrysanthemoylmethyl)-3,4,5,6-tetrahydrophthalimide, 5-benzyl-3-furylmethyl chrysanthemate, 3-phenoxybenzyl chrysanthemate, 5-propargylfurfuryl chrysanthemate, other known cyclopropanecarboxylic acid esters, such as 3-phenoxybenzyl 3-(2,2-dichlorovinyl)-2,2-dimethyl-cyclopropane-1-carboxylate, 3-phenoxy-α-cyano-benzyl 3-(2,2-dichlorovinyl)-2,2-dimethyl-cyclopropane-1-carboxylate, 3-phenoxy-α-cyano-benzyl 3-(2,2-dibromovinyl)-2,2-dimethyl-cyclopropane-1-carboxylate, other synthetic pyrethroids such as 3-phenoxy-α-cyanobenzyl α-isopropyl-4-chlorophenylacetate and isomers thereof, pyrethrum extracts, organophosphorous insecticides such as 0,0-diethyl-0-(3-oxo-2-phenyl-2H-pyridazin-6-yl)-phosphorothioate (supplied under registered tradename "Ofunack" by Mitsui Toatsu Chemicals, Inc.), 0,0-dimethyl-0-(2,2-dichlorovinyl)phosphate (DDVP), 0,0-dimethyl-0-(3-methyl-4-nitrophenyl)phosphorothioate, diazinon, 0,0-dimethyl-0-4-cyanophenylphosphorothioate, 0,0-dimethyl-S-[α-(ethoxycarbonyl)benzyl]phosphorodithioate, 2-methoxy-4H-1,3,2-benzodioxaphosphorin-2-sulfide and 0-ethyl-0-4-cyanophenyl phenyl phosphonothioate, carbamate insecticides such as 1-naphthyl-N-methylcarbamate (NAC), m-tolyl-N-methylcarbamate (MTMC), 2-dimethylamino-5,6-dimethylpyrimidin-4-yl-dimethylcarbamate (Pyrimer), 3,4-dimethylphenyl N-methylcarbamate and 2-isopropoxyphenyl N-methylcarbamate, arylpropyl ether insecticides such as 3-phenoxybenzyl 2-(4-chlorophenyl)-2-methylpropyl ether, 3-phenoxy-4-fluorobenzyl 2-(4-chlorophenyl)-2-methylpropyl ether, 3-phenoxybenzyl 2-(4-ethoxyphenyl)-2-methylpropyl ether, 3-phenoxy-4-fluorobenzyl 2-(4-ethoxyphenyl)-2-methylpropyl ether, other insecticides, acaricides, fungicides, nematocides, herbicides, plant growth regulators, fertilizers, BT agents, insect hormones and other agricultural chemicals. Furthermore, synergistic effects are expected by combining the compounds of the present invention with these physiologically active substances.

Furthermore, the effects of the compounds of the present invention can be multiplied by combining the compounds of the present invention with synergists for pyrethroids, such as α-[2-(2-butoxyethoxy)ethoxy]-4,5-methylenedioxy-2-propyltoluene (piperonyl butoxide), 1,2-methyleneidoxy-4-[2-(octylsulfinyl)propyl]benzene (Sulfoxide), 4-(3,4-methylenedioxyphenyl)-5-methyl-1,3-dioxane (Safroxane), N-(2-ethylhexyl)-bicylo(2,2,1)-hepta-5-ene-2,3-dicarboxyimide (MGK-264), octachlorodipropyl ether (S-421) and isobornyl thiocyanoacetate (Sarnite). Though the compounds of the present invention are highly stable against light, heat and oxidation, compositions having much stabilized activities can be obtained by mixing the compounds of the present invention with appropriate amounts of antioxidants or ultraviolet absorbents, for example, phenol derivatives such as BHT (2,6-di-tert-butyl-4-methylphenol) and BHA (butylhydroxyanisole), bisphenol derivatives, arylamines such as phenyl-α-naphthylamine, phenyl-β-naphthylamine and phenetidine, acetone condensates thereof and benzophenone type compounds, as stabilizers according to need.

In the insecticidal and acaricidal composition of the present invention, the above-described ether or thioether derivative is incorporated in an amount of 0.0001 to 95% by weight, preferably 0.001 to 50% by weight.

The insecticidal and acaricidal composition of the present invention will now be described in detail with reference to the following Formulation Examples that by no means limit the scope of the present invention. Incidentally, all of "parts" given hereinafter are by weight, and the compounds of the present invention are designated by compound numbers shown in Table 1.

FORMULATION EXAMPLE 1

20 parts of the compound of the present invention, 10 parts Sorpol 355S (registered trademark for the mixture of a nonionic surface active agent and an anionic surface active agent, supplied by Toho Chemical Industrial Co., Ltd.) and 70 parts of xylene are mixed and stirred to give an emulsifiable concentrate.

FORMULATION EXAMPLE 2

In 10 parts of acetone was dissolved 1 part of the compound of the present invention, and 99 parts of clay for dusts was added to the solution and the acetone was evaporated to give a dust.

FORMULATION EXAMPLE 3

To 20 parts of the compound of the present invention was added 5 parts of a surface active agent, and the mixture was sufficiently blended and 75 parts of diatomaceous earth was added thereto. The mixture was blended in a crusher to give a wettable powder.

FORMULATION EXAMPLE 4

To 0.2 part of the compound of the present invention was added 2 parts of m-tolyl-N-methylcarbamate and 0.2 part of PAP (registered trademark for the property modifier (isopropyl acid phosphate), supplied by Nippon Chemical Industrial Co., Ltd.) was further added. The mixture was dissolved in 10 parts of acetone and 97.6 parts of clay for dusts was added to the solution. The mixture was blended in a crusher and acetone was evaporated to give a dust.

FORMULATION EXAMPLE 5

To 0.2 part of the compound of the present invention was added 2 parts of Ofunack (registered trademark for the product supplied by Mitsui Toatsu Chemicals, Inc.), and 0.2 part of PAP (described above) was further added. The mixture was dissolved in 10 parts of acetone and 97.6 parts of clay for dusts was added to the solution. The mixture was blended in a crusher and acetone was evaporated to give a dust.

FORMULATION EXAMPLE 6

To 0.1 part of the compound of the present invention was added 0.5 part of piperonyl butoxide, and the mixture was dissolved in kerosene so that the total amount was 100 parts, to give an oil solution.

FORMULATION EXAMPLE 7

To a mixture of 0.5 part of the compound of the present invention and 5 parts of Ofunack (described above) was added 5 parts of Sorpol SM-200 (registered trademark for the mixture of a nonionic surface active agent and an anionic surface active agent, supplied by Toho Chemical Industrial Co., Ltd.) and the mixture was dissolved in 89.5 parts of xylol to give an emulsifiable concentrate.

FORMULATION EXAMPLE 8

A solution formed by mixing 0.4 part of the compound of the present invention and 2.0 parts of piperonyl butoxide with 6 parts of xylol and 7.6 parts of deodorized kerosene was charged in an aerosol vessel, and a valve portion was attached to the vessel and 84 parts of a propellant (liquefied petroleum gas) was fed under pressure through the valve portion to give an aerosol.

FORMULATION EXAMPLE 9

In an appropriate amount of chloroform was dissolved 0.05 g of the compound of the present invention, and the solution was uniformly adsorbed on the surface of an asbestos sheet having a size of 2.5 cm×1.5 cm×0.3 mm (thickness) to form a heating insecticidal fumigant to be placed on a hot plate.

FORMULATION EXAMPLE 10

In 20 ml of methanol was dissolved 0.5 g of the compound of the present invention, and the solution was homogeneously mixed with stirring with 99.5 g of an incense carrier (3:5:1 mixture of tub powder, pyrethrum marc powder and wood flour). Methanol was evaporated and 150 ml of water was added. The mixture was sufficiently kneaded and the kneaded mixture was molded and dried to give a mosquito coil.

FORMULATION EXAMPLE 11

To a mixture of 1 part of the compound of the present invention, 3 parts of Ofunack (described above), 2 parts of Serogen 7A (registered trademark for the product (carboxymethylcellulose) supplied by Dai-ichi Kogyo Seiyaku) and 2 parts of Sunekisu (sodium ligninosulfonate supplied by Sanyo Kokusaaku Pulp) was added 92 parts of clay, and an appropriate amount of water was added and the mixture was granulated and sieved to give a granule.

FORMULATION EXAMPLE 12

The underdescribed emulsifiable concentrates were prepared in the same manner as described in Formulation Example 1.

| Emulsifiable Concentrate | The Compound of The Present Invention (Active Ingredient) | Surface Active Agent | Solvent (Xylol) |
|---|---|---|---|
| 5% Form | 5 | 2.5 | 92.5 |
| 10% Form | 10 | 4 | 85 |
| 20% Form | 20 | 8 | 72 |
| 40% Form | 40 | 10 | 50 |
| 80% Form | 80 | 15 | 5 |

Note: Numbers stand for parts.

By mixing ingredients, emulsifiable concentrates having each intended amount of active ingredient are prepared. The emulsifiable concentrates having a high amount, viz. 95% of active ingredient can be prepared by mixing active ingredient with surface active agent without solvent, and thus obtained emulsifiable concentrates are useful for an aerial application in which a decreased amount is used for scattering.

FORMULATION EXAMPLE 13

In the cases of 5, 20 and 60 parts of the compound of the present invention, wettable powders were prepared in the same manner as described in Formulation Example 3.

When the compound of the present invention is actually applied, it is ordinarily applied at a rate of 1 to 300 g, preferably 2 to 100 g, especially preferably 5 to 20 g, as the active ingredient per 10 areas.

In order to demonstrate that the compounds of the present invention have excellent insecticidal and acaricidal activities and they are very low toxic to fishes, the results of Tests will now be described.

Compounds (a) through (g) described below were tested as comparative compounds in the same manner as the compounds of the present invention. All the tests were doubly carried out. Namely, each result was expressed by an average value of two data.

(a) DDVP
(b) Ofunack
(c) Diazinon
(d) Methomyl (e) Kelthane
(f) PCP sodium salt
(g) Fenvalerate Pesticide Science Vol. 7, 241(1976)

Test 1 (Effect on Common Cutworm)

The emulsifiable concentrate of the test compound, prepared according to the method described in Formulation Example 1, was diluted with water to a specified concentration. Sweet potato leaves were sufficiently immersed in the dilution. The sweet potato leaves were dried and placed in a plastic cup having a diameter of 10 cm, and 10 third-instar larvae of common cutworm were set free in each cup. 48 hours after, the numbers of killed and living larvae were counted and the mortality was calculated.

The results are shown in Table 2. The compounds of the present invention are designated by the compound numbers shown in Table 1 hereinafter.

TABLE 2

| Test Compound | Mortality (%) | |
|---|---|---|
| | 100 ppm | 20 ppm |
| Compound 1 | 100 | 100 |
| Compound 3 | 100 | 100 |
| Compound 4 | 100 | 100 |
| Compound 6 | 100 | 100 |
| Compound 8 | 100 | 95 |
| Compound 9 | 100 | 100 |
| Compound 10 | 100 | 100 |
| Compound 17 | 100 | 50 |
| Compound 19 | 100 | 70 |
| Compound 20 | 100 | 100 |
| Compound 24 | 100 | 100 |
| Compound 27 | 100 | 100 |
| Compound 29 | 100 | 100 |
| Compound 32 | 100 | 100 |
| Compound 35 | 100 | 100 |
| Compound 37 | 100 | 80 |
| Compound 44 | 90 | 40 |
| Compound 45 | 100 | 80 |
| Compound 46 | 100 | 85 |
| Compound 48 | 100 | 60 |
| Compound 52 | 100 | 100 |
| Compound 54 | 90 | 45 |
| Compound 55 | 100 | 100 |
| Compound 57 | 100 | 100 |
| Compound 58 | 100 | 80 |
| Compound 60 | 100 | 90 |
| Compound 63 | 100 | 70 |
| Compound 64 | 90 | 40 |
| Compound 65 | 100 | 100 |
| Compound 66 | 100 | 100 |
| Compound 67 | 100 | 60 |
| Comparative Compound (a) | 60 | 0 |
| Comparative Compound (b) | 100 | 80 |

Test 2 (Effect on Green Rice Leafhopper)

Four or five seedlings of paddy rice with three leaves were bundled, and thereon the same dilution of the emulsifiable concentrate as used in Test 1 was sprayed in an amount of 3 ml. The bundle was dried and covered with a metal net cylinder, and 10 female adults of green rice leafhopper were set free in the cylinder. 48 hours after, the number of killed adults was counted.

The results are shown in Table 3.

TABLE 3

| Test Compound | Mortality (%) | |
|---|---|---|
| | 100 ppm | 20 ppm |
| Compound 2 | 100 | 80 |
| Compound 3 | 100 | 100 |
| Compound 5 | 100 | 100 |

TABLE 3-continued

| Test Compound | Mortality (%) | |
|---|---|---|
| | 100 ppm | 20 ppm |
| Compound 6 | 100 | 100 |
| Compound 7 | 100 | 65 |
| Compound 8 | 100 | 100 |
| Compound 9 | 100 | 100 |
| Compound 10 | 100 | 100 |
| Compound 11 | 90* | 60* |
| Compound 12 | 80* | 40* |
| Compound 13 | 100 | 40 |
| Compound 14 | 90 | 50 |
| Compound 15 | 95 | 70 |
| Compound 17 | 100 | 95 |
| Compound 18 | 100 | 100 |
| Compound 20 | 100 | 100 |
| Compound 21 | 100 | 100 |
| Compound 22 | 95 | 50 |
| Compound 23 | 100 | 75 |
| Compound 24 | 100 | 100 |
| Compound 25 | 100 | 90 |
| Compound 26 | 100 | 50 |
| Compound 27 | 100 | 100 |
| Compound 28 | 100 | 80 |
| Compound 30 | 100 | 70 |
| Compound 31 | 100 | 100 |
| Compound 32 | 100 | 100 |
| Compound 33 | 100 | 100 |
| Compound 34 | 100 | 50 |
| Compound 36 | 100 | 100 |
| Compound 38 | 100 | 100 |
| Compound 39 | 100 | 90 |
| Compound 40 | 100 | 60 |
| Compound 41 | 100 | 100 |
| Compound 42 | 100 | 100 |
| Compound 43 | 100 | 75 |
| Compound 45 | 100 | 80 |
| Compound 46 | 100 | 100 |
| Compound 47 | 100 | 75 |
| Compound 49 | 100 | 60 |
| Compound 50 | 100 | 50 |
| Compound 51 | 90 | 60 |
| Compound 52 | 100 | 100 |
| Compound 53 | 100 | 100 |
| Compound 54 | 90 | 50 |
| Compound 55 | 100 | 100 |
| Compound 56 | 100 | 100 |
| Compound 57 | 100 | 100 |
| Compound 58 | 100 | 100 |
| Compound 59 | 100 | 70 |
| Compound 60 | 100 | 100 |
| Compound 61 | 100 | 100 |
| Compound 62 | 100 | 45 |
| Compound 63 | 100 | 100 |
| Compound 65 | 100 | 100 |
| Compound 66 | 100 | 100 |
| Compound 67 | 100 | 100 |
| Compound 68 | 80 | 40 |
| Compound 69 | 100 | 75 |
| Comparative Compound (b) | 100 | 90 |
| Comparative Compound (c) | 80 | 10 |

*Rate of Number of Adults Knocked-Down

Test 3 (Effect on German Cockroach)

One ml of an acetone solution of a test compound of a specified concentration was poured in a high Petri dish having a diameter of 9 cm and a height of 9 cm. The Petri dish was allowed to stand, and thereby the acetone was evaporated. The upper part of the inner wall of the Petri dish was treated with butter to prevent the adults of German cockroach from escaping from the Petri dish. 10 female adults of German cockroach were set free in each Petri dish. 48 hours after, the number of killed adults was counted.

The results are shown in Table 4.

TABLE 4

| Test Compound | Mortality (%) | |
|---|---|---|
| | 5 mg/m² | 1 mg/m² |
| Compound 1 | 100 | 80 |
| Compound 4 | 100 | 40 |
| Compound 6 | 100 | 100 |
| Compound 10 | 100 | 100 |
| Compound 20 | 100 | 100 |
| Compound 24 | 100 | 100 |
| Compound 27 | 100 | 100 |
| Compound 29 | 100 | 100 |
| Compound 31 | 100 | 100 |
| Compound 35 | 100 | 70 |
| Compound 52 | 100 | 70 |
| Compound 53 | 100 | 80 |
| Compound 55 | 100 | 100 |
| Compound 56 | 100 | 40 |
| Compound 57 | 100 | 100 |
| Compound 65 | 95 | 30 |
| Compound 66 | 100 | 65 |
| Comparative Compound (b) | 10 | 0 |
| Comparative Compound (c) | 80 | 0 |

Test 4 (Effect on Two-Spotted Spider Mite)

A kidney bean leaf disc (20 mm in diameter) perforated with a cork borer was placed on water-impregnated absorbent cotton, and thereon 20 adults of two-spotted spider mite were set free, and the resulting set was allowed to stand around the clock. The same dilution of the emulsifiable concentrate of a test compound having a concentration of 200 ppm as used in Test 1 and Test 2, was applied by an applicator having a diameter of 20 cm and a height of 60 cm in an amount of 3 ml. 24 hours after, the number of killed adults was counted.

The results are shown in Table 5.

TABLE 5

| Test Compound | Mortality (%) |
|---|---|
| Compound 9 | 100 |
| Compound 19 | 43 |
| Compound 20 | 100 |
| Compound 24 | 95 |
| Compound 35 | 85 |
| Compound 40 | 70 |
| Compound 43 | 60 |
| Compound 44 | 85 |
| Compound 52 | 100 |
| Compound 53 | 100 |
| Compound 54 | 100 |
| Compound 56 | 100 |
| Compound 57 | 91 |
| Compound 60 | 90 |
| Compound 61 | 93 |
| Compound 64 | 70 |
| Compound 66 | 100 |
| Comparative Compound (a) | 33 |
| Comparative Compound (e) | 100 |

Test 5 (Fish Toxicity)

A water tank having a width of 60 cm, a length of 30 cm and a height of 40 cm was filled with water, and 10 yearling carps having a body length of about 5 cm were set free in the tank and adapted to the environment in the tank. An acetone solution of a test compound was applied into water so as to become a concentration of 1 or 0.1 ppm in water by adding said acetone solution at a rate of one part by volume per 100 parts by volume of water. 48 hours after, the number of killed and living carps was counted and the effect of a test compound on carps was examined.

TABLE 6

| Test Compound | Mortality (%) 48 Hours After | |
|---|---|---|
| | 1 ppm | 0.1 ppm |
| Compound 1 | 0 | 0 |
| Compound 4 | 0 | 0 |
| Compound 5 | 0 | 0 |
| Compound 6 | 0 | 0 |
| Compound 8 | 0 | 0 |
| Compound 10 | 30 | 5 |
| Compound 17 | 0 | 0 |
| Compound 18 | 0 | 0 |
| Compound 20 | 0 | 0 |
| Compound 21 | 0 | 0 |
| Compound 23 | 0 | 0 |
| Compound 24 | 0 | 0 |
| Compound 26 | 0 | 0 |
| Compound 33 | 0 | 0 |
| Compound 35 | 0 | 0 |
| Compound 38 | 0 | 0 |
| Compound 41 | 0 | 0 |
| Compound 55 | 0 | 0 |
| Compound 57 | 0 | 0 |
| Compound 67 | 0 | 0 |
| Comparative Compound (f) | 100 | 55 |
| Comparative Compound (g) | 100 | 100 |

What is claimed is:

1. An aromatic alkane derivative represented by the following formula (I)

wherein Ar stands for an aryl group selected from the group consisting of a napthyl group and phenyl groups which may be unsubstituted or substituted with the same or different substituents selected from the group consisting of a halogen atom; an alkyl($C_1$-$C_3$), haloalkyl($C_1$-$C_3$), alkoxy($C_1$-$C_3$), haloalkoxy($C_1$-$C_3$), alkenyl($C_2$-$C_3$), haloalkenyl($C_2$-$C_3$), alkoxyalkyl($C_2$-$C_3$), haloalkenyloxy($C_2$-$C_3$), alkynyloxy($C_2$-$C_3$), alkoxycarbonyl($C_2$-$C_3$), haloalkoxycarbonyl($C_2$-$C_3$), phenoxy, nitrile or methylenedioxy group, $R^1$ stands for a methyl, ethyl or isopropyl group and $R^2$ stands for a hydrogen atom or a methyl group, or $R^1$ and $R^2$ together with the carbon atom to which they re attached jointly represent a cycloalkyl group having 3 to 6 carbon atoms, which may be unsubstituted or substituted with halogen atoms or methyl groups, and $R^3$ stands for a group represented by the following general formula (III):

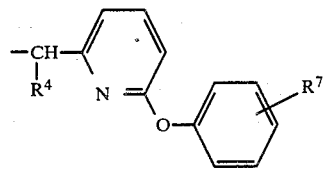

wherein $R^4$ stands for a hydrogen atom, or an ethynyl or cyano group, $R^7$ stands for a hydrogen or halogen atom, or an alkoxy group having 1 to 3 carbon atoms.

2. An insecticidal and acaricidal composition, comprising a carrier or vehicle and, as an active ingredient, an insecticidally or acaricidally effective amount of one or two members selected from the group consisting of aromatic alkane derivatives represented by the following formula (I):

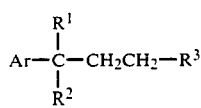 (I)

wherein Ar stands for an aryl ring selected from the group consisting of naphthyl or phenyl which is unsubstituted or substituted with the same or different substituents selected from the group consisting of a halogen atom, an alkyl($C_1$-$C_3$), haloalkyl($C_1$-$C_3$), alkoxy($C_1$-$C_3$), haloalkoxy($C_1$-$C_3$, alkenyl($C_2$-$C_3$), haloalkenyl($C_2$-$C_3$), alkoxyalkyl($C_2$-$C_3$), haloalkenyloxy($C_2$-$C_3$), alkynyloxy($C_2$-$C_3$), alkoxycarbonyl($C_2$-$C_3$), haloalkoxycarbonyl($C_2$-$C_3$), phenoxy, nitrile or methylenedioxy group, $R^1$ stands for a methyl, ethyl or isopropyl group and $R^2$ stands for a hydrogen atom or a methyl group, or $R^1$ and $R^2$ together with the carbon atom to which they are attached jointly represent a cycloalkyl group having 3 to 6 carbon atoms, which may be unsubstituted or substituted with a halogen atom or methyl group, and $R^3$ stands for a group represented by the following general formula (III):

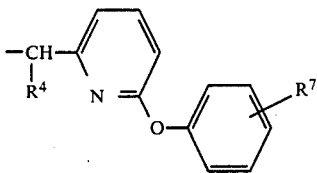 (III)

wherein $R^4$ stands for a hydrogen atom, or an ethynyl or cyano group, $R^7$ stands for a hydrogen or halogen atom, or an alkoxy group having 1 to 3 carbon atoms.

3. A method of combatting insect pests and/or acarids comprising contacting the insect pests or acarids with a pesticidally effective amount of a compound in accordance with claim 1.

* * * * *